(12) United States Patent
Zhang et al.

(10) Patent No.: US 11,083,577 B2
(45) Date of Patent: Aug. 10, 2021

(54) HEART VALVE PROSTHESIS

(71) Applicant: Suzhou Jiecheng Medical Technology Co., Ltd., Jiangsu (CN)

(72) Inventors: Ji Zhang, Burnaby (CA); Brandon G. Walsh, Kaysville, UT (US); Cheng Yong Yang, Foster City, CA (US); Jinhua Zhu, San Francisco, CA (US); Dennis McMahon, Windsor, CA (US)

(73) Assignee: JC MEDICAL, INC., Burlingame, CA (US)

( * ) Notice: Subject to any disclaimer, the term of this patent is extended or adjusted under 35 U.S.C. 154(b) by 196 days.

(21) Appl. No.: 16/240,354

(22) Filed: Jan. 4, 2019

(65) Prior Publication Data

US 2019/0209315 A1  Jul. 11, 2019

Related U.S. Application Data

(60) Provisional application No. 62/781,537, filed on Dec. 18, 2018, provisional application No. 62/756,556, filed on Nov. 6, 2018, provisional application No. 62/614,489, filed on Jan. 7, 2018.

(51) Int. Cl.
*A61F 2/24* (2006.01)
*A61M 25/01* (2006.01)
*A61F 2/966* (2013.01)

(52) U.S. Cl.
CPC .......... *A61F 2/2436* (2013.01); *A61F 2/2412* (2013.01); *A61F 2/2415* (2013.01); *A61F 2/2418* (2013.01); *A61F 2/2463* (2013.01); *A61F 2/246* (2013.01); *A61F 2/2433* (2013.01); *A61F 2/966* (2013.01); *A61F 2002/9665* (2013.01); *A61M 25/0136* (2013.01)

(58) Field of Classification Search
CPC ........ A61F 2/24; A61F 2/2412; A61F 2/2415; A61F 2/2418; A61F 2/2436; A61F 2/2463; A61F 2/2433; A61F 2/246; A61F 2/966; A61F 2002/9665; A61M 25/0136
See application file for complete search history.

(56) References Cited

U.S. PATENT DOCUMENTS

| | | |
|---|---|---|
| 7,025,780 B2 | 4/2006 | Gabbay |
| 7,387,640 B2 | 6/2008 | Cummings |
| 7,510,572 B2 | 3/2009 | Gabbay |
| 7,621,948 B2 | 11/2009 | Herrmann et al. |
| 7,789,909 B2 | 9/2010 | Andersen et al. |
| 7,803,185 B2 | 9/2010 | Gabbay |
| 7,824,443 B2 | 11/2010 | Salahieh et al. |

(Continued)

FOREIGN PATENT DOCUMENTS

| | | |
|---|---|---|
| WO | WO 2004/019825 | 3/2004 |
| WO | WO 2005/002466 | 1/2005 |

(Continued)

OTHER PUBLICATIONS

PCT Written Opinion for PCT/US19/12406, published Jul. 2019, 17 pages.

*Primary Examiner* — George J Ulsh
(74) *Attorney, Agent, or Firm* — Nathan S. Smith; Morgan, Lewis & Bockius LLP

(57) ABSTRACT

The present disclosure relates to heart valve prostheses, delivery devices, actuation handles, and other improved devices and methods that facilitate delivery of a heart valve prosthesis to a defective native valve structure in a patient, such as the aortic valve.

22 Claims, 29 Drawing Sheets

(56) References Cited

U.S. PATENT DOCUMENTS

| | | |
|---|---|---|
| 8,052,750 B2 | 11/2011 | Tuval et al. |
| 8,105,375 B2 | 1/2012 | Navia et al. |
| 8,313,525 B2 | 11/2012 | Tuval et al. |
| 9,554,903 B2 | 1/2017 | Rowe et al. |
| 2002/0032481 A1 | 3/2002 | Gabbay |
| 2003/0036791 A1 | 2/2003 | Bonhoeffer et al. |
| 2003/0040792 A1 | 2/2003 | Gabbay |
| 2003/0149478 A1 | 8/2003 | Figulla et al. |
| 2004/0260394 A1 | 12/2004 | Douk et al. |
| 2005/0137688 A1 | 6/2005 | Salahieh et al. |
| 2005/0137689 A1 | 6/2005 | Salahieh et al. |
| 2005/0251251 A1 | 11/2005 | Cribier |
| 2006/0173524 A1 | 8/2006 | Salahieh et al. |
| 2006/0217802 A1 | 9/2006 | Ruiz et al. |
| 2006/0259134 A1 | 11/2006 | Schwammenthal |
| 2006/0259135 A1 | 11/2006 | Navia et al. |
| 2007/0016286 A1 | 1/2007 | Herrmann et al. |
| 2007/0027533 A1 | 2/2007 | Douk |
| 2007/0027534 A1 | 2/2007 | Bergheim et al. |
| 2007/0100440 A1 | 5/2007 | Figulla et al. |
| 2007/0244552 A1 | 10/2007 | Salahieh et al. |
| 2007/0250151 A1 | 10/2007 | Pereira |
| 2007/0250161 A1 | 10/2007 | Dolan |
| 2007/0260225 A1 | 11/2007 | Sakakine |
| 2008/0071361 A1 | 3/2008 | Tuval et al. |
| 2008/0071363 A1 | 3/2008 | Tuval et al. |
| 2008/0082166 A1 | 4/2008 | Styrc et al. |
| 2008/0177381 A1 | 7/2008 | Navia et al. |
| 2009/0054968 A1 | 2/2009 | Bonhoeffer et al. |
| 2009/0054976 A1 | 2/2009 | Tuval et al. |
| 2009/0132035 A1 | 5/2009 | Roth et al. |
| 2009/0192585 A1 | 7/2009 | Bloom et al. |
| 2009/0216310 A1 | 8/2009 | Straubinger et al. |
| 2009/0240320 A1 | 9/2009 | Tuval et al. |
| 2009/0275934 A1 | 11/2009 | Baxter |
| 2009/0287299 A1 | 11/2009 | Tabor et al. |
| 2010/0100167 A1 | 4/2010 | Bortlein |
| 2010/0249915 A1 | 9/2010 | Zhang |
| 2010/0249916 A1 | 9/2010 | Zhang |
| 2010/0256751 A1 | 10/2010 | Rowe et al. |
| 2010/0274088 A1 | 10/2010 | West et al. |
| 2010/0286768 A1 | 11/2010 | Alkhatib |
| 2011/0202128 A1 | 8/2011 | Duffy |
| 2011/0264202 A1 | 10/2011 | Murray, III |
| 2013/0211508 A1 | 8/2013 | Lane et al. |
| 2013/0231735 A1 | 9/2013 | Deem |
| 2013/0261737 A1 | 10/2013 | Costello |
| 2015/0148894 A1 | 5/2015 | Damm |
| 2015/0320556 A1 | 11/2015 | Levi et al. |
| 2016/0015512 A1 | 1/2016 | Zhang et al. |
| 2016/0262884 A1 | 9/2016 | Lombardi |
| 2017/0165062 A1 | 6/2017 | Rothstein |
| 2018/0021129 A1 | 1/2018 | Peterson et al. |
| 2020/0253731 A1 | 8/2020 | Manash |

FOREIGN PATENT DOCUMENTS

| | | |
|---|---|---|
| WO | WO 2009/155561 | 12/2009 |
| WO | WO 2010/121076 | 10/2010 |
| WO | WO 2012/095455 | 7/2012 |
| WO | WO 2014/153152 | 9/2014 |
| WO | WO 2017/121194 | 7/2017 |
| WO | WO 2017/195125 | 11/2017 |

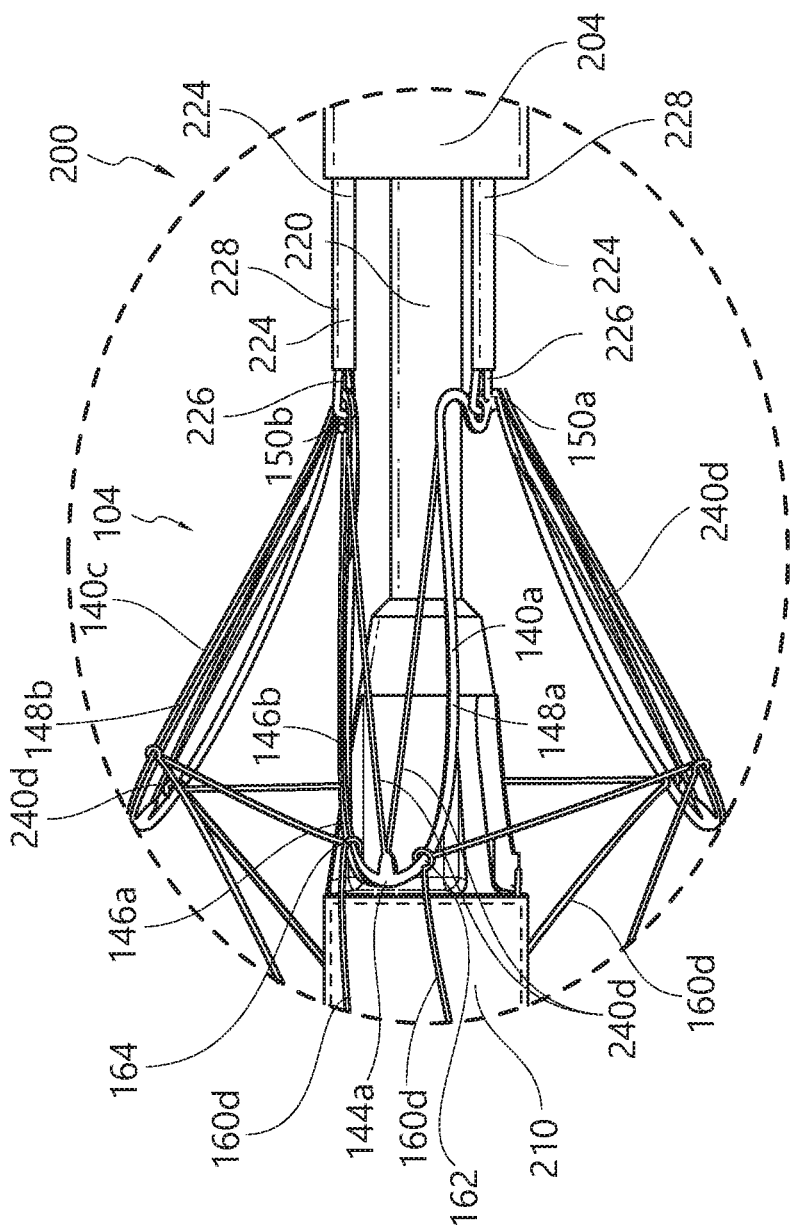

HEART VALVE PROSTHESIS

CROSS-REFERENCE TO RELATED APPLICATIONS

The present application claims the benefit of and priority to U.S. Provisional Application No. 62/614,489, filed on Jan. 7, 2018, U.S. Provisional Application No. 62/756,556, filed on Nov. 6, 2018, and U.S. Provisional Application No. 62/781,537, filed on Dec. 18, 2018, the entireties of each of which are incorporated herein by reference.

TECHNICAL FIELD

The present disclosure relates to devices and methods for the percutaneous delivery and implantation of a cardiac valve prosthesis. The valve prosthesis can be delivered in a compressed state within a sheath to the defective native valve and released in situ.

BACKGROUND

Prosthetic heart valves are used to replace damaged or diseased heart valves. In vertebrate animals, the heart is a muscular organ with four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is more common since they reside in the left side of the heart where pressures are the greatest.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open-heart surgery is particularly invasive and involves a lengthy and difficult recovery period.

The foregoing examples of the related art and limitations related therewith are intended to be illustrative and not exclusive. Other limitations of the related art will become apparent to those of skill in the art upon a reading of the specification and a study of the drawings.

SUMMARY

The present disclosure relates to heart valve prostheses, delivery devices, and actuation handles that can facilitate delivery of a heart valve prosthesis to a defective native valve structure in a patient, such as the aortic valve. In some embodiments, the delivery can be performed using a transcatheter approach.

The delivery devices and actuation handles can enable a clinician to more easily maneuver and advance the delivery device through blood vessels leading to the heart, as well as through tortuosities of such vessels, using a transvascular approach, such as a transfemoral approach. Indeed, some embodiments disclosed herein enable components of the heart valve prosthesis to be advanced in tandem, as an axially displaced unit (with or without partial or full overlapping between the components), while still being movably connected, movably attached, flexibly connected, displaceably connected, linked, or coupled to each other, thereby minimizing a passing profile or cross section of the delivery device. Optionally, the distance from which the components of the heart valve prosthesis may be serially displaced may be variable, such that various components are adjacent or potentially inches or feet away. Further, the interconnection of components of the heart valve prosthesis can allow different degrees of motion and can be set into an engaged or retained position that provides a limited range of motion. In some embodiments, the engaged position can also provide a preset relative positioning of the components of the heart valve prosthesis to facilitate proper placement and release of the heart valve prosthesis. Additionally, some embodiments can provide a clinician with a high degree of control and enhance the maneuverability of the heart valve prosthesis when implanting the heart valve prosthesis at the target location.

In accordance with some embodiments, a procedure is provided for a transcatheter aortic valve implantation (TAVI) and/or a transcatheter aortic valve replacement (TAVR). For example, in the TAVI procedure, a clinician can anchor the anchoring component of the heart valve prosthesis relative to the aortic valve annulus to guide the placement of the prosthetic leaflet structure. The valve prosthesis can comprise prosthetic leaflets, an anchoring component, a valve frame component, and a tethering component, which allows the anchoring component and the frame component to be placed serially in a delivery device in order to reduce the overall crossing profile of the delivery device. The tethering component can be coupled to the anchoring component and the frame component to permit a range of motion and in some embodiments, to restrict other motion. The tethering component can be slidable relative to the anchoring component between a released position and a retained position. In the retained position, the tethering component can allow relative movement of the valve frame component and a preset or predetermined position which the valve frame component is optimally located relative to the anchoring component, which can facilitate placement and release of the valve prosthesis.

For example, in some embodiments, the interconnection can be implemented using a novel approach of looping the tethering component around "U-shaped" members of the anchoring component. The tethering component can slide along the anchoring component until reaching the end of the travel on the anchoring component. The clinician can exert tension on the tethering component until the tethering component is seated in the engagement area. This action can ratchet the tethering component and engage it to the engagement area of the anchoring component. Thereafter, the tethering component establishes a fixed range of longitudinal travel of the valve frame component relative to the anchoring component, and subsequently a proper position of the valve frame component in the anatomy, based only on the clinician placing the anchoring component into the aortic sinus region (the clinician can see under fluoroscopy and can "feel" the placement).

Thus, some embodiments disclosed herein advantageously provide a delivery device that has a reduced passing profile or cross section, thereby enabling delivery of a heart valve prosthesis in a safer, less invasive manner than traditional approaches. As such, open-heart surgery can be avoided because the heart valve prosthesis can be advanced to the heart using a catheter via an access point in the blood vessel, such as the femoral artery. This provides enormous benefits to patients, including less trauma to the patient, greater ease of recovery, and potentially fewer surgical risks, to name a few.

Further, although the in-series arrangement of the anchoring component and the valve frame component overcomes the challenge of creating a low-profile delivery device, the advantageous arrangement of the interconnection overcomes yet another critical challenge: how to optimally position the valve prosthesis within the native valve structure and to reliably anchor it in place. Indeed, some embodiments disclosed herein address this challenge and teach structures and methods for using a tethering component to operatively couple the anchoring component to the valve frame component in a delivery device.

The delivery device can comprise a proximal sheath that can house at least a portion of the anchoring component and a distal carrier assembly that can house at least a portion of the valve frame component. The tethering component can extend between the anchoring component and the valve frame component when the valve prosthesis is loaded onto the delivery device. The valve prosthesis can be released from the delivery device in a component-by-component manner that allows the clinician to maneuver and position the anchoring component first, followed by the valve frame component.

In some embodiments, the anchoring component can be coupled to an engagement member or grasper of the delivery device that allows the clinician to push or pull the anchoring component. The grasper can be released from engagement with the anchoring component when the anchoring component is properly seated relative to the native valve annulus.

In addition, in some embodiments, the distal carrier assembly of the delivery device can comprise two components or be referred to as a two-part nose cone assembly. In accordance with some embodiments is the realization that if a single tubular member or nose cone is used to sheath most of the valve frame component, various problems can arise due to the expansive force and corresponding compressive force required to maintain the valve frame component in its compressed configuration during delivery to a target valve structure. Because the delivery device can be quite long (for example, in some embodiments, up to about 4 to 6 feet or more, although the length can be less than 4, 3, or 2 feet), these forces can create a much stiffer distal section of the delivery device. Further, these forces can require a high degree of longitudinal force to release the valve frame component due to the high frictional forces due to the radial force of the valve implant.

Thus, the radial and frictional forces of such configurations can cause problems of matching handle actuation and make precise positioning of the distal end of the delivery device quite difficult. For example, the friction tends to be a variable friction that makes it difficult for a clinician to position the components of the valve prosthesis relative to each other, which can lead to unpredictable and/or imprecise component positioning or deployment. Thus, some embodiments herein include the realization that by separating the distal carrier or nose cone assembly into two components (such as a proximal and distal enclosure), the components can cover less surface area of the valve frame component, thus reducing the radial forces exerted on a single component and the resultant friction that would need to be overcome in order to actuate or release the valve frame component. As such, the problems associated with a single tubular member are much more manageable.

Additionally, in some embodiments, a two-part distal carrier assembly can also enable the clinician to release the valve frame component in an advantageous sequence. For example, during testing and development of the valve prostheses, deployment systems, and handle actuators disclosed herein, some embodiments demonstrate advantageous characteristics by permitting a distal end portion of the valve frame component to open first, before a proximal end portion of the valve frame component is released. In some embodiments, the valve frame component can have one or more anchors at its distal end portion that can supplement the outward expansive force (due to self-expansion of the valve frame component) and its resultant frictional engagement. By opening the distal end portion first (by actuation of distal nose cone or enclosure), the distal end portion can "flower" out and engage with the native valve structure to secure a longitudinal position of the valve frame component relative to the native valve structure. Thereafter, the self-expanding radial outward force of the valve frame component can cause the proximal end portion of the valve frame component to become disengaged and released from the proximal nose cone or enclosure.

Some embodiments can also provide self-aligning features to allow the components of the delivery assembly to be moved from a releasing state (where the components of the valve prosthesis are released from engagement with the delivery assembly) to a nested or stowed state in which outer surfaces of portions of the delivery assembly are aligned or in an abutting position at a seam. This alignment, abutment, or positioning can provide a smoother outer profile that can reduce the likelihood of having the delivery assembly snag or become entangled with the prosthetic valve after being released or with other vasculature as the delivery assembly is retrieved from the patient's vasculature.

For example, in some embodiments, the distal carrier or nose cone assembly can include an internal plunger or piston mechanism. The plunger mechanism can be compressed when the valve frame component is loaded into the delivery device. As the valve frame component is released, a spring of the plunger mechanism can push a plunger head to a predetermined position relative to the distal carrier assembly. In accordance with some embodiments, in the predetermined position, the plunger head can be exposed partially from the distal enclosure and be configured to engage with the proximal enclosure to align the proximal and distal enclosures relative to each other in an abutting relationship. The plunger head can therefore engage with both the proximal and distal enclosures to reduce the likelihood of catching or snagging of the delivery device with the prosthetic valve or other vasculature during retrieval of the delivery device. Additionally, such features can also aid in proximal retraction of the delivery device into an introducer sheath. Moreover, the plunger head can also provide a proximal surface that can be in contact with the distal end portion of the valve frame component and not catch or snag with the intricate mesh of the valve frame component, thereby ensuring that the valve frame component can flower open without catching on the delivery device. Accordingly, some embodiments can include one or more of these advantageous features that address the problem of having the valve prosthesis and/or the delivery device catch or snag on each other or surrounding anatomy.

Furthermore, due to the reduced cross-sectional profile of the delivery device, retrograde delivery of a valve prosthesis through the blood vessel (such as femoral artery in a transfemoral retrograde approach) can be possible with reduced risk of trauma to the surrounding vasculature. For example, retrograde delivery of the valve prosthesis through the femoral artery has been associated with aortofemoral artery injury and/or rupture, and carries a potential risk of stroke as the delivery involves crossing the aortic arch. However, the various features and advantages achieved using some embodiments disclosed herein provide a valve prosthesis and delivery device that minimizes damage along the delivery path of device while also minimizing the invasive nature of the implantation procedure.

Additional embodiments of the present devices and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded or omitted from any embodiment of the present disclosure. Additional aspects and advantages of the present disclosure are set forth in the following description and claims, particularly when considered in conjunction with the accompanying examples and drawings.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

Certain features of valve prostheses, delivery devices, actuation handles, other devices, systems, and methods which can be implemented with the valve prostheses, delivery devices, actuation handles, other devices, systems, and methods discussed in the present disclosure, can implement features of and/or be used in combination with other features of valve prostheses, delivery devices, actuation handles, other devices, systems, and methods described for example in International application Ser. No. PCT/US19/12406, entitled HEART VALVE PROSTHESIS, filed on Jan. 4, 2019, by Ji Zhang, Brandon G. Walsh, Cheng Yong Yang, Jinhua Zhu, and Dennis Michael McMahon, and in International application Ser. No. PCT/US19/12408, entitled PROSTHETIC HEART VALVE DELIVERY SYSTEM, filed on Jan. 4, 2019, by Ji Zhang, Brandon G. Walsh, and Cheng Yong Yang, the entirety of each of which is incorporated herein by reference.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 9E is an enlarged detail view of another valve prosthesis having a valve anchor with another link motion limiter, according to some embodiments.

DETAILED DESCRIPTION

Figure 1:
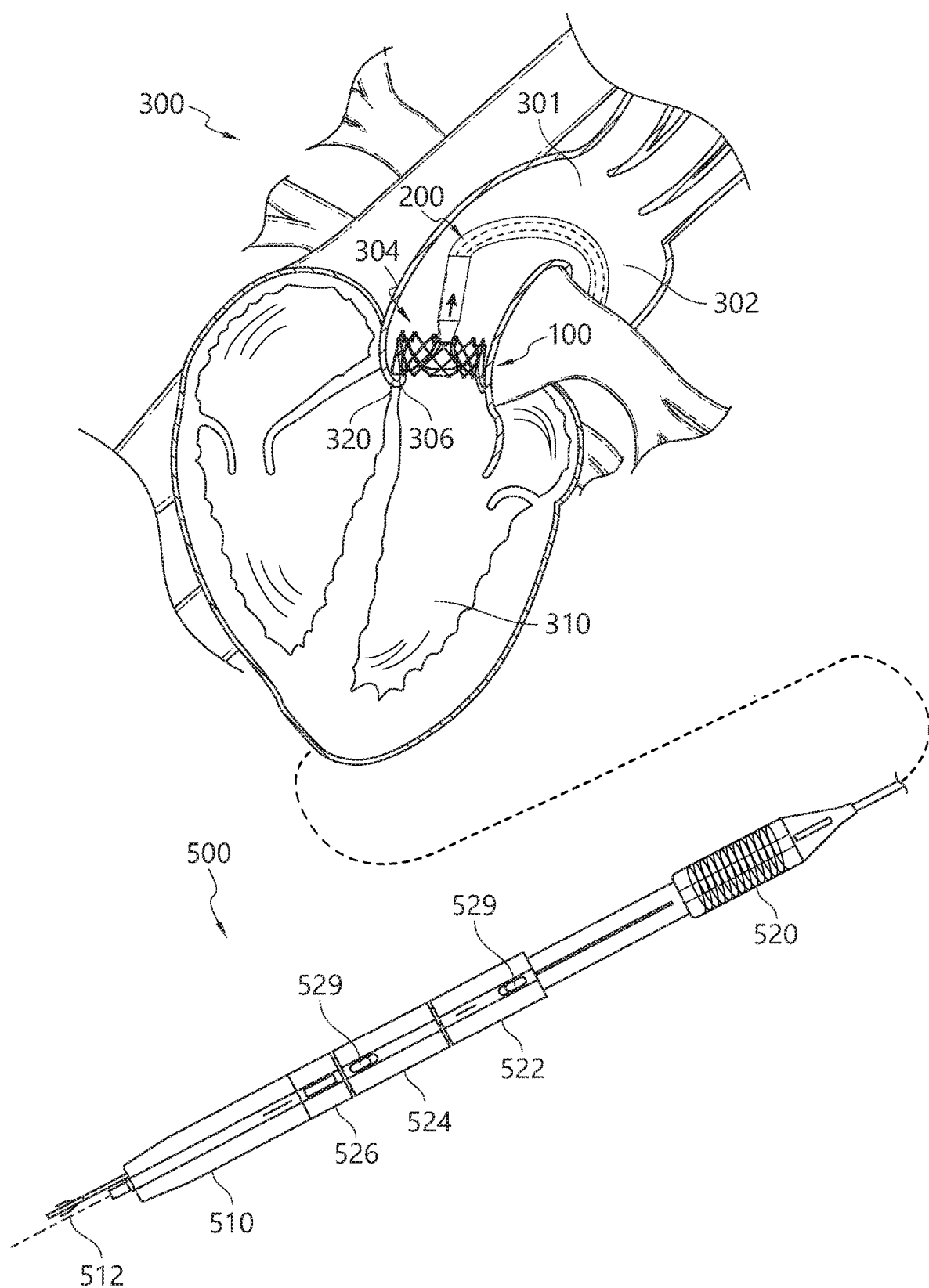
FIG. 1 illustrates delivery of a valve prosthesis using a valve delivery device in a transfemoral retrograde approach, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present disclosure sets forth specific details of various embodiments, it will be appreciated that the description is illustrative only and should not be construed in any way as limiting. Additionally, it is contemplated that although particular embodiments of the present disclosure may be disclosed or shown in the context of aortic valve prostheses, such embodiments may be used in other cardiac valve prosthesis applications. Furthermore, various applications of such embodiments and modifications thereto, which may occur to those who are skilled in the art, are also encompassed by the general concepts described herein.

Various embodiments will now be described more fully hereinafter. Such embodiments may, however, be embodied in many different forms and should not be construed as limited to the embodiments set forth herein; rather, these embodiments are provided so that this disclosure will be thorough and complete, and will fully convey its scope to those skilled in the art. Thus, one or more features shown or otherwise disclosed in an embodiment herein may be interchangeably used or incorporated into another embodiment that may not expressly show or disclose such feature(s). Further, one or more features shown or otherwise disclosed for an embodiment herein may be excluded from such embodiment, unless expressly indicated, using skill in the art.

As with all cardiac valves, a healthy aortic valve will open to allow blood flow and close to prevent backflow of blood. However, disease and dysfunction of the valve can result in regurgitation or decreased blood flow (stenosis). In such cases, a replacement aortic valve prosthesis must be used to perform the functions of a healthy aortic valve.

Minimally invasive surgical techniques are evolving, where a valve prosthesis can be introduced into a patient using a catheter that is introduced via a small incision that provides access to, for example, a femoral artery or directly to the heart. These implantation techniques have shown promising results in providing treatment options for patients who are poor open surgical candidates. Nevertheless, challenges still remain in such catheter-based delivery of prosthetic valves.

For example, in according with an aspect of at least one embodiment disclosed herein is the realization that advancing a conventional tubular delivery device through a vessel exerts stress against the vessel walls and carries the risk of damaging the vessel walls. Further, in according with an aspect of at least one embodiment disclosed herein is the realization that transcatheter prosthetic valves may not be able to treat patients with aortic regurgitation. Additionally, in according with an aspect of at least one embodiment disclosed herein is the realization that conventional prosthetic valves may be difficult to position, may require rapid ventricular pacing, and may have limited expansion. Accordingly, implantation and use of conventional prosthetic valves may result in complications, such as vascular damage, moderate to severe paravalvular leakage, valve thrombosis/migration, coronary artery blockage, and excessive stress due to excessive radial force.

The present disclosure describes various aspects of heart valve prostheses that can be delivered to a defective heart valve in a patient. The valve prostheses can comprise at least one valve anchor or clasper, which is movably connected, movably attached, flexibly connected, displaceably connected, linked, or coupled to a radially-expandable valve support or frame. The valve frame can comprise prosthetic valve leaflets or cusps and provide the functionality of the native heart valve. Certain features of valve prostheses, which can be implemented with the prostheses discussed in the present disclosure, are also further described for example, in U.S. Pat. No. 8,366,768, the entirety of which is incorporated herein by reference.

Thus, the present disclosure provides a variety of features that can be optionally incorporated or excluded from any of the embodiments explicitly discussed or illustrated herein. These modifications and combinations of features can be performed by a person of skill to achieve advantages and benefits discussed herein. Further, certain modifications or combinations are indicated or suggested herein, but it is contemplated that a person skill can implement or exclude certain aspects or features disclosed herein in developing a suitable embodiment or implementation of these teachings. Advantageously, various embodiments described herein allow for treating patients with aortic regurgitation, permit precise axial, angular, and radial positioning of the valve prosthesis, minimize valve migration and paravalvular leakage while avoiding damage to the valve annulus, minimize the need for a pacemaker, and decrease the likelihood of blocking the coronary artery.

Some of these features and benefits of the heart valve prosthesis are illustrated with respect to FIGS. 1-5. FIG. 1 illustrates the use of the delivery device 200 in a human heart 300. The heart 300 can comprise an aorta 301 having an aortic arch 302 and an aortic valve 304. The aorta valve 304 can comprise a plurality of native valve leaflets 306 and separate the aorta 301 from the left ventricle 310. In accordance with some embodiments, the delivery device 200 can be advanced retrograde through the aorta 301 until reaching and being positioned through the native valve leaflets 306 of the aortic valve 304.

Figure 2:
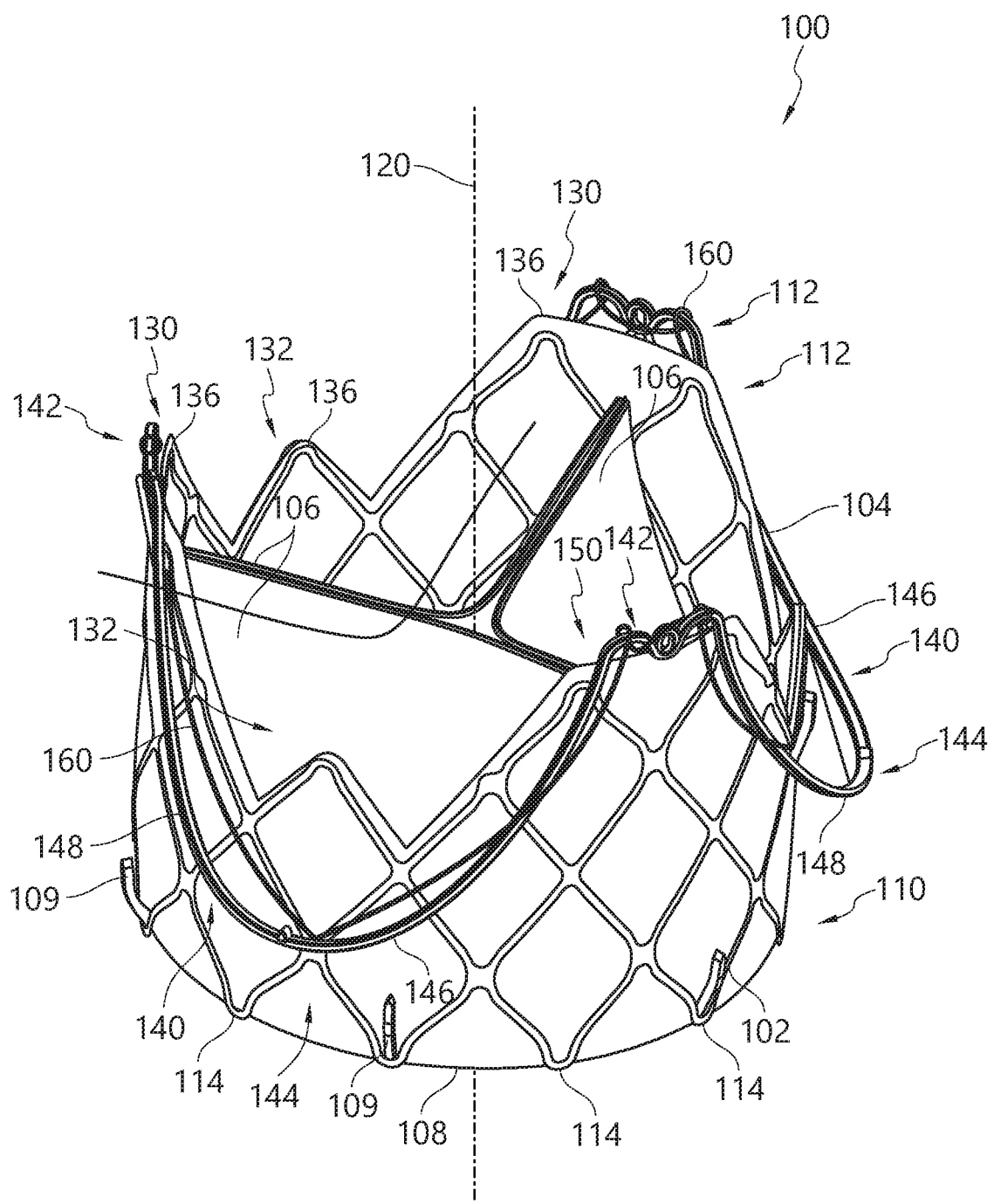
FIG. 2 shows a valve prosthesis, according to some embodiments.

With reference to FIGS. 1 and 2, during delivery of the valve prosthesis 100 to the native valve site, the valve anchor 104 and the support frame 102 can be positioned in tandem, as an axially displaced unit (with or without partial or full overlapping between the anchor and the frame) along the longitudinal axis of the delivery device 200. This configuration, as opposed to a concentric arrangement, can allow a more radially compact configuration of the components of the valve prosthesis 100, creating a much smaller cross-section and facilitating a catheter-based delivery. This can improve the flexibility of the delivery device 200, enabling the delivery device 200 to be advanced over a guidewire through the tortuous geometries of the circulatory system, and in particular, the aortic arch 302. Indeed, even with guidewire-directed delivery devices, the aortic arch 302 represents a difficult obstacle due to its sudden and high-degree of curvature. Often, this is a limiting constraint for some surgeries or delivery devices. However, in accordance with the various benefits and advantages of some embodiments disclosed herein, as illustrated in FIG. 1, the delivery device 200 can be advanced over the aortic arch 302 to a target location in the region of the aortic valve 304.

As shown in FIG. 1, once the valve anchor 104 is in the desired position, the support frame 102 can be released from the distal carrier assembly and expanded into apposition with the native valve leaflets 306 and the internal aspects of the valve anchor 104, thus sandwiching the native valve leaflets 306 between the support frame 102 and the valve anchor 104. Advantageously, by sandwiching the native valve leaflets 306 between the support frame and the valve anchor, the valve prosthesis 100 can have reduced reliance on radial force retention. Further, by sandwiching the native valve leaflets 306 between the support frame and the valve anchor, the likelihood of the native valve leaflets 306 blocking the opening of the coronary artery is reduced, which may be beneficial for patients with low coronary ostia distance, and in patients with an existing valve prosthesis, who may need a new valve prosthesis inside the existing valve prosthesis (valve-in-valve application). The support frame and the valve anchor can thus expand into contact with the aortic valve 304, exerting a chronic outward force against the native valve leaflets 306 and aortic valve annulus 320. Thereafter, the prosthetic valve leaflets of the prosthesis 100 can begin to function in the manner desired and provide the same operation as a native valve.

According to some embodiments, the present disclosure also provides a handle actuator that can be used to control the operation of the presently disclosed delivery device and allow a clinician to reliably and accurately control the delivery of the valve prosthesis. FIG. 1 illustrates features and operation of the handle actuator, according to some embodiments, for delivering a valve prosthesis using a handle actuator 500.

FIG. 1 illustrates the handle actuator 500, which can control one or more functions of a delivery device (e.g., the delivery device 200 discussed herein) for delivering of a valve prosthesis (e.g., the heart valve prosthesis 100 discussed herein). The handle actuator 500 can comprise a plurality of actuators or movable elements, such as knobs or buttons. The movable elements can permit a clinician to control one or more operations of the delivery device 200. The handle actuator 500 can comprise a control handle 510 having a longitudinal axis 512. The handle actuator 500 may be also referred to as a control unit. In some embodiments, the handle actuator 500 may be coupled to the second core member 222 (shown, e.g., in FIGS. 3 and 5). The control handle 510 can support the actuators and be held by the clinician during the procedure.

In some embodiments, as illustrated in FIG. 1, the handle actuator 500 can comprise a first movable element 520, a second movable element 522, a third movable element 524, and a fourth movable element 526. The first movable element 520 can be used to steer the delivery device 200, the second movable element 522 can be used to release the valve anchor, the third movable element 524 can be used to release nosecone or valve frame, and the fourth movable element 526 can be used as a nose cone toggle lock. The first movable element 520, the second movable element 522, the third movable element 524, and the fourth movable element 526 may be also referred to as the first control element 520, the second control element 522, the third control element 524, and the fourth control element 526.

Optionally, in some embodiments, one or more of the movable elements, such as the second movable element 522 and/or the third movable element 524, can include a button or slider safety switch 529 that prevent the unintentional rotation of the moveable elements. The safety switch 529 can be configured as resilient button or slider mechanisms that can be actuated to release a lock that provides resistance to rotational or translational movement of the respective movable element. In some embodiments, the movable elements can have a raised feature that provides a visual indication of rotation and facilitates tactile engagement and actuation by the clinician. Other features of the handle actuator 500 and methods for operating the handle actuator 500 are discussed and illustrated in FIGS. 13A-13H of U.S. Patent Application No. 62/781,537, filed on Dec. 18, 2018, the entirety of which is incorporated herein by reference.

Referring now to FIG. 2, a valve prosthesis 100 and components thereof are shown in various configurations. The valve prosthesis 100 can be delivered to a patient using a suitable delivery device, including embodiments of the delivery devices disclosed herein. The valve prosthesis 100 can comprise a support frame 102 and an anchoring component or valve anchor 104 to which the support frame 102 is movably connected, movably attached, flexibly connected, displaceably connected, linked, or coupled.

The valve prosthesis 100 can be configured such that components of the valve prosthesis 100 to be advanced in series while still being movably connected, movably attached, flexibly connected, displaceably connected, linked, or coupled to each other, thereby minimizing a passing profile or cross section of the delivery system. The interconnection of components of the valve prosthesis 100 can allow different degrees of motion and can be set into an engaged or retained position that provides a limited range of motion. In some embodiments, the engaged position can also provide a preset relative positioning of the components of the valve prosthesis 100 to facilitate proper placement and release of the valve prosthesis 100. Additionally, some embodiments can provide a clinician with a high degree of control and enhance the maneuverability of the valve prosthesis 100 when implanting the valve prosthesis 100 at the target location.

In some embodiments, the valve anchor 104 can be coupled to the support frame 102 when the support frame 102 is in the compact configuration prior to delivery and expansion. In some embodiments, the valve anchor 104 is not fixed to the support frame 102. Further, the valve anchor 104 can be separate from the support frame 102 or formed separately from and later coupled to the support frame 102. Thus, although a least a portion of the valve anchor 104, e.g., the anchoring leg, may be in contact with or otherwise reversibly attached or connected to the support frame 102, no part of the valve anchor 104 is fixed, e.g., welded or otherwise irreversibly adhered, to the support frame 102. Alternatively stated, the valve anchor 104, which may be in contact with or otherwise reversibly attached to the support frame 102, is not irreversibly fixed to the support frame 102.

Further, upon reaching the target location, the valve anchor 104 can be movably coupled to the support frame 102 in a manner that prevents the entire valve anchor 104 from being radially displaced from the support frame 102 when the valve anchor 104 is initially expanded. For example, portions of the valve anchor 104 can be radially displaced from the support frame during initial "landing" of the valve anchor 104 against the native valve structure at the target location. In some embodiments, the support frame 102 can be deployed or expanded within the native heart valve structure, and the valve anchor 104 can become sandwiched between the support frame and the native valve tissue, becoming at least partially, and possibly fully, immobilized. The valve anchor 104 can function to hold the expanded support frame 102 in place within the native valve structure.

Optionally, the support frame 102 may be referred to as a valve frame or valve support frame. FIG. 2 illustrates the support frame 102 aligned with and expanded within the valve anchor 104, in a configuration that is achieved when the prosthesis 100 is released and expanded within the native valve structure. The native valve structure includes the valve annulus or leaflets. This expanded configuration, serves to secure the valve prosthesis 100 within the native valve annulus by engaging the native valve structure. In some embodiments, the expanded configuration of the valve prosthesis 100 may reduce reliance on securing the valve prosthesis 100 with radial force exerted by the support frame 102 and the valve anchor 104 via the sandwiching or compression of the native valve leaflets between the support frame 102 and the valve anchor 104 of the valve prosthesis 100. Further, as discussed further herein, during implantation of the valve prosthesis 100, the support frame 102 and the valve anchor 104 can be movable relative to each other in expanded and/or compressed states in order to facilitate proper positioning of the prosthesis 100 relative to the native valve annulus and surrounding structures. Indeed, various advantages made possible by the prosthesis 100 and delivery device disclosed herein allow a clinician to achieve a higher degree of precision in placing the prosthesis 100, as well as making such increased precision easier to achieve.

Referring to FIG. 2, the support frame 102 can comprise an outer or external surface and defines a central orifice about a longitudinal axis 120. The longitudinal axis 120 corresponds to an inflow-outflow axis of the prosthesis 100. In some embodiments, the valve prosthesis 100 further comprises a plurality of prosthetic valve leaflets or cusps 106 that are coupled to the support frame 102. The support frame 102 can provide a structural support for the valve leaflets 106. The valve leaflets 106 can have surfaces defining a reversibly sealable opening for unidirectional flow of a liquid through the prosthesis 100. The prosthesis 100 can include three valve leaflets 106 for a tri-leaflet configuration. As appreciated, mono-leaflet, bi-leaflet, and/or multi-leaflet configurations are also possible. For example, the valve leaflets can be coupled to the support frame 102 to span and control fluid flow through the lumen of the prosthesis 100. The prosthetic leaflets 106 can comprise one or more synthetic materials, engineered biological tissues, biological valvular leaflet tissues, pericardial tissues, cross-linked pericardial tissues, aortic root tissue, chemically or biologically processed/treated tissue, or combinations thereof. In some embodiments, the pericardial tissue is selected from but not limited to the group consisting of bovine, equine, porcine, ovine, human tissue, or combinations thereof.

Furthermore, in some embodiments, the valve prosthesis 100 can comprise a sealing component or membrane 108 that can be attached to an inside surface, an outside surface, and/or enclose the support frame 102, such as by being laminated onto inner and outer surfaces of the support frame 102. Thus, the valve leaflets 106 can be coupled to the support frame 102 and/or the membrane 108. In some embodiments, the membrane 108 can restrict blood flow in areas around the valve leaflets 106 so that blood flow occurs only between the valve leaflets 106 through the lumen of the prosthesis 100, as in a healthy native heart valve.

The support frame 102 and/or the valve anchor 104 can comprise a braided frame, a wire frame, or a laser-cut frame (e.g., laser-cut tubular mesh), as shown in FIG. 2. In some embodiments, the support frame 102 and/or the valve anchor 104 can comprise a shape-memory metal, which can change shape at a designated temperature or temperature range or by inducing stress. Alternatively, the self-expanding frames can include those having a spring-bias. The material from which either the support frame 102 and/or the valve anchor 104 is fabricated can allow the support frame 102 and/or the valve anchor 104 to automatically expand to its functional size and shape when deployed but also allows the support frame 102 and/or the valve anchor 104 to be radially compressed to a smaller profile for delivery through the patient's vasculature. Examples of suitable materials for self-expanding components described herein (e.g., support frames, valve anchors, locking members) include, but are not limited to, medical grade nickel titanium alloys, tantalum, platinum alloys, niobium alloys, cobalt alloys, alginate, or combinations thereof. Shape memory alloys having superelastic properties generally made from ratios of nickel and titanium, commonly known as Nitinol, are preferred materials. In some embodiments, self-expanding components described herein can include materials including, but not limited to shape memory plastics, polymers, and thermoplastic materials which are inert in the body. In an alternative embodiment, either the support frame 102 and/or the valve anchor 104 is not self-expanding, and may be expanded, for example, using a balloon catheter as is well known in the art. Examples of suitable materials for components described herein include, but are not limited to, stainless steel and titanium. Optionally, either the support frame 102 and/or the valve anchor 104 can comprise radiopaque materials to allow visualization under fluoroscopy or other imaging techniques.

Optionally, the support frame 102 can comprise one or more hooks 109 that can engage with tissue of the native valve annulus, the aortic root, or any other portion of the native valve when the support frame 102 is expanded within the native valve annulus. The hooks 109 can be engaged with the native valve annulus to secure the prosthesis 100 and mitigate any downstream or antegrade migration of the prosthesis 100 during operation.

The support frame 102 can comprise a first end portion 110 and a second end portion 112. The first end portion 110 can be positioned upstream of the second end portion 112 when the prosthesis 100 is released within the native valve annulus. As illustrated in FIG. 2, the first end portion 110 of the support frame 102 can be shaped as a generally flat end of a cylinder, where first apices 114 of the support frame 102 lie generally in a common plane, which can be oriented substantially perpendicular relative to a longitudinal axis 120 of the prosthesis 100. Further, the second end portion 112 can be shaped to include a series of peaks 130 and valleys 132, where second apices or minor peaks 136 of the support frame 102 collectively form contours of the peaks 130 and valleys 132. The peaks 130 and valleys 132 of the second end portion 112 can be positioned downstream of the first end portion 110 when the prosthesis is seated within the native valve annulus.

In accordance with some embodiments, the prosthetic leaflets 106 can be coupled relative to the support frame 102 at locations circumferentially aligned with the peaks 130 of the second end portion 112, as shown in FIG. 2. In some embodiments, the prosthetic leaflets 106 can be coupled to the membrane 108 using ultra-high molecular weight polyethylene sutures. This unique configuration can advantageously enable the prosthesis 100 to more fully approximate the native valve structures, permit a more natural blood flow without limiting or otherwise constraining movement of the valve leaflets 106, and more seamlessly integrate with surrounding architecture of the heart. In some embodiments, the prosthetic leaflets 106 can comprise features, including, but not limited to, planar features, flat features, three-dimensional features, Bezier curves, or other suitable shapes. Optionally, the prosthetic leaflets 106 can be shaped through fixation on a leaflet-shaped mandrel.

The valve anchor 104 can comprise at least one U-shaped member, valve clasper, sinus locator, valve positioner, or valve hanger 140 that extends about a longitudinal axis of the valve anchor 104. As illustrated in FIG. 2, the valve anchor 104 can comprise a plurality of lobes or U-shaped members 140, such as three U-shaped members 140, but can have fewer or more. In some embodiments, U-shaped members 140 can be configured to engage with or fit inside the posterior aortic sinus, the left aortic sinus, and the right aortic sinus of a native aortic valve. The U-shaped members 140 can each have a peak portion 142 and a base portion 144. The U-shaped members 140 can each comprise first and second legs 146, 148. The first and second legs 146, 148 of the adjacent U-shaped members 140 can be interconnected at the peak portions 142 thereof. Further, the U-shaped members 140 can comprise shapes other than a U-shape, such as a wave-shape, V-shape, W-shape, or zig-zag. Optionally, multiple valve anchors 104 can each comprise one or more U-shaped members 140, wherein the multiple valve anchors 104 cooperatively engage with the aortic sinus to anchor the valve prosthesis as described herein.

The valve prosthesis 100 can include a link mechanism that interconnects the support frame 102 to the valve anchor 104. The link mechanism can comprise a single, continuous strand of material or multiple, independent strands of material that interconnects the support frame 102 to the valve anchor 104. Further, the link mechanism can attach in a sliding, engaged, or fixed manner to one or more locations on the support frame 102 and/or on the valve anchor 104.

In accordance with some embodiments, the valve anchor 104 may optionally define one or more engagement areas in one or more portions of the valve anchor 104, where a link mechanism may engage with the one or more engagement areas to restrict relative motion between the support frame 102 and the valve anchor 104.

For example, at the interconnection of the respective peak portions, the valve anchor 104 can define an engagement area 150. The engagement area 150 may also be referred to as a peak portion engagement area.

As illustrated in FIG. 2, the support frame 102 can be flexibly coupled to the valve anchor 104 via one or more tethering components or link mechanisms 160. The link mechanism 160 can be coupled to the support frame 102 and to the valve anchor 104, permitting relative movement between the support frame 102 and the valve anchor 104. However, the link mechanism 160 can be configured to limit relative movement between the support frame 102 and to the valve anchor 104. In some embodiments, the engagement area 150 of the valve anchor 104 can be used to further restrict relative motion of the support frame 102 with respect to the valve anchor 104 when the link mechanism 160 is engaged in the engagement area 150, as discussed herein.

The valve anchor 104 can thus be coupled to the support frame 102 to permit the valve anchor 104 to be moved axially or longitudinally relative to the support frame 102 while still remaining coupled to the support frame 102. This advantageous feature of some embodiments can allow a clinician to independently position the valve anchor 104 relative to the support frame 102. For example, in a transcatheter aortic valve replacement, the clinician can independently position the valve anchor 104 in order to fit the base portions 144 of the valve anchor 104 into the aortic sinus. Portions of the of aortic sinus may include the posterior aortic sinus, the left aortic sinus, and/or the right aortic sinus, of a native aortic valve. In some embodiments, the valve anchor 104 can rotate to be aligned in the respective aortic sinuses. In some embodiments, the interconnection of the valve anchor 104 to the support frame 102 can allow the valve anchor 104 to self-rotate to be aligned in the aortic sinus. Thereafter, with the valve anchor 104 "landed" in the respective aortic sinuses, the interconnection of the valve anchor 104 to the support frame 102 further enables the support frame 102 to translated along the longitudinal axis 120 of the valve prosthesis 100. In some embodiments, during the delivery procedure, the valve anchor 104 can be moved at least axially from a proximal position relative to the support frame 102, to a distal position relative to the support frame 102, or from either of such positions to a position in which the support frame 102 at least partially longitudinally overlaps with or is concentric within the valve anchor 104. A range of various positions are illustrated, for example, in FIGS. 11A-11F of U.S. Patent Application No. 62/781,537, filed on Dec. 18, 2018, the entirety of which is incorporated herein by reference.

For example, when the support frame 102 is nested within the valve anchor 104, as shown in FIG. 2, the base portions 144 of the valve anchor 104 can be longitudinally spaced apart from first end portion 110 of the support frame 102 along the longitudinal axis 120 at a distance which is about 10% to about 100%, about 25% to about 75%, about 33% to about 100%, about 33% to about 66%, about 25% to about 75%, about 50% to about 75%, or about 60% to about 70% of a length of the support frame 102. In some embodiments, the support frame 102 can be contained or otherwise fully overlapping the valve anchor 104. In some embodiments, the support frame 102 can have minimal or no overlap with the valve anchor 104. The support frame 102 can move along the longitudinal axis 120 to overlap the valve anchor 104 by about 10% to about 100%, about 25% to about 75%, about 33% to about 100%, about 33% to about 66%, about 25% to about 75%, or about 50% to about 75% of the length of the support frame 102. In accordance with some embodiments, the U-shaped members 140 of the valve anchor 104 can be in nested positions within the aortic sinuses, and the base portions 144 of the valve anchor 104 can be about longitudinally adjacent to, coplanar with, or spaced apart from the first end portion 110 of the support frame 102. For example, the valve anchor 104 can be in a nested position when at least one base portion 144 of the valve anchor 104 is in contact with or adjacent to the basal attachments of the native aortic valvar leaflets. Further, the first end portion 110 of the support frame 102 can be longitudinally adjacent to, coplanar with, or spaced apart from the native valve structure (or a virtual ring formed by the basal attachments of the native aortic valvar leaflets) or with the ventriculo-aortic junction.

The link mechanism 160 can allow rotational and longitudinal movement of the valve anchor 104 relative to the support frame 102. Thus, despite the presence of the link mechanism 160, the valve anchor 104 can move rotationally with respect to the support frame 102. Further, in some embodiments, the link mechanism 160 can be fixedly attached or coupled to the support frame 102 and fixedly or slidably attached to the valve anchor 104. When the support frame 102 is moved relative to the valve anchor 104, the link mechanism 160 can slide along the U-shaped members 140. In some embodiments, the U-shaped members 140 have a generally arcuate or convex shape (as illustrated with the U-shaped members of FIG. 2) that allows unrestricted movement of the link mechanism 160 along the geometry of the first and second legs 146, 148 of the U-shaped members 140. When the link mechanism 160 is allowed to slide along the first and second legs 146, 148 of the U-shaped members 140, the valve prosthesis 100 can be in a position referred to as a "slidable" state. In the slidable state, the range of longitudinal and/or rotational movement of the support frame 102 relative to the valve anchor 104 is variable and may be its greatest because the link mechanism 160 can move along the first and second legs 146, 148 of the U-shaped members 140.

In some embodiments, the link mechanism 160 can be fixedly attached or coupled to the support frame 102 and fixedly attached to the valve anchor 104. When the support frame 102 is moved relative to the valve anchor 104, the link mechanism 160 can stretch, flex, deform elastically and/or plastically. As the link mechanism 160 deforms, the range of longitudinal and/or rotational movement of the support frame 102 relative to the valve anchor 104 is variable as allowed by the deformation of the link mechanism 160.

In some embodiments, the link mechanism 160 can have multiple link members, where each link member is coupled to and intermittently spaced about a circumference of the support frame 102. Each link member may be slidably coupled to a respective one of the U-shaped members 140. Further, the link mechanism 160 can have multiple link members that are coupled together in an end-to-end manner. Moreover, the link mechanism 160 can have multiple link members that are individually coupled at one and to the support frame 102 and at another and to the valve anchor 104. Each of the link members can be slidable along the valve anchor 104, as disclosed similarly herein and not described again herein for brevity.

As noted above, however, the valve anchor 104 can also comprise engagement areas 150 that can engage with the link mechanism 160 in order to restrict relative motion between the support frame 102 and the valve anchor 104. The engagement areas 150 can include one or more local concavities or other geometric shapes that can engage or trap the link mechanism 160 once the link mechanism 160 passes into the engagement area 150. FIGS. 6A-6G illustrate various embodiments of engagement areas 150 that can be used to permit the slidable link mechanism 160 to enter into the engagement area 150, but restrict the link mechanism 160 from exiting the engagement area 150.

Figure 3:
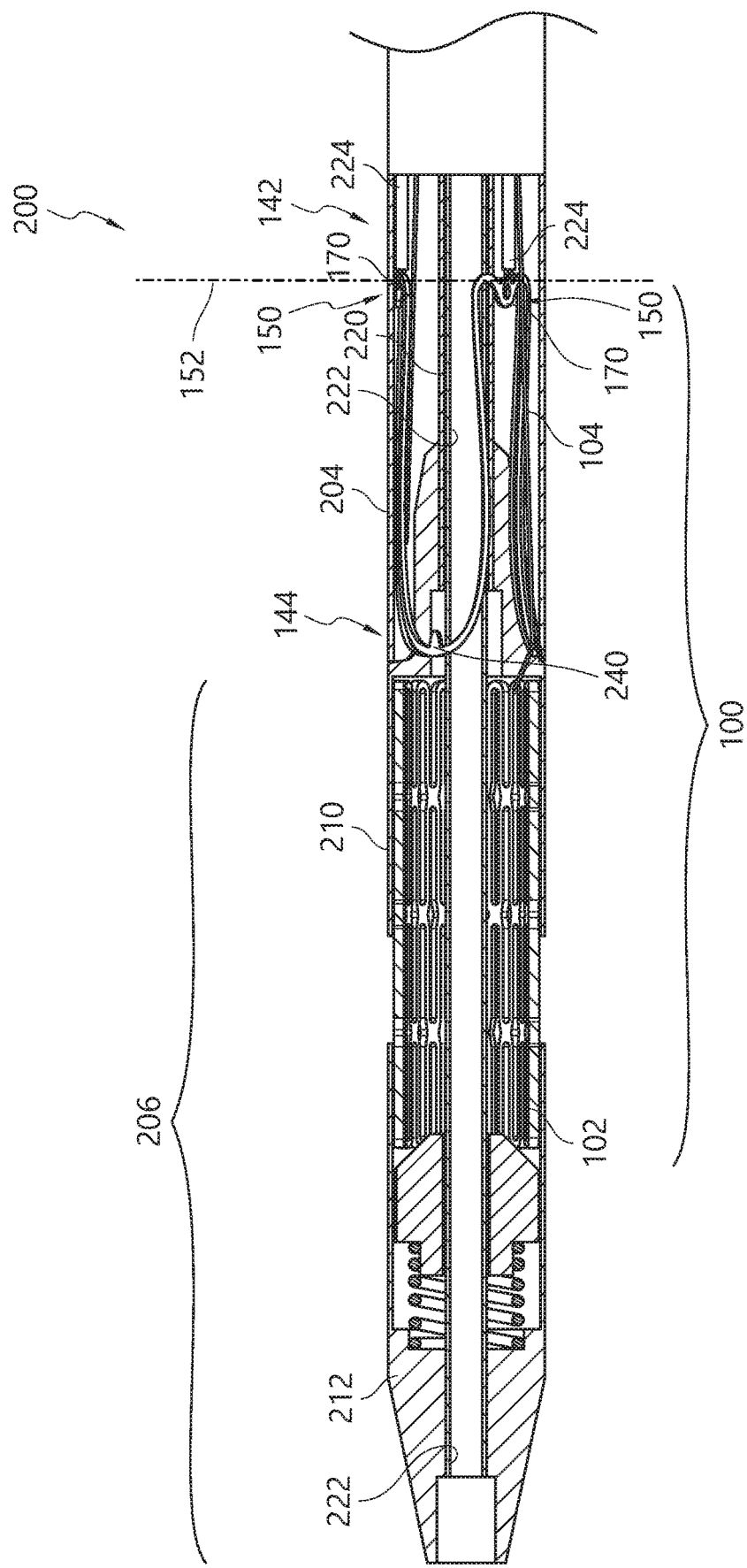
FIG. 3 is a side cross-sectional view of the valve prosthesis of FIG. 2 loaded onto a valve delivery device, according to some embodiments.

Referring now to FIG. 3, a side cross-sectional view is provided of the valve prosthesis 100 loaded onto the delivery device 200, according to some embodiments. Among the many features illustrated in FIG. 3, FIG. 3 shows that a proximal enclosure 210 of delivery device 200 can extend over both the valve anchor 104 and the support frame 102. Thus, in accordance with some embodiments, in the compressed or delivery configuration shown in FIG. 3, the link mechanism (not shown) can extend between the valve anchor 104 and the support frame 102 and be at least partially enclosed within the proximal enclosure 210 (depending on the attachment point of the link mechanism with the support frame 102 and the longitudinal extent of the proximal enclosure 210).

In addition, FIG. 3 illustrates that the valve anchor 104 can comprise a link motion limiter 240. The link motion limiter 240 can provide an enlarged profile of the wireframe structure of the valve anchor 104 so as to restrict or prevent motion of the link mechanism as the link mechanism slides along the U-shaped member of the valve anchor 104.

In alternative embodiments of the delivery device 200, the valve anchor 104 and the support frame 102 can both be enclosed within the proximal sheath component 204 prior to and during delivery prior to releasing the valve anchor 104. For example, in some embodiments, the valve anchor 104 can be distal to the support frame 102 wherein the valve anchor 104 is near the distal end of the proximal sheath component 204 and the support frame 102 can be approximately adjacent to the valve anchor 104 (in a serial configuration) and is proximal to the valve anchor 104. In some embodiments of the delivery device 200, the valve anchor 104 and the support frame 102 can both be enclosed within the proximal sheath component 204, with the support frame 102 near the distal end of the proximal sheath component 204 and the valve anchor 104 being approximately adjacent to the support frame 102 and proximal to the support frame 102.

Further, in alternative embodiments of the delivery device 200, the valve anchor 104 can be enclosed within the distal carrier assembly 206 and the support frame 102 can be enclosed within the proximal sheath component 204 prior to and during delivery of the valve prosthesis. For example, in some embodiments of the delivery device 200, both the valve anchor 104 and the support frame 102 can be enclosed within the distal carrier assembly 206 and the support frame 102 can be enclosed within the proximal sheath component 204 prior to and during delivery of the valve prosthesis. In this configuration, the valve anchor 104 and the support frame 102 can be approximately adjacent to one another (in a serial configuration) and the valve anchor 104 can be positioned proximal to the support frame 102. Other details of delivery devices and prostheses are provided in U.S. Patent Application No. 62/781,537, noted above and incorporated herein by reference.

In addition, FIG. 3 illustrates that an anchor retention component 170 can be used to engage the engagement areas 150 of the valve anchor 104 with the control member or a grasper 224 to facilitate movement and control of the positioning of the valve anchor 104 during delivery. As discussed with regard to FIGS. 7G-7I of U.S. Patent Application No. 62/781,537, noted above, this engagement can maintain the engagement areas 150 in a common plane 152, oriented generally perpendicular relative to the longitudinal axis of the delivery device 200.

Figure 4:
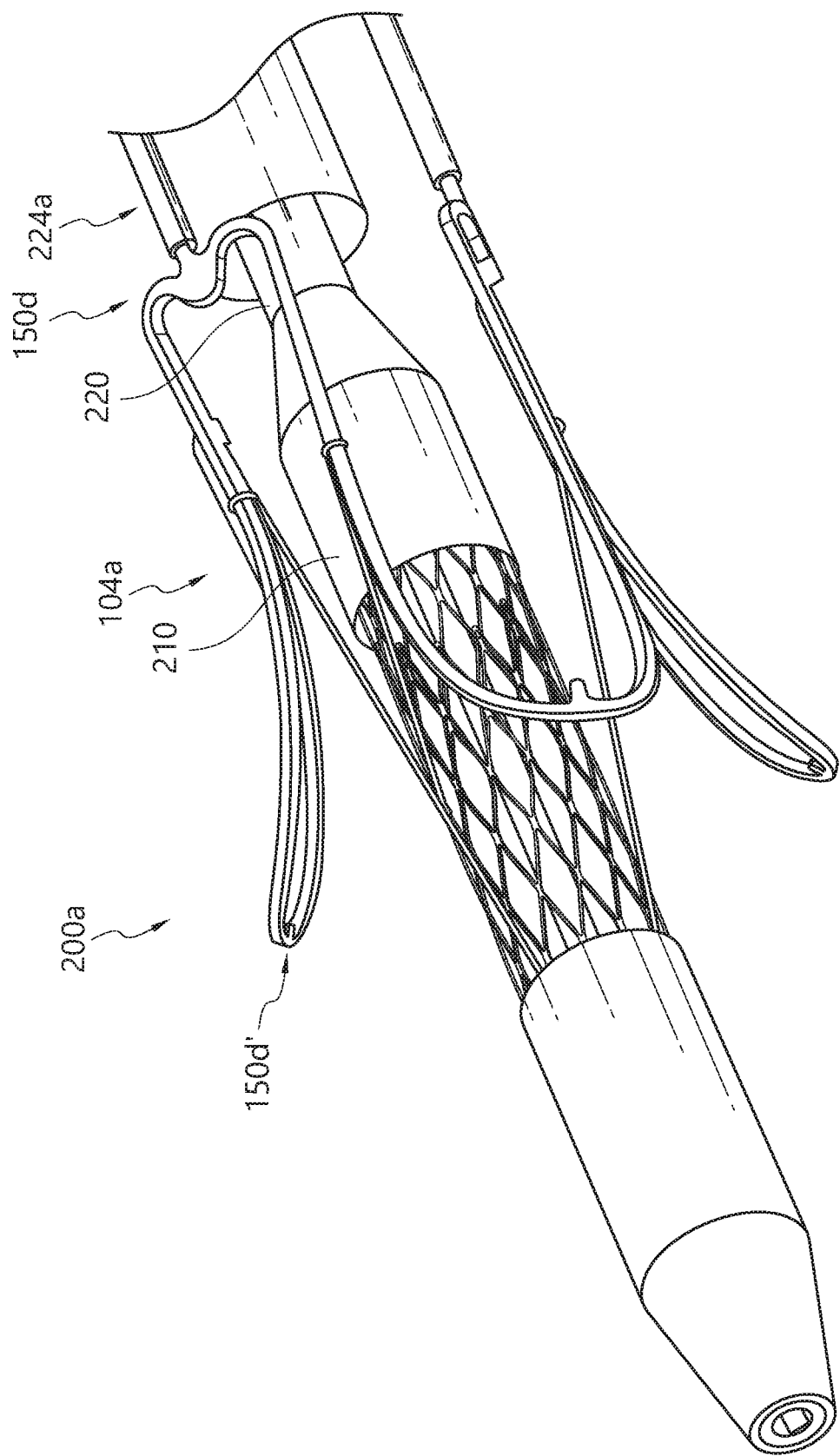
FIG. 4 is a perspective view the valve delivery device of FIG. 3 showing a grasper mechanism for engaging a valve anchor, according to some embodiments.

FIG. 4 illustrates aspects of the delivery device 200a, according to at least one embodiment. These figures do not illustrate all of the components of the delivery device that can be incorporated into an embodiment. However, the features illustrated in these figures can be incorporated into embodiments of the delivery device to facilitate engagement with the valve anchor and/or facilitate delivery and control of the valve anchor during implantation and release of the valve anchor at the target location.

For example, FIG. 4 illustrates an embodiment of a delivery device 200a that comprises a grasper mechanism. The grasper mechanism can be used to securely couple a portion of the valve anchor with the delivery device to permit the clinician to control movement, operation, and deployment of the valve anchor. The grasper mechanism can engage one or more portions or structures of the valve anchor using a variety of coupling mechanisms, which can use attachment means including mechanical engagement, dissolvable structures, chemically reactive degradable structures, electrolytically degradable structures, and the like.

In some embodiments, the grasper mechanism can be a tubular grasper mechanism. The delivery device 200a, shown in FIG. 4, can comprise a grasper 224a that can engage with and control the longitudinal position of the valve anchor 104a. The grasper 224a of the delivery device 200a can comprise an engagement wire that is movable within a lumen of a tubular enclosure. The valve anchor 104a can be configured to comprise a clasper tang extending from an engagement area 150d or 150d' of the valve anchor 104a. The engagement wire can comprise a distal end portion that includes pins, ridges, or protrusions that can be coupled to the engagement structure of the clasper tang at the engagement area of the valve anchor 104a. When engaged together, the engagement wire and the clasper tang can be proximally drawn into the lumen of the tubular enclosure, which secures the engagement wire and the clasper tang relative to each other in both radial and longitudinal directions. However, when the engagement wire and the clasper tang are moved outside of the lumen of the tubular enclosure, the engagement wire and the clasper tang can be disengaged as the valve anchor 104a and the clasper tang expand radially, thereby disengaging the clasper tang from the engagement wire. These and other features are discussed in U.S. Patent Application No. 62/781,537, noted above and incorporated herein by reference.

During use, after the valve anchor has been released from within the proximal sheath and after the valve anchor and the valve frame have been released from the delivery device, the delivery device can be configured to be compactly reassembled and withdrawn into the introducer sheath in order to minimize any damage to the blood vessel through which the delivery device was advanced.

Figure 5A:
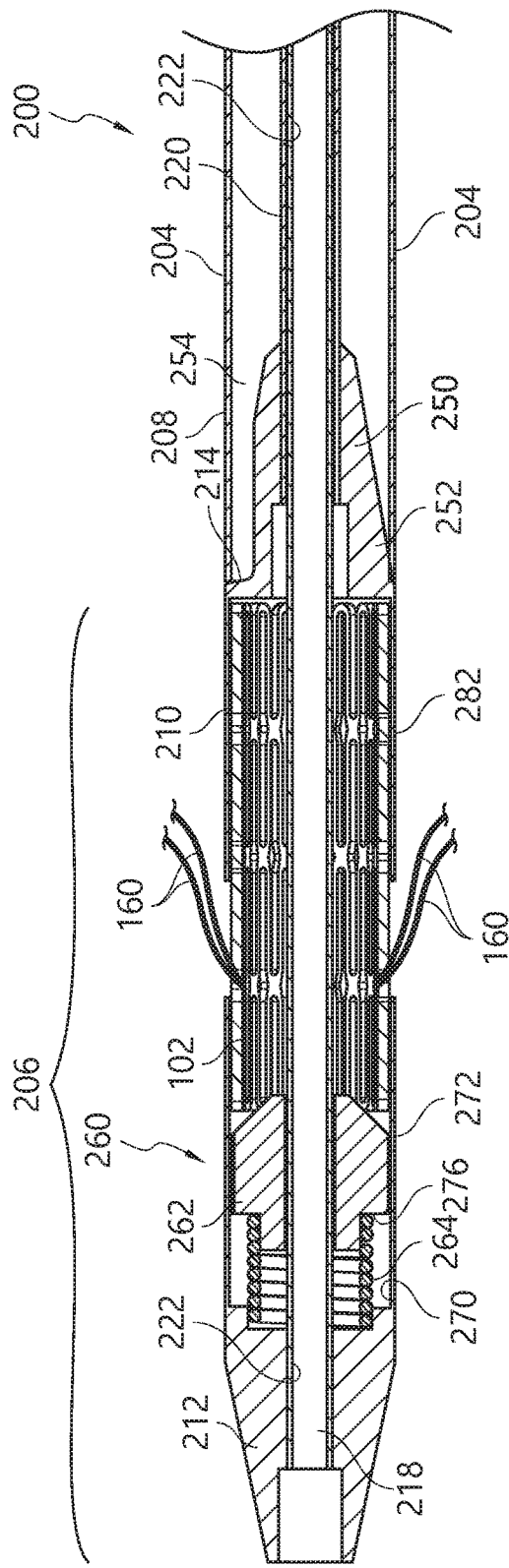
FIGS. 5A and 5B are side cross-sectional views illustrating operation of a distal carrier assembly of the valve delivery device of FIG. 3 with a nose cone protector, according to some embodiments.

For example, in at least one embodiment, as illustrated in FIG. 5A, the proximal enclosure 210 can comprise a proximal section 250 to facilitate realignment (e.g., radial realignment) of the distal end portion 208 of the proximal sheath component 204 with the proximal enclosure 210.

As illustrated in FIG. 5A, the proximal section 250 can be coupled to the core member 220. Further, the proximal section 250 can optionally be conical or tapered in a proximal direction and/or have circumferential nodes 252 and/or circumferential cavities 254 that can facilitate realignment of the proximal sheath component 204 relative to the proximal enclosure 210 along a longitudinal axis of the delivery device 200. The tapering of the proximal section 250 can allow the distal end portion 208 of the proximal sheath component 204 to smoothly advance distally over the proximal section 250, and the circumferential nodes 252 can contact an inner surface of the distal end portion 208 of the proximal sheath component 204 as the distal end portion 208 approaches the proximal abutment surface 214.

For example, as illustrated in FIG. 5A, the circumferential nodes 252 may gradually taper from the proximal abutment surface 214 in the proximal direction. With such a configuration, as the proximal sheath component 204 slides distally toward the proximal enclosure 210, the circumferential nodes 252 can advantageously guide the distal end portion 208 of the proximal sheath component 204 distally toward the proximal abutment surface 214 of the proximal enclosure 210 so that the outer surface of the proximal sheath component 204 is aligned with an outer surface of the proximal enclosure 210. Thus, the outer surfaces of the proximal enclosure 210 and the proximal sheath component 204 can provide a smooth outer profile for the delivery device 200 that can advantageously reduce the likelihood that the delivery device 200 catches or otherwise damages tissue within a body lumen as the delivery device 200 is moved therewithin.

Optionally, the proximal section 250 can comprise three circumferential nodes 252 and three circumferential cavities 254. The circumferential nodes 252 may extend proximally from the proximal abutment surface 214. The three circumferential cavities 254 can correspond to the number of U-shaped members of the valve anchor that are housed within the proximal sheath component 204 between the proximal sheath component 204 and the proximal section 250 of the proximal enclosure 210.

This advantageous feature of some embodiments can allow the distal enclosure 212 to be properly positioned along the delivery device 200 in order to ensure that distal enclosure 212 does not snag or become caught on any structure during retrieval of the delivery device 200.

Figure 5B:
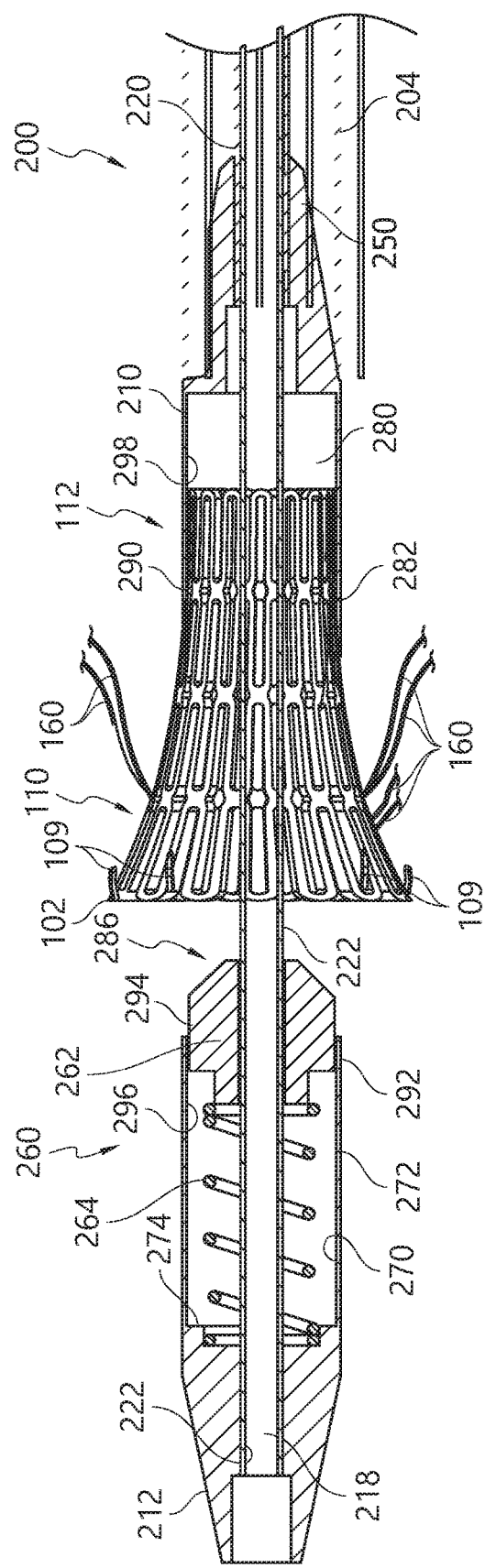

As also shown in FIGS. 5A and 5B, the proximal and distal enclosures 210, 212 can collectively house the support frame 102. The first and second core members 220, 222 can be actuated to separate the proximal and distal enclosures 210, 212, thereby permitting the support frame 102 to self-expand when in position within the valve anchor 104.

For example, by pushing or pulling the first core member 220, the second core member 222, and/or the proximal sheath component 204 relative to each other along the longitudinal axis of the delivery device 200, a clinician can control longitudinal movement of each of these components to permit the release of the support frame 102 and the valve anchor 104 of the valve prosthesis 100.

Further, in some embodiments, to facilitate delivery of the delivery device 200 to the target location, as shown in FIGS. 5A and 5B, the second core member 222 can include a lumen 218 to permit the delivery device 200 to move along a guidewire, which can extend through the lumen 218 of the second core member 222.

FIGS. 5A and 5B further illustrate positions of the proximal and distal enclosures 210, 212 during the release of the support frame 102. After separating the proximal and distal enclosures 210, 212 from the position illustrated in FIG. 5A to the position illustrated in FIG. 5A, the first end portion 110 of the support frame 102 can begin to expand from the compressed configuration to an expanded configuration. In some embodiments, the support frame 102 can have one or more anchors 109 (see also FIG. 2) at its first end portion 110 that, when engaged with the native valve structure can supplement the outward expansive force (due to self-expansion of the support frame 102) and its resultant frictional engagement, to mitigate downstream migration of the support frame 102 relative to the native valve structure. Thus, by opening the first end portion 110 first (before the second end portion 112, and via relative movement of the proximal and distal enclosures 210, 212), the first end portion 110 can "flower" out to facilitate release of the support frame and/or to engage with the native anatomy, such as the valve structure itself, to secure a longitudinal position of the support frame 102 relative to the native valve structure. Thereafter, the second end portion 112 of the support frame 102 can be controlled and released to become disengaged and released from the proximal enclosure 210.

In some embodiments, the first end portion 110 and the second end portion 112 can open simultaneously, at the same or different rates. For example, in some embodiments, the first end portion 110 and the second end portion 112 can open simultaneously, but with the first end portion 110 opening at a faster rate than the second end portion 112.

Advantageously, the use of the proximal enclosure 210 and the distal enclosure 212 allows for greater control and enhanced operation of the support frame 102. For example, by controlling the position and rate of separation of the proximal enclosure 210 and the distal enclosure 212, the opening of the support frame 102 at both the first end portion 110 and the second end portion 112 can be controlled. Further, by controlling the movement of the distal enclosure 212, the timing and rate of opening of the first end portion 110 can be controlled relative to the timing and rate of opening of the second end portion 112 (which may be controlled by the movement of the proximal enclosure 210).

Additionally and advantageously, by having separate proximal and distal enclosures 210, 212, the delivery device 200 may experience reduced frictional forces and minimize travel of the enclosures 210, 212 relative to the support frame 102.

In particular, in accordance with some embodiments, the distal carrier assembly 206 can comprise a plunger mechanism 260 that can facilitate expansion of the support frame 102. The plunger mechanism 260 can expand from a compressed state (shown in FIG. 5A) to an extended state (shown in FIG. 5A). The plunger mechanism 260 can be biased by a spring or other device in order to move automatically from the compressed state to the extended state. However, the plunger mechanism 260 can also be manually actuated by the clinician in some embodiments.

As illustrated, the plunger mechanism 260 can comprise a plunger head 262 and a biasing means 264. The plunger head 262 can comprise a conical or tapered proximal portion 286. The conical proximal portion 286 can be configured to not contact only the first end portion of the support frame 102 during delivery, but can also help center a distal end portion 290 of the tubular portion 282 of the proximal enclosure 210 relative to a longitudinal axis of the delivery device 200 and help align the distal end portion 290 with a proximal end portion 292 of the tubular portion 272 of the distal enclosure 212. The plunger head 262 can also comprise an outer circumferential surface 294 that can contact not only an inner surface 296 of the tubular portion 272, but can also contact an inner surface 298 of the tubular portion 282 when the tubular portion 282 is distally advanced over the conical proximal portion 286 of the plunger head 262.

Further, the plunger mechanism 260 can be housed within a distal lumen 270 of a tubular portion 272 of the distal enclosure 212. For example, the biasing means 264 may be a spring. The biasing means 264 can be interposed between an interior structure or wall 274 of the distal lumen 270 and a distal surface or structure 276 of the plunger head 262. The plunger head 262 can move proximally within the distal lumen 270 in order to continue to exert a proximally oriented force on the first end portion 110 of the support frame 102 until the support frame 102 exits the distal lumen 270. Thereafter, in accordance with some embodiments, the support frame 102 can self-expand until the second end portion 112 is pulled out of a proximal lumen 280 of a tubular portion 282 of the proximal enclosure 210 as the support frame 102 continues to expand. The expanded state of the support frame 102 is illustrated in FIGS. 1 and 2, discussed above.

Figure 6A:
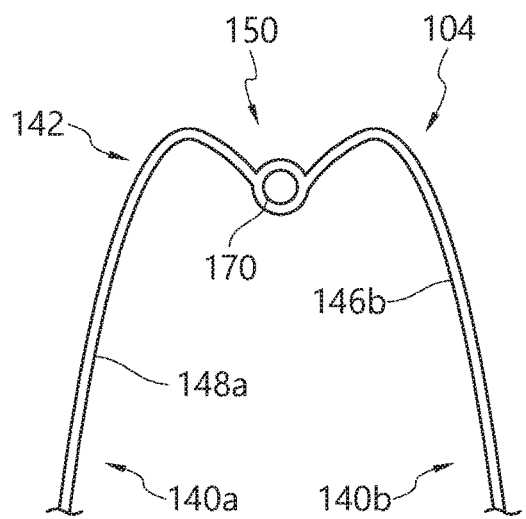
FIGS. 6A-6H are views of valve anchors, according to some embodiments.

Referring now to FIG. 6A, FIG. 6A illustrates an embodiment of the valve anchor 104 having an engagement area 150 that is formed between first and second U-shaped members 140a, 140b. The first U-shaped member 140a comprises a second leg 148a, and the second U-shaped member 140b comprises a first leg 146b. The engagement area 150 can be formed or disposed between the first leg 146b and the second leg 148a.

The engagement area 150 can comprise an eyelet or anchor retention component 170, and the first and second legs 146b, 148a can extend in a direction toward the peak portions 142 thereof. The first and second legs 146b, 148a can also each comprise a bend or curve that causes the first and second legs 146b, 148a to bend in a direction away from the peak portions 142 and to converge at the anchor retention component 170. This configuration creates a local concavity or cove whereinto the link mechanism 160 can slide and be engaged. Further, as discussed further below, the anchor retention component 170 can be used to engage with the control member or a grasper to facilitate movement and control of the positioning of the valve anchor 104 during delivery. As shown in FIG. 6A, in some embodiments, the anchor retention component 170 may be in a shape of an eyelet, aperture, or hole that extends through the engagement area 150 of the valve anchor 104.

Further, as illustrated, the anchor retention component 170 can allow for the control member or the grasper to engage with the valve anchor 104 for a retrograde approach (as shown in FIGS. 11A-11F of U.S. Patent Application No. 62/781,537, noted above) or an antegrade approach (as shown in FIGS. 12A-12F of U.S. Patent Application No. 62/781,537, noted above). For example, the anchor retention component 170 can receive a control member or a grasper approaching the valve anchor 104 proximal to the peak portions 142 to allow the valve anchor 104 to be used for a retrograde (e.g., transfemoral retrograde) approach in delivering the valve anchor 104. Further, the anchor retention component 170 can receive the control member or the grasper approaching the valve anchor 104 proximal to the first and second U-shaped members 140a, 140b to allow the valve anchor 104 to be used for an antegrade, apical, or transapical approach in delivering the valve anchor 104.

Figure 6B:
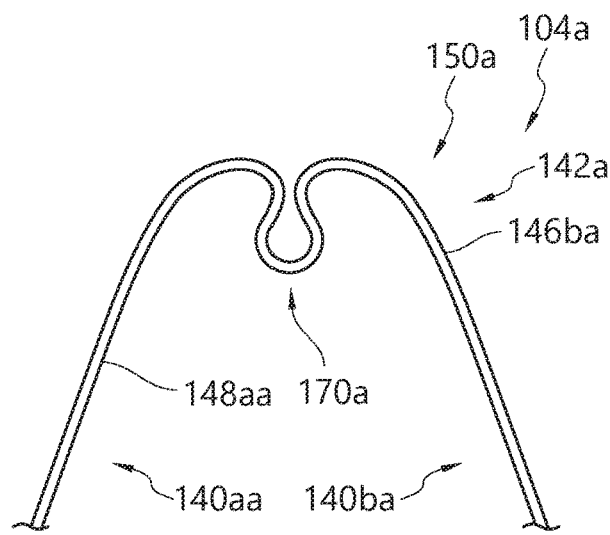

Similar to FIG. 6A, FIG. 6B illustrates an embodiment of a valve anchor 104a having an engagement area 150a formed between first and second U-shaped members 140aa, 140ba. The first U-shaped member 140aa comprises a second leg 148aa, and the second U-shaped member 140ba comprises a first leg 146ba. The engagement area 150a is formed or disposed between the first leg 146ba and the second leg 148aa. The first and second legs 146ba, 148aa can extend in a direction toward the peak portions 142a thereof. The first and second legs 146ba, 148aa can also each comprise a bend or curve that causes the first and second legs 146ba, 148aa to bend in a direction away from the peak portions 142a and to converge to form a keyhole shape or narrow-waisted cove 170a. The keyhole shape or narrow-waisted cove 170a may be used as an anchor retention component to engage with the control member or the grasper. Again, this configuration creates a local concavity or cove whereinto the link mechanism 160 can slide and be engaged.

Figure 6C:
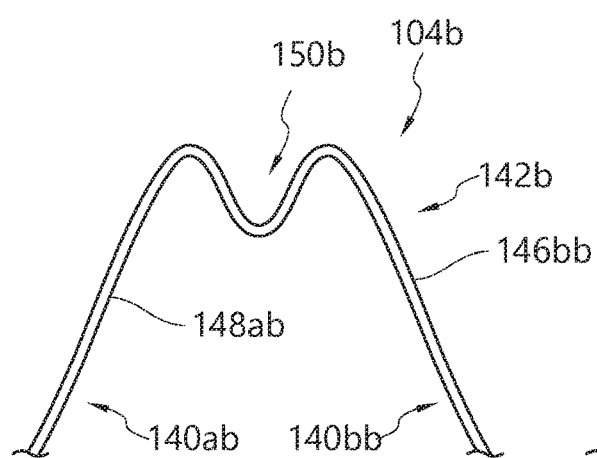
Figure 6D:
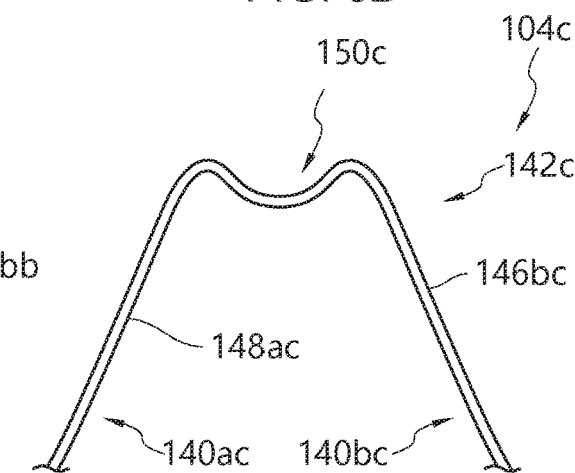

Further, FIGS. 6C and 6D illustrate additional embodiments of valve anchors 104b, 104c having engagement areas 150b, 150c. Similar to the embodiments shown in FIGS. 6A and 6B, the details of which will not be repeated for brevity (but can optionally be incorporated into the embodiments of FIGS. 6C and 6D, as well), first and second U-shaped members 140ab, 140bb, 140ac, 140bc can have bends or curves which form the respective engagement areas 150b, 150c. These configurations can be referred to as collectively providing a "triple switchback" design that is created by the first and second legs 146bb, 148ab and 146bc, 148ac, respectively. The engagement area 150b is deeper than the engagement area 150c, and the depth can be varied in order to facilitate capture of the link mechanism 160 therein.

Figure 6E:
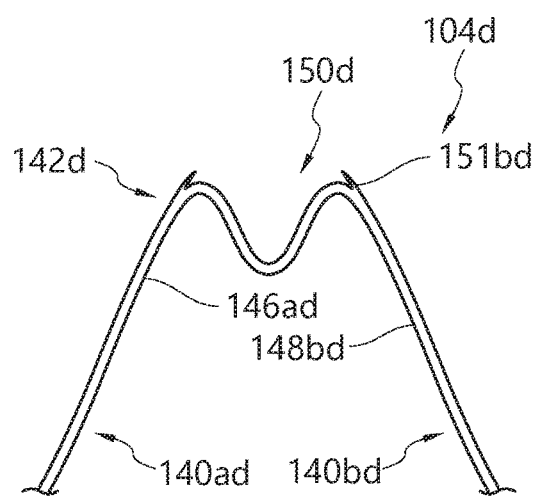

FIG. 6E illustrates an additional embodiment of valve anchor 104d having engagement area 150d. Similar to the embodiments shown in FIGS. 6A and 6B, the details of which will not be repeated for brevity (but can optionally be incorporated into the embodiment of FIG. 6E, as well), first and second U-shaped members 140ad, 140bd can have bends or curves which form the engagement area 150d. Similarly, this configuration can also be referred to as providing a "triple switchback" design that is created by the first and second legs 146bd, 148ad.

In addition, as shown in FIG. 6E, in some embodiments, the engagement area 150d can include one or more barbs 151d to facilitate capture of the link mechanism 160 therein. In some embodiments, the barbs 151d can deflect downward to allow the link mechanism 160 to pass over the barb 151d, while preventing the link mechanism 160 from returning over the barb 151d.

Figure 6F:
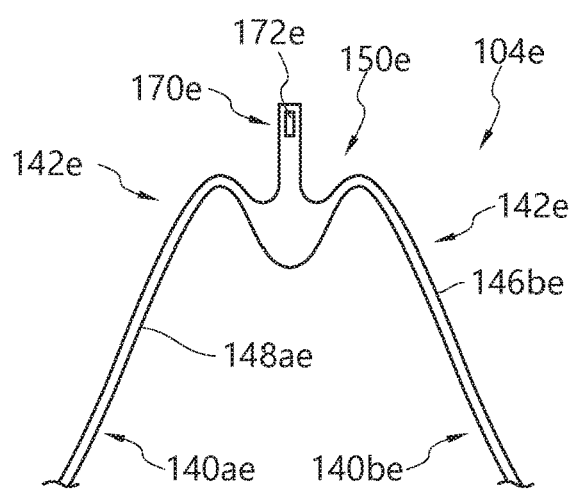

FIG. 6F illustrates an additional embodiment of valve anchor 104e having engagement area 150e. Similar to the embodiments shown in FIGS. 6A and 6B, the details of which will not be repeated for brevity (but can optionally be incorporated into the embodiment of FIG. 6F, as well), first and second U-shaped members 140ae, 140be can have bends or curves which form the engagement area 150e. The first and second legs 146be, 148ae can also each comprise a bend or curve that causes the first and second legs 146be, 148ae to bend in a direction away from the peak portions 142e and to converge at towards the clasper tang 170e to create a local concavity or cove whereinto the link mechanism 160 can slide and be engaged.

In addition, as shown in FIG. 6F, in some embodiments, the engagement area 150e can also comprise a central grasping portion or clasper tang 170e that extends from the engagement area 150e. As discussed below, the clasper tang 170e can be used as an anchor retention component to engage with a control member or grasper of the delivery device to facilitate movement and control of the positioning of the valve anchor 104 during delivery. In some embodiments, the clasper tang 170e can comprise an engagement structure, socket, aperture, or protrusion 172. The engagement structure 172 can be positioned along the length or body of the clasper tang 170e. As illustrated, the engagement structure 172 can be positioned centrally at a distal end portion of the clasper tang 170e.

Figure 6G:
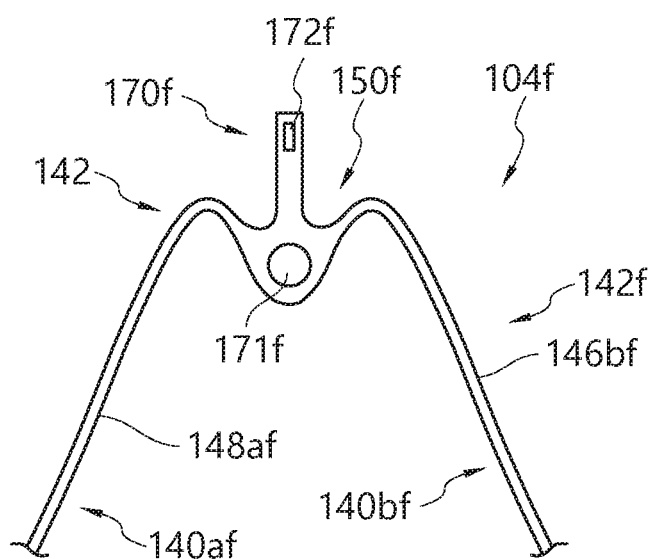

FIG. 6G illustrates an additional embodiment of valve anchor 104f having engagement area 150f. Similar to the embodiment shown in FIGS. 6A and 6B, the details of which will not be repeated for brevity (but can optionally be incorporated into the embodiment of FIG. 6G, as well), first and second U-shaped members 140af, 140bf can have bends or curves which form the engagement area 150f. The first and second legs 146bf, 148af can also each comprise a bend or curve that causes the first and second legs 146bf, 148af to bend in a direction away from the peak portions 142f and to converge at towards the clasper tang 170f to create a local concavity or cove whereinto the link mechanism 160 can slide and be engaged.

In addition, as shown in FIG. 6G, in some embodiments, the engagement area 150f can also comprise an eyelet or anchor retention component 171f and a central grasping portion or clasper tang 170f that extends from the engagement area 150f. Similar to the embodiment shown in FIG. 6A, the anchor retention component 171f may be in a shape of an eyelet, aperture, or hole that extends through the engagement area 150f of the valve anchor 104f. Further, similar to the embodiment shown in FIG. 6F, the clasper tang 170f can be used as another anchor retention component to engage with a control member or grasper of the delivery device to facilitate movement and control of the positioning of the valve anchor 104f during delivery.

As illustrated, the clasper tang 170f can allow for the control member or the grasper to engage with the valve anchor 104f for a transfemoral retrograde approach (as shown in FIGS. 11A-11F of U.S. Patent Application No. 62/781,537, noted above), and the anchor retention component 171f can allow for the control member or the grasper to engage with the valve anchor 104f for an antegrade approach (as shown in FIGS. 12A-12F of U.S. Patent Application No. 62/781,537, noted above). For example, the clasper tang 170f can receive a control member or a grasper approaching the valve anchor 104f proximal to the peak portions 142f to allow the valve anchor 104 to be used for a retrograde (e.g., a transfemoral retrograde) approach in delivering the valve anchor 104f. Further, the anchor retention component 171f can receive the control member or the grasper approaching the valve anchor 104f proximal to the first and second U-shaped members 140af, 140bf to allow the valve anchor 104f to be used for an antegrade, apical, or transapical approach in delivering the valve anchor 104f.

Further, as also illustrated and discussed later in FIGS. 10A-10D, the engagement structure 172f can comprise an aperture that can receive a respective protrusion of a distal end portion of a grasper member for coupling the clasper tang 170f to the grasper. However, some embodiments can be provided in which the engagement structure 172 of the clasper tang 170f uses a protrusion and the grasper member uses a corresponding aperture.

Figure 6H:
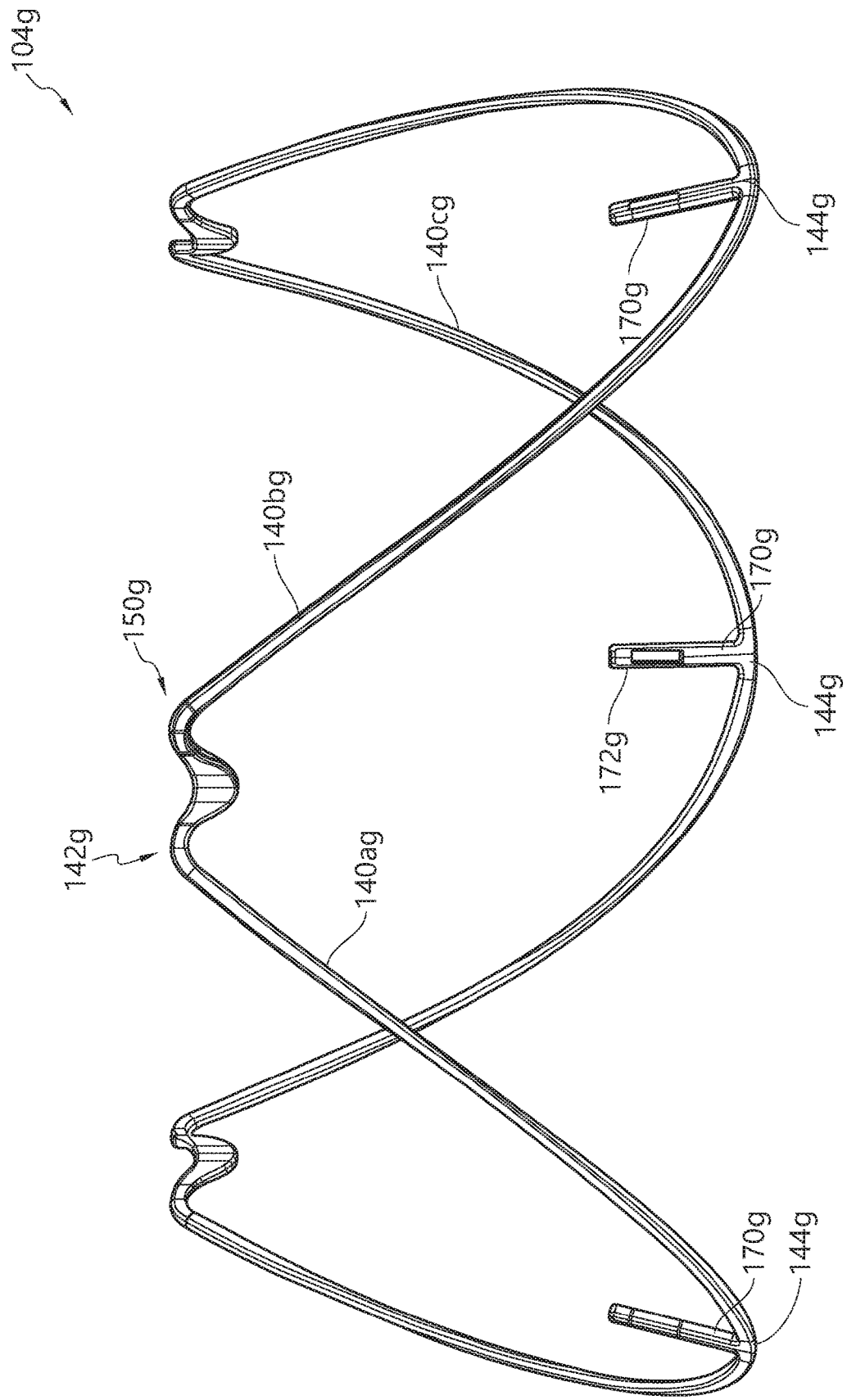

FIG. 6H illustrates an additional embodiment of valve anchor 104g having engagement area 150g. Similar to the embodiment shown in FIGS. 6C and 6D, the details of which will not be repeated for brevity (but can optionally be incorporated into or omitted from the embodiment of FIG. 6H), the first and second U-shaped members 140ag, 140bg can have bends or curves which form the engagement area 150g. These configurations can be referred to as collectively providing a "triple switchback" design that is created by the first and second U-shaped members 140ag, 140bg, respectively.

In addition, as shown in FIG. 6H, in some embodiments, the U-shaped members 140ag, 140bg, 140cg, can optionally comprise a central grasping portion or clasper tang 170g that extends from a medial location of the base portion of the U-shaped members 140ag, 140bg, 140cg. Optionally, multiple valve anchors 104g can each comprise one or more U-shaped members 140ag, 140bg, 140cg, wherein the multiple valve anchors 104g cooperatively engage with the aortic sinus to anchor the valve prosthesis as described herein.

For example, the clasper tang 170g can extend from a base portion 144g of the U-shaped member 140ag, 140bg in an axial direction toward the engagement areas of the valve anchor 104g or radially inside the bend of the U-shaped members 140ag, 140bg of the valve anchor 104g.

As discussed below, the clasper tang 170g can be used as an anchor retention component. For example, the clasper tang 170g can engage with a control member or grasper of the delivery device to facilitate movement and control of the positioning of the valve anchor 104g during delivery. This engagement can advantageously provide greater control over the articulation of the U-shaped members, as well as to function as a link motion limiter. Such features and benefits are discussed further below.

In some embodiments, by locating the clasper tang 170g at the base portion of the U-shaped members 140ag, 140bg, 140cg, the valve anchor 104g may have an increased bending stiffness at the grasper attachment points during delivery. In some applications, the valve anchor 104g may advantageously be less likely to invert during delivery due to the increased bending stiffness. Further, control of the base portions 144g can permit a clinician to specifically control the articulation and placement of the U-shaped members relative to the sinus structure of the native valve during delivery and placement of the valve anchor 104g.

In some embodiments, the clasper tang 170g can comprise an engagement structure, socket, aperture, or protrusion 172g. The engagement structure 172g can be positioned along the length or body of the clasper tang 170g. As illustrated, the engagement structure 172g can be positioned centrally at a distal end portion of the clasper tang 170g.

As illustrated and discussed in regard to other aspects of this disclosure (see, e.g., FIGS. 10A-10F), the clasper tang 170g can allow for the control member or the grasper to engage with the valve anchor 104g for a retrograde approach (as shown in FIGS. 11A-11F of U.S. Patent Application No. 62/781,537, noted above) or for an antegrade approach (as shown in FIGS. 12A-12F of U.S. Patent Application No. 62/781,537, noted above).

For example, the clasper tang 170g can receive a control member or a grasper approaching the valve anchor 104g proximal to the peak portions 142g to allow the valve anchor 104g to be used for a retrograde approach (e.g., a transfemoral retrograde approach) in delivering the valve anchor 104g. Further, the clasper tang 170g can receive the control member or the grasper approaching the valve anchor 104g proximal to the first and second U-shaped members 140ag, 140bg to allow the valve anchor 104g to be used for an antegrade approach (e.g., an apical or transapical approach) in delivering the valve anchor 104f.

Figure 9A:
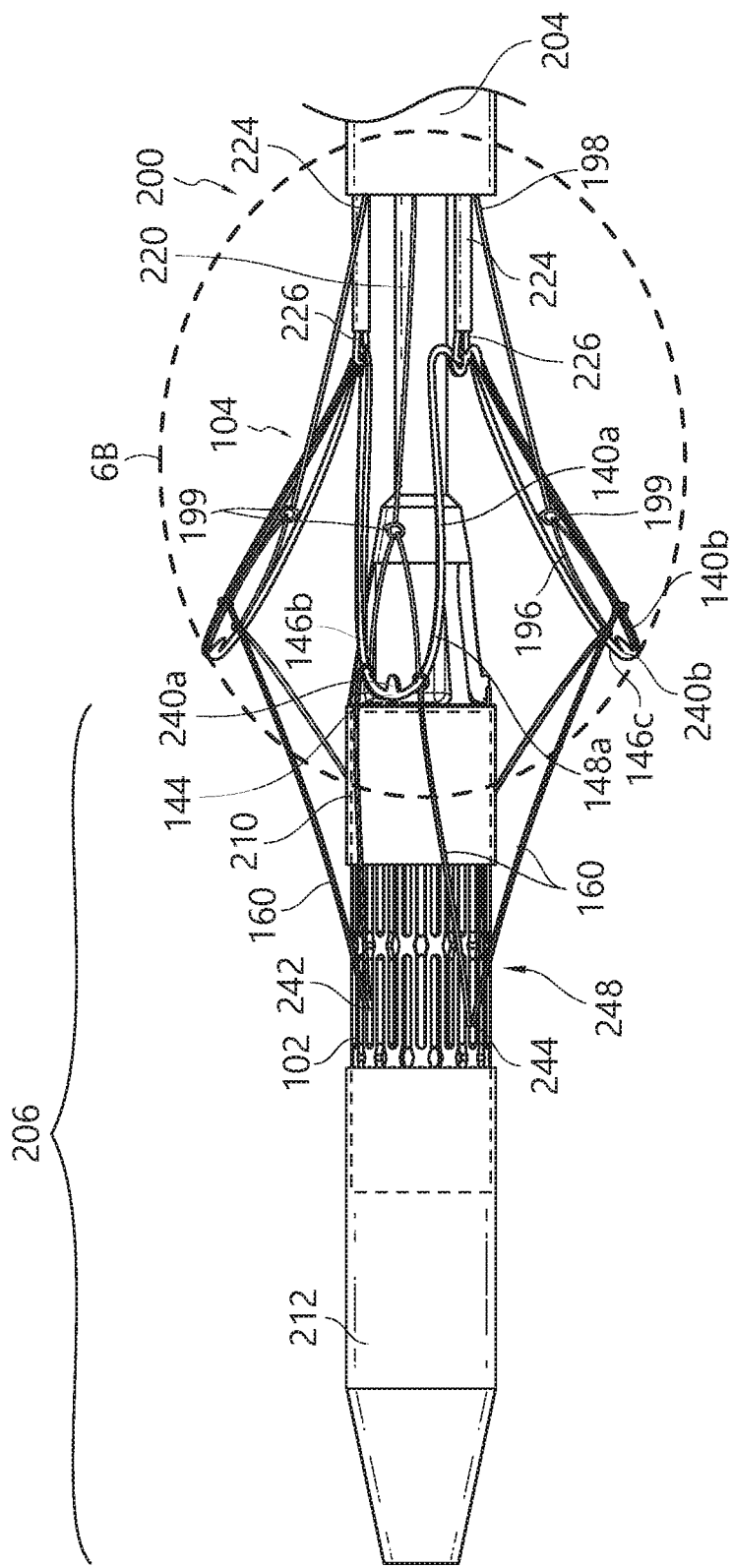
FIG. 9A is a side view of the valve prosthesis and delivery device of FIG. 8A, showing a proximal sheath retracted from over a valve anchor, according to some embodiments.
Figure 9B:
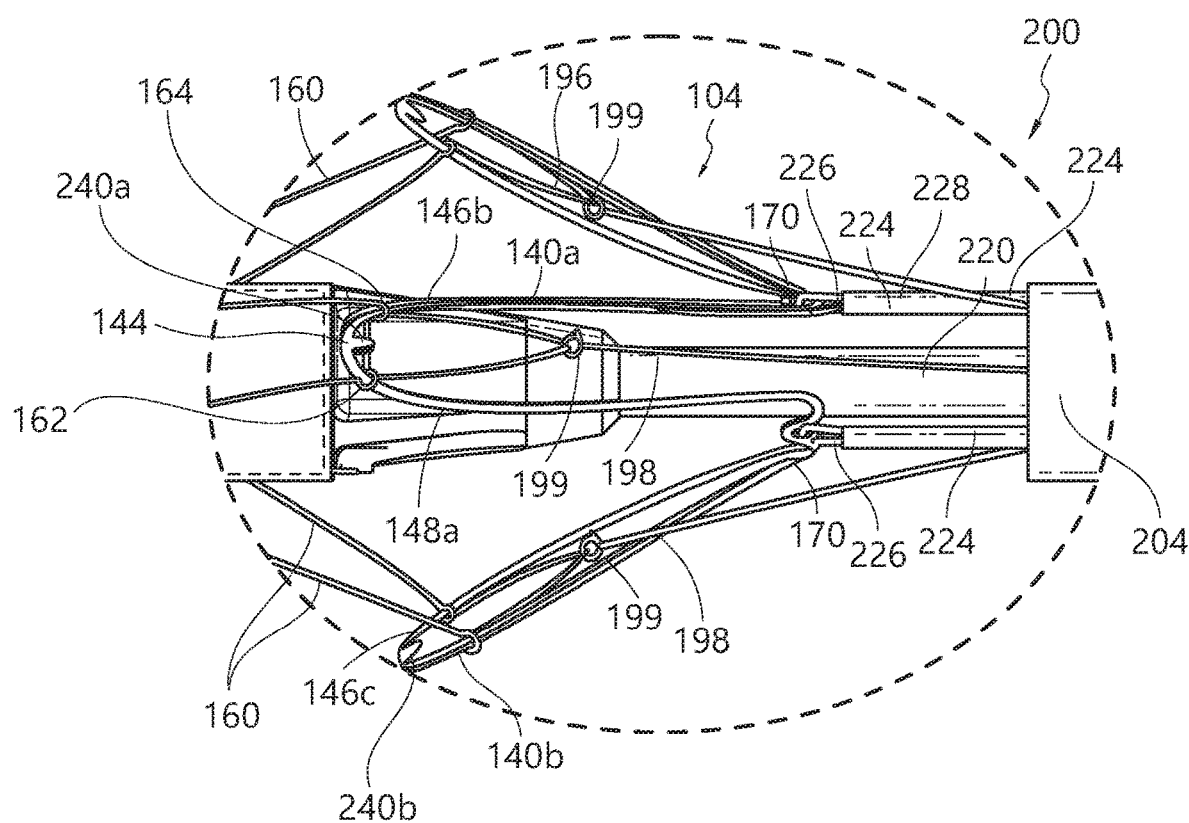
FIG. 9B is an enlarged detail view of the valve prosthesis and delivery device of FIG. 9A, according to some embodiments.
Figure 9C:
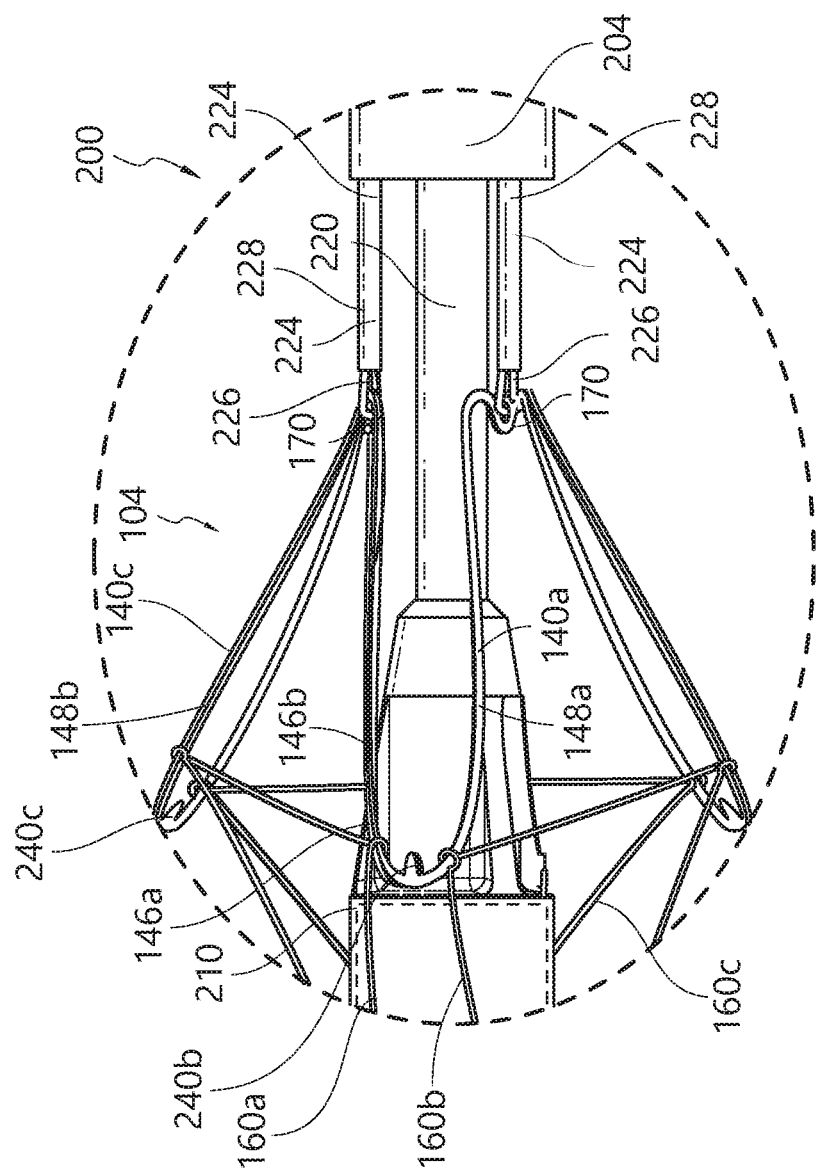
FIG. 9C is an enlarged detail view of the valve prosthesis and delivery device of FIG. 8B, showing a proximal sheath retracted from over a valve anchor, according to some embodiments.
Figure 9D:
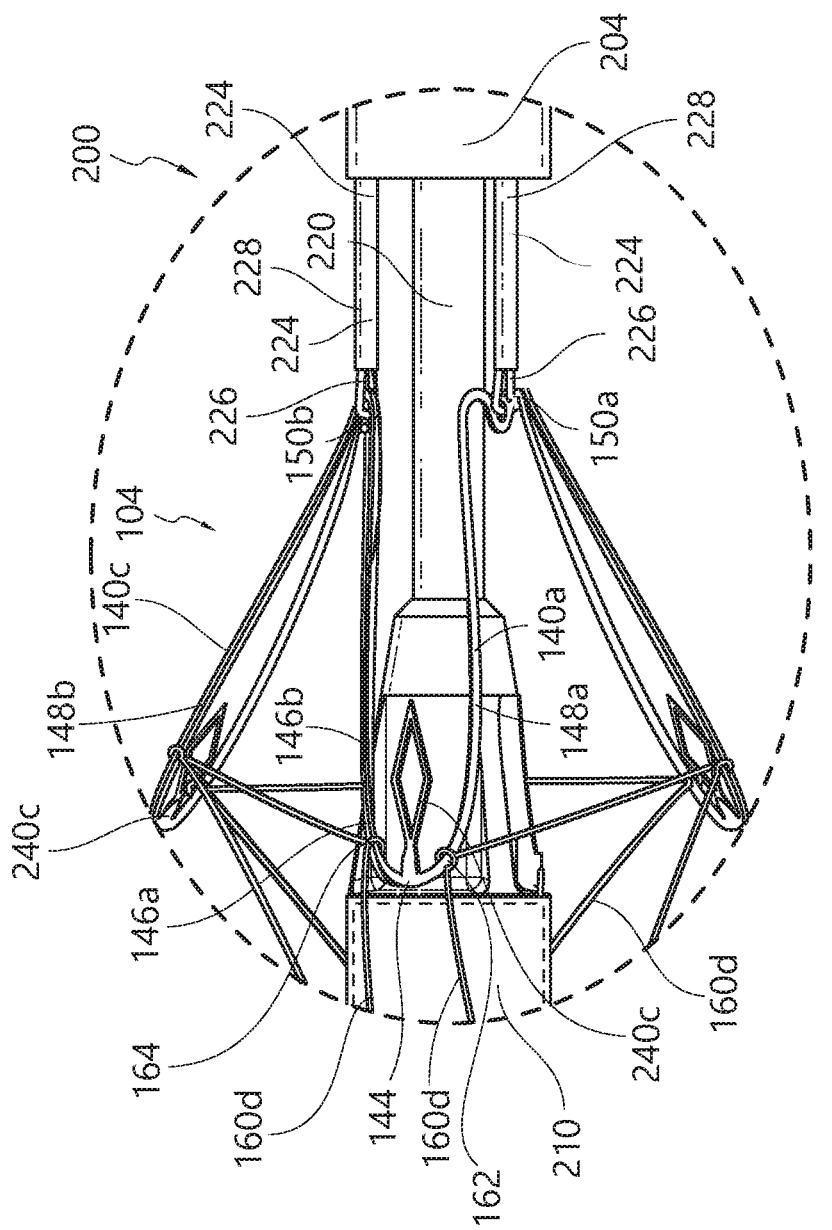
FIG. 9D is an enlarged detail view of a valve prosthesis having a valve anchor with a link motion limiter, according to some embodiments.
Figure 10A:
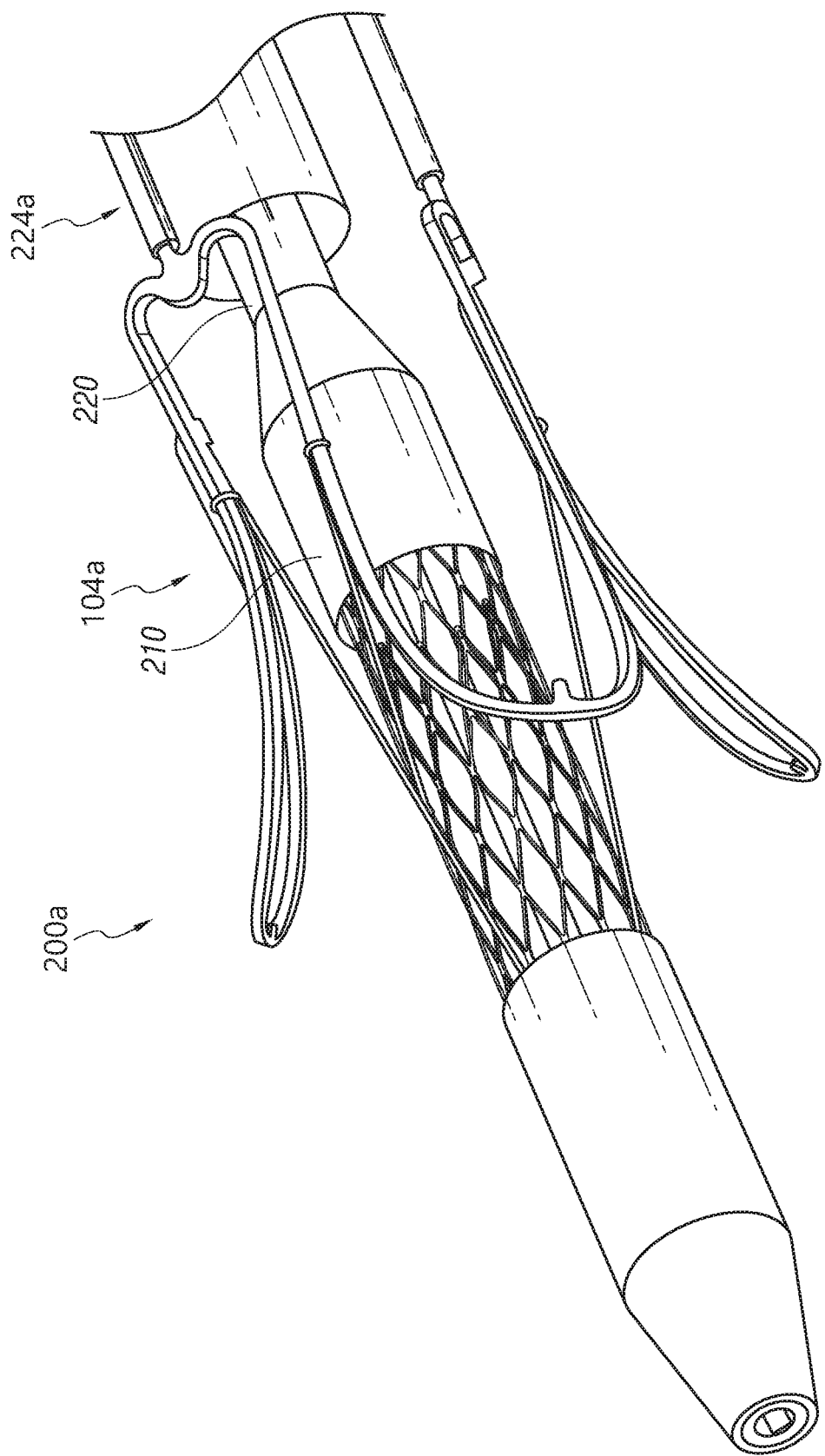
FIGS. 10A-10D are views of a valve delivery device having a grasper mechanism for engaging a valve anchor, according to some embodiments.
Figure 10B:
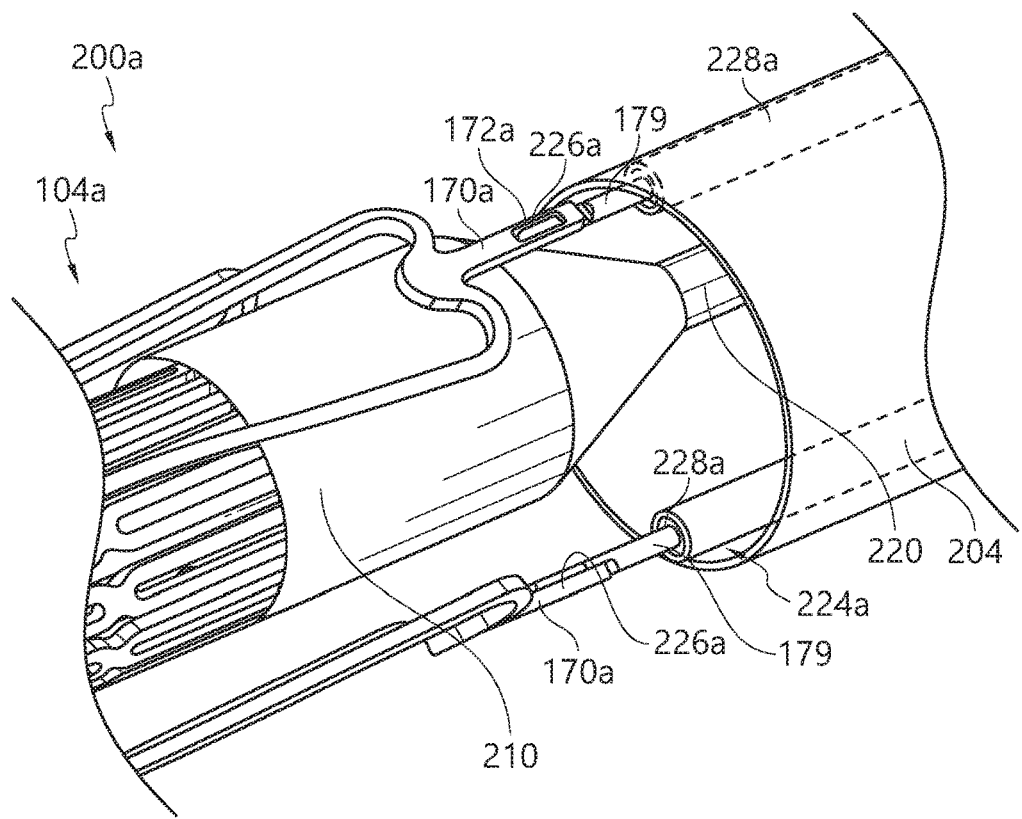
Figure 10C:
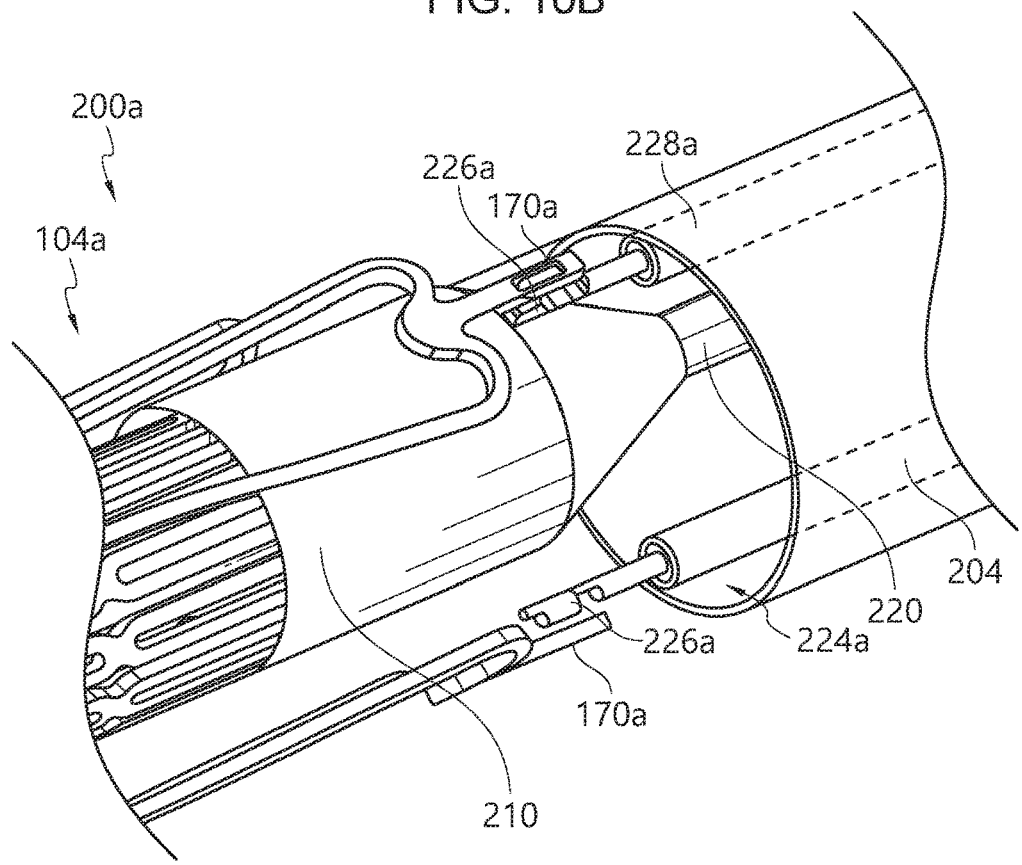
Figure 10D:
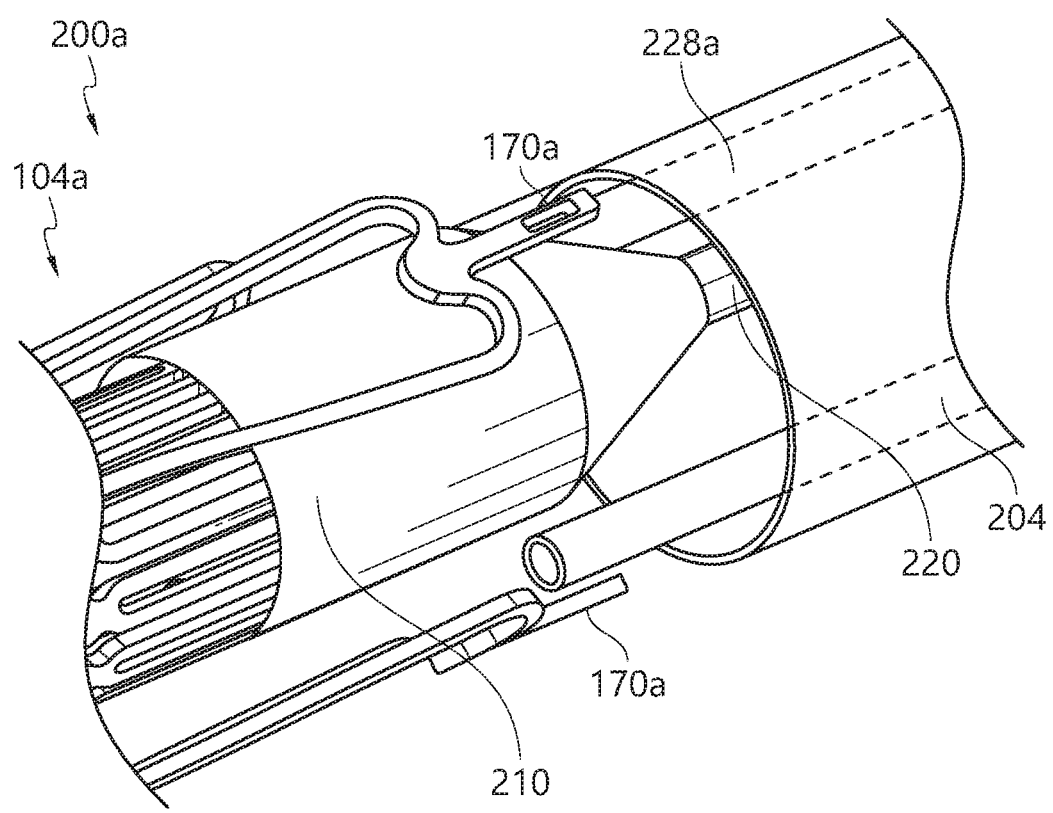
Figure 10E:
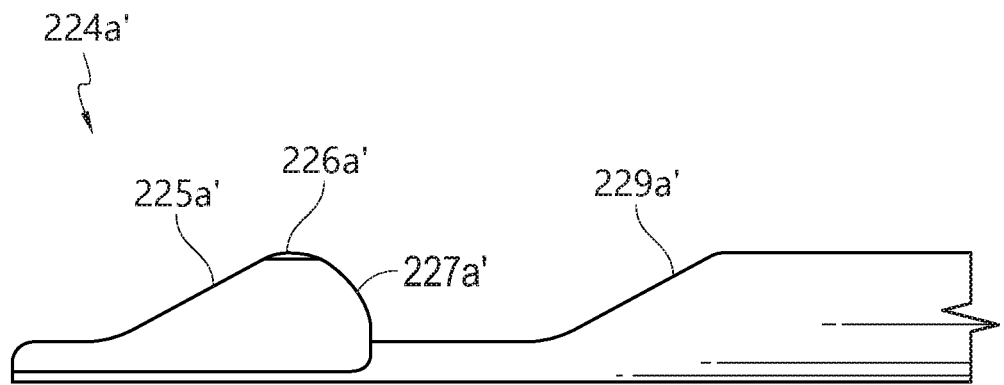
FIGS. 10E and 10F are side and top views of a grasper mechanism, according to some embodiments.
Figure 10F:
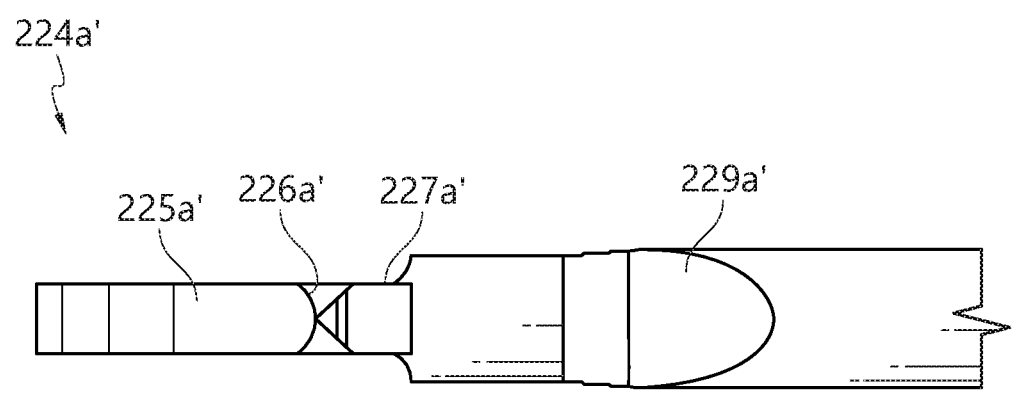
Figure 10G:
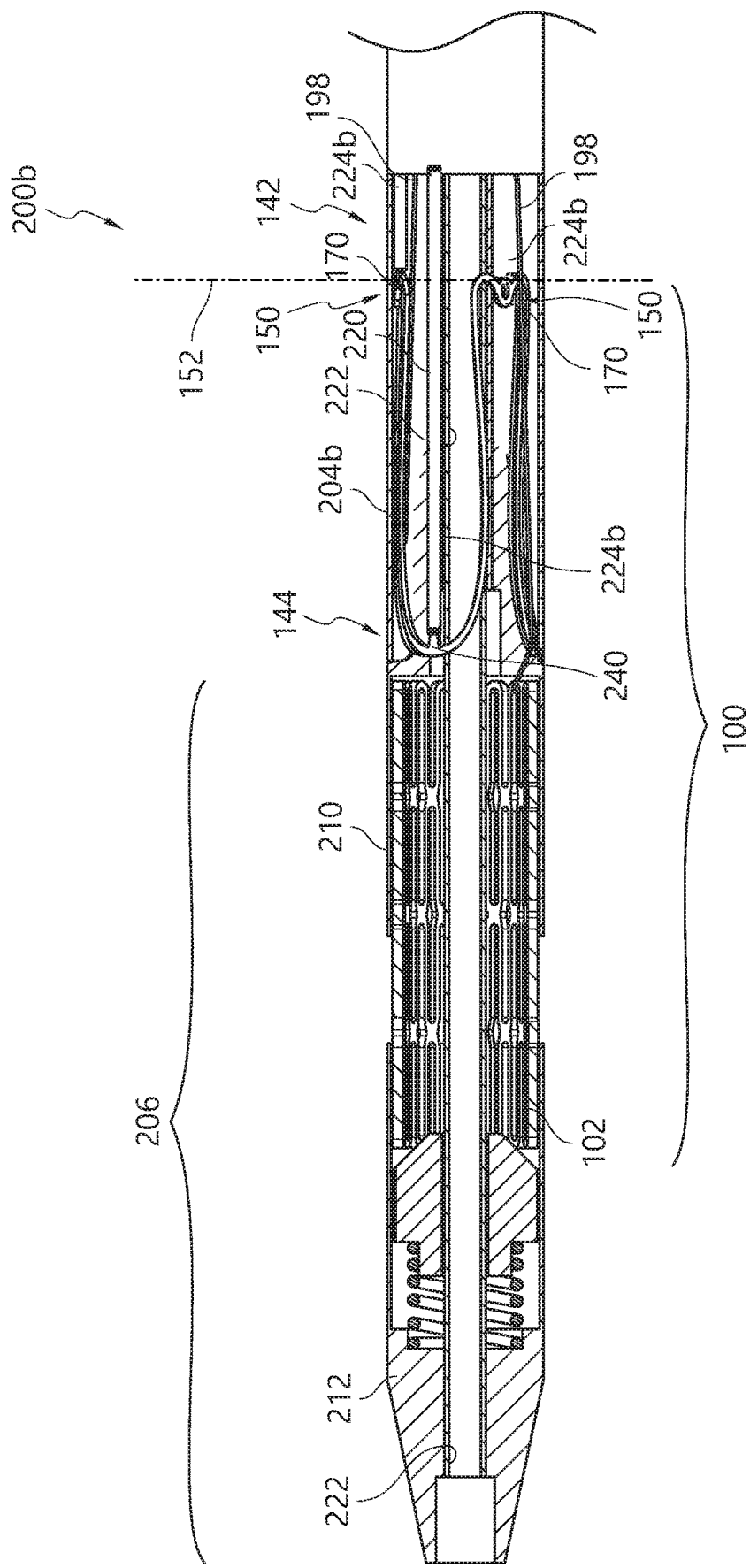
FIGS. 10G and 10H are views of a valve delivery device having a grasper mechanism for engaging a valve anchor, according to some embodiments.
Figure 10H:
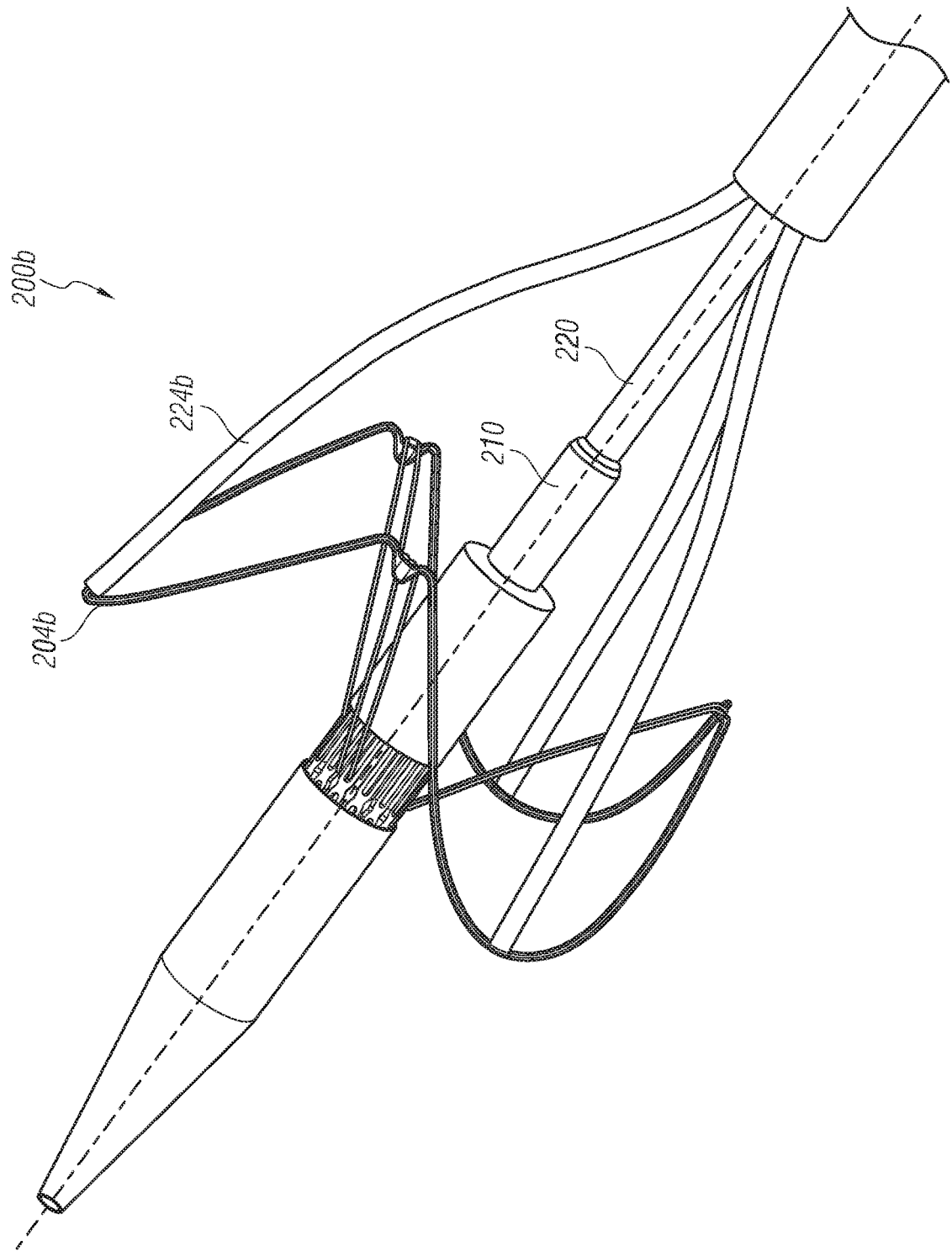

Optionally, as noted above, the clasper tang 170g (collectively, with the grasper 224b, as shown in the example of FIGS. 10G and 10H) can also serve as a link motion limiter, as described herein with regard to FIGS. 9A-9E, to provide an enlarged profile as to restrict or prevent motion of the link mechanism as the link mechanism slides along the U-shaped members 140*ag*, 140*bg*, 140*cg* of the valve anchor 104*g*.

These various designs are examples of engagement areas that can be used in some embodiments disclosed herein. Further, in any of the embodiments disclosed in FIGS. 6A-6D, the engagement area can comprise barbs or hooks over which the link mechanism 160 can pass. The barbs or hooks can permit one-way motion of the link mechanism 160—once the link mechanism 160 crosses the barbs or hooks, the barbs or hooks will prevent reverse movement of the link mechanism 160 over the barbs or hooks. The illustrated embodiments provide double peaks or coves that can tend to capture the link mechanism during the stages of prosthesis delivery, as discussed herein. When the link mechanism is so captured, the valve prosthesis 100 can be in a position referred to as a "retained" position.

Figure 7A:
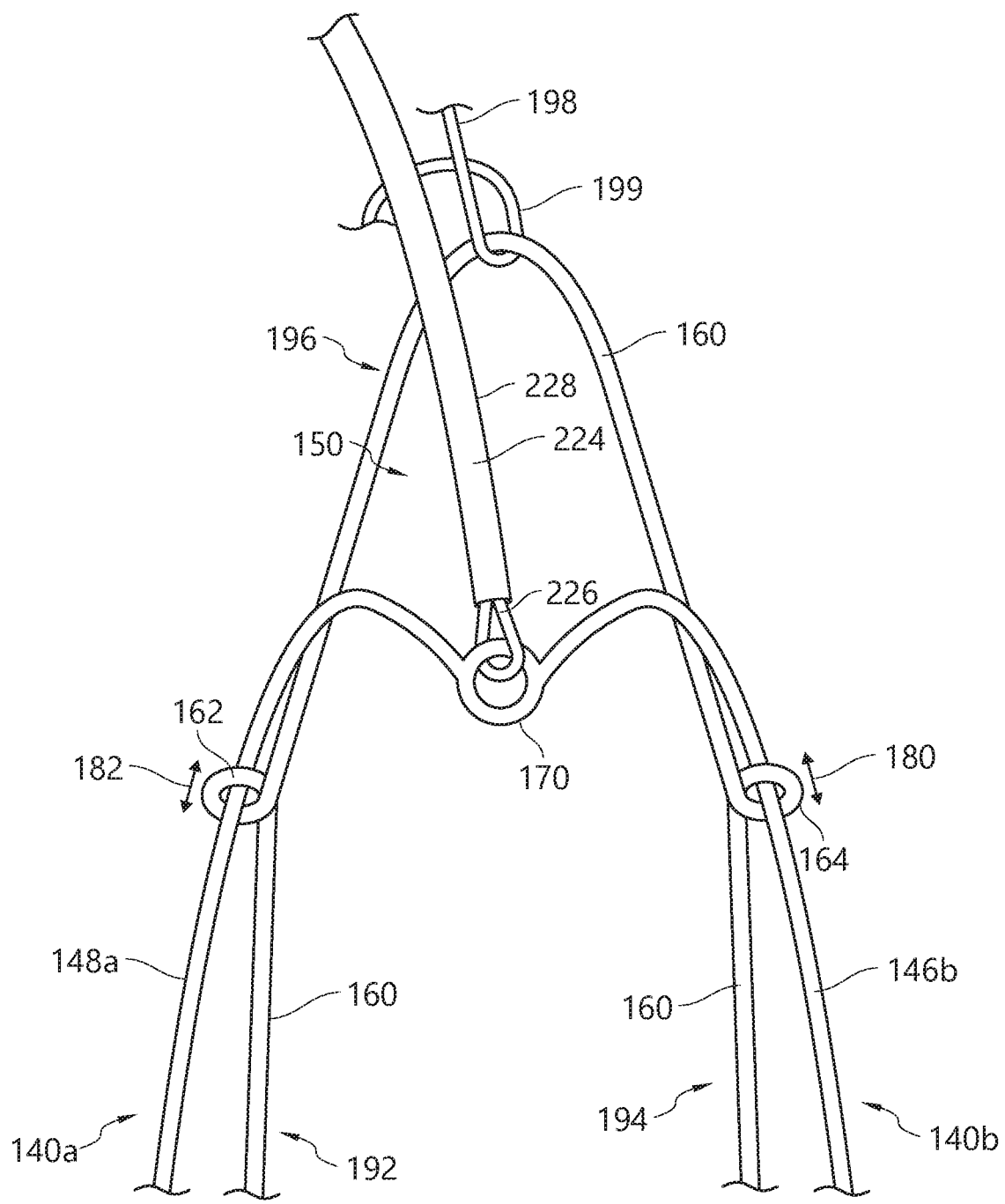
FIGS. 7A-7C are enlarged views of progressive movement of a link mechanism along an engagement area of a valve prosthesis, moving from a position in which the link mechanism is coupled to a tension member to a position in which the link mechanism is retained in the engagement area of the valve prosthesis, according to some embodiments.
Figure 7B:
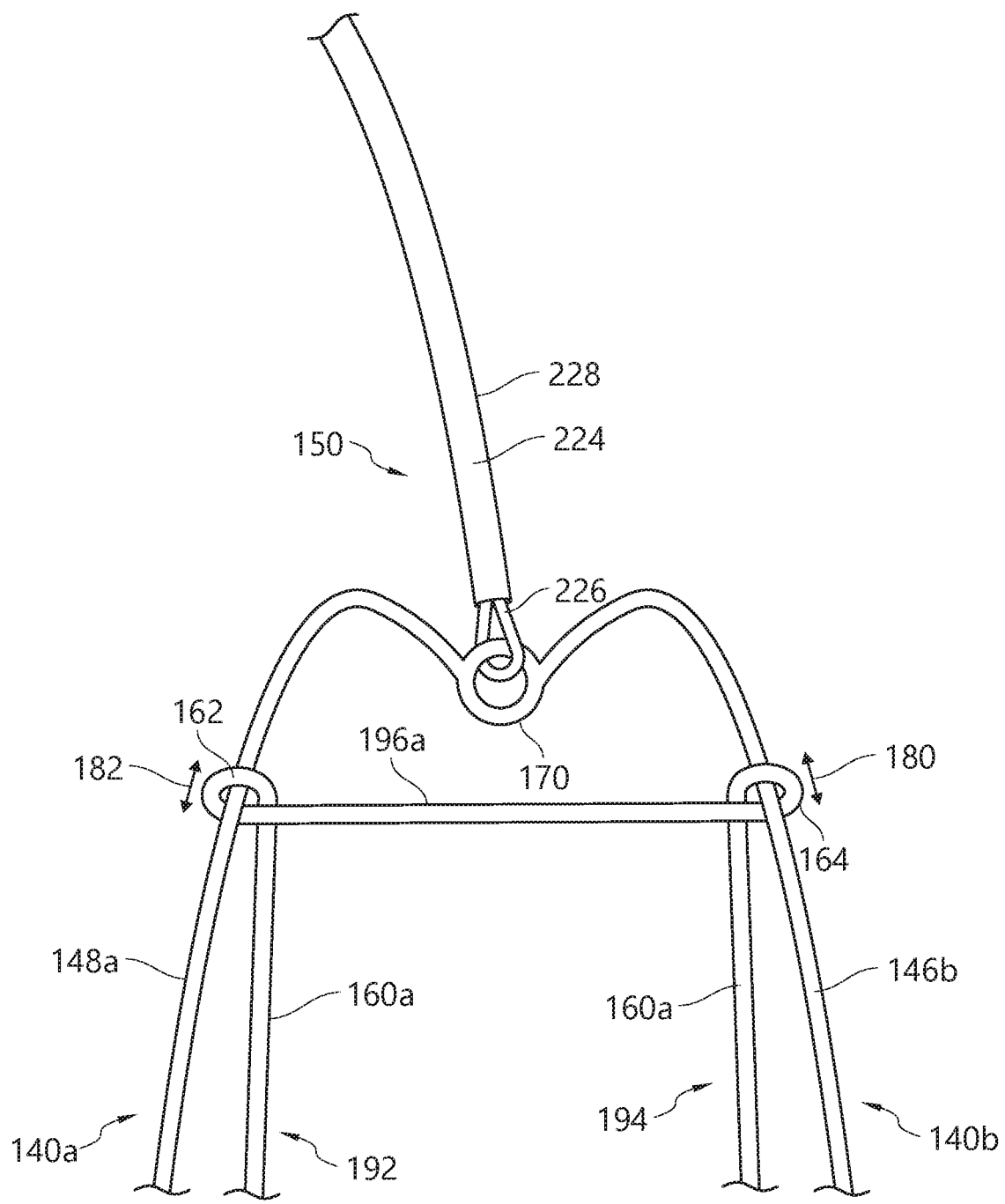
Figure 7C:
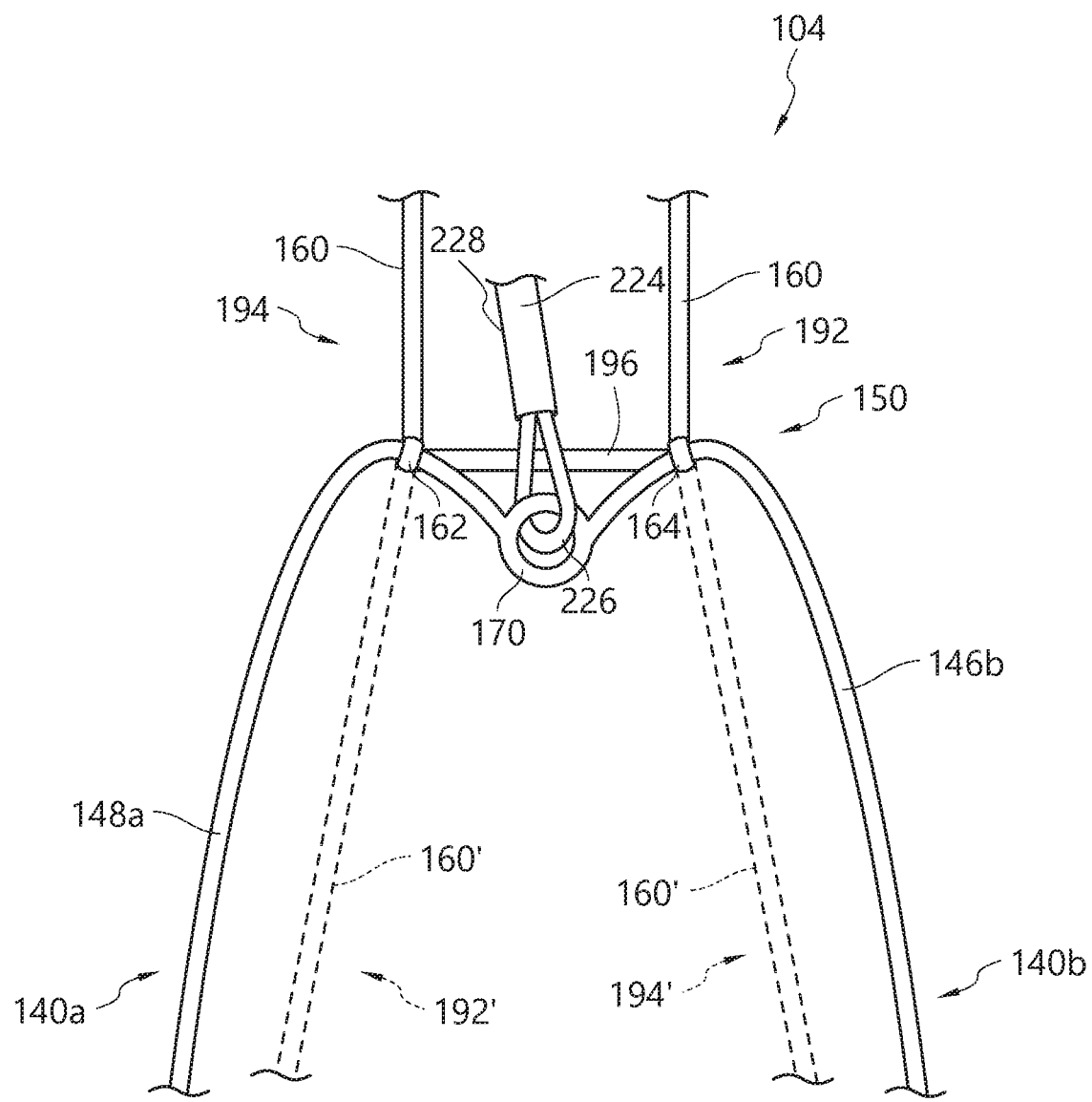

FIGS. 7A-7C illustrate movement of the link mechanism along legs of the U-shaped members and capture of the link mechanism within the engagement area, according to some embodiments. FIG. 7A illustrates an embodiment of the valve anchor 104 having first and second U-shaped members 140*a*, 140*b* and a link mechanism 160 that is in the slidable position. FIG. 7C illustrates an embodiment of the valve anchor 104 with the link mechanism 160 in the retained position.

As illustrated in FIG. 7A, the link mechanism 160 is in a slidable position and therefore, can slide freely along the first and second legs 146*b*, 148*a* of the first and second U-shaped members 140*a*, 140*b*, as indicated by the arrows 180, 182. The link mechanism 160 has a loop 162 that loops around the second leg 148*a* of the first U-shaped member 140*a*, and a loop 164 that loops around the first leg 146*b* of the second U-shaped member 140*b*. The loops 162, 164 can be shaped in mirror images of each other (i.e., the pathway or course of the link mechanism 160 around the second leg 148*a* and the first leg 146*b* can be mirror images of each other), as shown.

As also generally illustrated in FIG. 7A, the link mechanism 160 can be woven between the U-shaped member 140 and corresponding circumferential attachment points or positions at or on the support frame 102. For example, a first segment 192 of the link mechanism 160 can loop around the second leg 148*a* and extend towards a first attachment point on the support frame. Further, a second segment 194 of the link mechanism 160 can loop around the first leg 146*b* and extend towards a second attachment point on the support frame, different from the first attachment point. This weaving pattern is also generally shown in FIGS. 8A and 9A.

Furthermore, with the first and second segments 192, 194 extending away from the engagement area 150, it is also apparent that in FIG. 7A, the support frame is positioned somewhat distally relative to the valve anchor 104, thus causing the link mechanism 160, when taut, to extend toward the support frame in a direction away from the engagement area 150. Furthermore, an intermediate segment 196 of the link mechanism 160 may have some slack and be relatively long (compared to its status and length shown in FIG. 7C, which is explained below).

In some embodiments, the slack and length in the intermediate segment 196 of the link mechanism 160, when the link mechanism 160 is in the slidable position, allow the intermediate section 196 to be engaged by a tension member 198. As shown, the tension member 198 can comprise a flexible loop 199 that can be engaged with the intermediate section 196 such that the intermediate section 196 passes through the flexible loop 199. As discussed further below, the tension member 198 can extend proximally relative to the prosthesis 100 and assist in maintaining the intermediate section 196 in a tucked or compact configuration, so that the link mechanism 160 does not catch or become tangled during advancement of the prosthesis 100 to the target valve annulus during the procedure.

For example, in use, the tension member 198 can be maintained at a position that generally allows the intermediate section 196 to be pulled proximally to remove or reduce slack in the link mechanism 160 when the valve anchor 104 is in the compressed configuration. In some embodiments, the tension members 198 can be positioned in a fixed position relative to the grasper 224, and the flexible loop 199 can be longitudinally positioned distal or proximal to distal ends, pinchers, or hooks 226 of the grasper 224. However, during relative movement of the support frame 102 and the valve anchor 104, when the support frame 102 is distally advanced relative to the valve anchor 104 (when the anchor 104 is expanded at the target location), the slack in the intermediate section 196 will lessen and eventually, the flexible loop 199 of the tension member 198 will bend and release the intermediate section 196, thus disengaging the tension member 198 from the link mechanism 160. The general arrangement of the prosthesis 100, including the when loaded onto the delivery device, as shown in FIGS. 8A-9B and in the delivery stages of FIGS. 11A and 11B of U.S. Patent Application No. 62/781,537, noted above.

Further, various embodiments of the link mechanism 160 (e.g., 160*a*, 160*b*, 160*c*, 160*d*, 160*e*, and/or combinations thereof) are illustrated in FIGS. 8A-8G. In accordance with some embodiments, it is contemplated that any version of the link mechanism can be interchangeably used with the prosthesis or features thereof.

Figure 8A:
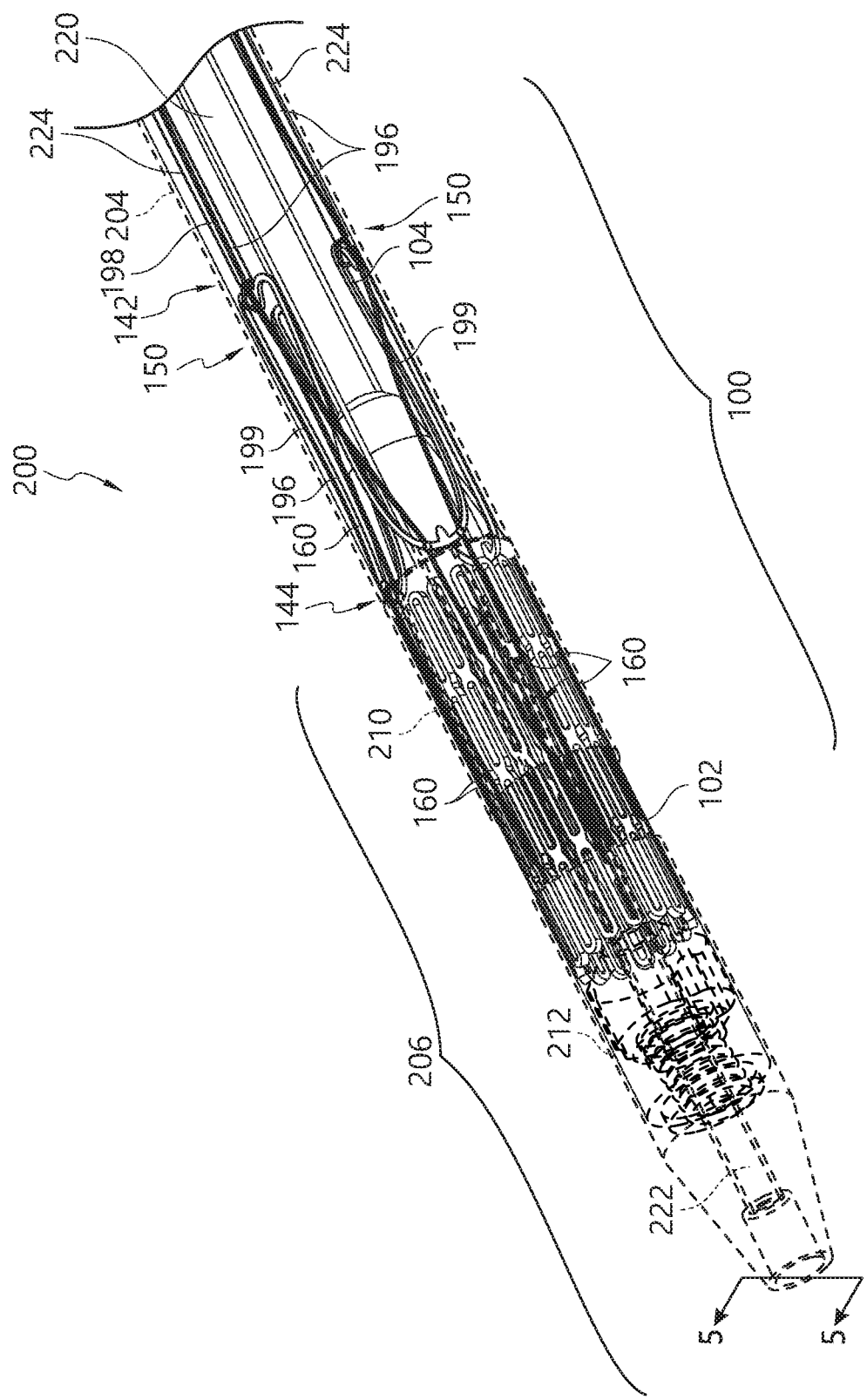
FIGS. 8A-8G show different embodiments of a link mechanism for the valve prosthesis of FIG. 2, in which the valve prosthesis is loaded onto a valve delivery device, according to some embodiments.

As illustrated in FIG. 7B, some embodiments of the delivery device can use a link mechanism 160*a* without a tension member. Thus, the link mechanism 160*a* can be attached to the support frame 102 and the valve anchor 104 and have a length configured such that in a delivery state (such as shown in FIG. 8A), the link mechanism 160*a* is generally taut. As shown, an intermediate segment 196*a* of the link mechanism 160*a* may have less slack and length between the loops 162 and 164 compared to the link mechanism 160 shown in FIG. 7A. In some embodiments, advantageously, the length of the intermediate segment 196*a* and taut state thereof may avoid the use of a tension member while still maintaining the intermediate section 196*a* in a tucked or compact configuration. Thus, the link mechanism 160*a* does not catch or become tangled during the advancement of the prosthesis 100 to the target valve annulus during the procedure.

As shown in FIG. 7B, the link mechanism 160*a* can be woven between the U-shaped member 140 and corresponding circumferential attachment points or positions at or on the support frame 102. For example, a first segment 192 of the link mechanism 160*a* can loop around the second leg 148*a* and extend towards a first attachment point on the support frame. Further, a second segment 194 of the link mechanism 160*a* can loop around the first leg 146*b* and extend towards the first attachment point on the support frame (FIG. 8B) or a second attachment point on the support frame, different from the first attachment point (FIG. 8C). In some embodiments, the link mechanism 160*a* can be tied, looped, and/or wound to the attachment points of the support frame. As illustrated, an intermediate segment 196*a* of the link mechanism 160*a* may interconnect the loop around the first leg 146*b* and the loop around the second leg 148*a*. In some embodiments, the use of the link mechanism 160*a* without a tension member may facilitate the serial "stacked" arrangement of the valve anchor 104 and the support frame 102.

When the support frame is retracted proximally relative to the valve anchor 104, the link mechanism 160 can slide along the U-shaped members 140 toward the engagement area 150. Thus, moving from the position of the link mechanism 160 in FIG. 7A (or similarly, from the position of the link mechanism 160*a* and FIG. 7B) to the position of the link mechanism 160 in FIG. 7C, the first and second segments 192, 194 are now pulled in a direction proximal to the engagement area 150. This proximally oriented pulling of the link mechanism 160, 160*a* has drawn the first and second loops 162, 164 distally into the engagement area 150. Further, in embodiments utilizing the tension member 198, during this movement (or when the support frame 102 is moved distally relative to the valve anchor 104), the tension member 198 will eventually disengage from the link mechanism 160. Additionally, because the link mechanism 160 can slide around the legs 146*b*, 148*a* via the loops 162, 164, the relative length of the intermediate segment 196 decreases and is much smaller in FIG. 7C due to the proximally oriented pulling of the link mechanism 160 (which causes more of the length of the link mechanism 160 to be drawn into the first and second segments 192, 194 than in the intermediate segment 196). Accordingly, a clinician can reduce the length of the intermediate segment 196 by pulling the support frame proximally relative to the valve anchor 104 until the first and second segments 192, 194 of the link mechanism 160 are taut. This general arrangement in illustrated in the delivery stage of FIG. 9D of U.S. Patent Application No. 62/781,537, noted above.

Thereafter, as shown by the dashed lines in FIG. 7C, the support frame can later be advanced distally relative to the valve anchor 104 and longitudinally overlap with the valve anchor 104, thus pulling the first and second segments 192', 194' of the link mechanism 160' in a distal direction relative to the engagement area 150. However, in some embodiments, due to the reduced length of the intermediate segment 196, which can be less than a width of the engagement area 150 (which can be represented by a peak-to-peak width of the curves of the second leg 148*a* and the first leg 146*b*), one or both of the loops 162, 164 will tend to remain captured within the engagement area 150 when the support frame is advanced distally relative to the valve anchor 104. In this manner, the engagement of the loops 162, 164 within the engagement area 150 can restrict or prevent the loops 162, 164 of the link mechanism 160' from sliding distally along either the first or second legs 146*b*, 148*a*. The prosthesis 100 is thus in the retained position, and the range of longitudinal and/or rotational movement of the support frame 102 relative to the valve anchor 104 is fixed as the link mechanism 160 is retained within the engagement area 150.

FIGS. 7A-7C also illustrate an embodiment of a control member or grasper of a delivery device (e.g., as shown further below in FIG. 8A) that can be used to engage the anchor retention component 170 of the engagement area 150. It is noted that, the example embodiments illustrated in FIGS. 6A and 7A-7C show that the anchor retention component 170 is disposed at the peak portion 142. However, in other embodiments, the anchor retention component 170 may be disposed in one or more other portions of the U-shaped member 140. Further, although the anchor retention component 170 is illustrated as being positioned in a valley between two peaks formed by the looping ends of the first leg 146*b* of the second U-shaped member 140*b* and the second leg 148*a* of a first U-shaped member 140*a*, the valve anchor 104 can be configured to comprise a rounded, single-peak section (i.e., without dual peaks or an intermediate valley) at which the anchor retention component 170 is formed between the first leg 146*b* and the second leg 148*a*. The function and structure of the grasper as discussed further herein, for example, with respect to FIGS. 8-9B.

In accordance with some embodiments, the link mechanism 160 can have a fixed length. The fixed length of the link mechanism 160 can restrict longitudinal, circumferential (i.e., rotational), and/or radial movement that the valve anchor 104 relative to the support frame 102 when the prosthesis 100 is in either the slidable or retained positions. Thus, the link mechanism 160 can comprise a material that is not stretchable. In some embodiments, the link mechanism 160 can comprise a suture, made from materials known in the art. The fixed length of the link mechanism 160 can be configured to ensure that when in the retained position, the support frame 102 is advanced to a maximum distal position relative to the valve anchor 104 that provides an optimal placement of the support frame 102 relative to the valve anchor 104.

Further, in some embodiments, the link mechanism 160 can comprise a single, continuous strand of material that is interwoven with the support frame 102 and the valve anchor 104 at multiple locations, as illustrated in FIG. 2. In such embodiments, the single, continuous strand can be tied at its ends to a coupling point(s) of the support frame 102 and looped or wound around other coupling points of the support frame 102 and the valve anchor 104 at (many or all) other locations. When looped or wound around a coupling point of the support frame 102 or the valve anchor 104, the continuous-stranded link mechanism 160 can slide or move relative to the support frame 102 or valve anchor 104, which provides various advantages that are discussed herein.

In some embodiments using a single, continuous link mechanism 160 and a single U-shaped member of the valve anchor, a loop length of the continuous link mechanism 160 can be greater than the sum of (i) a compressed circumference of the support frame and (ii) two times a longitudinal length of the support frame. Further, in some embodiments using a single, continuous link mechanism 160 and a plurality of U-shaped members, a loop length of the continuous link mechanism 160 can be between about 80% to about 120% of a sum of (i) a compressed circumference of the support frame and (ii) four times a longitudinal length of the support frame. For example, in some embodiments, a single, continuous link mechanism 160 can be interwoven with three U-shaped members of the valve anchor, and a loop length of the continuous link mechanism 160 can be between about 80% to about 120% of a sum of (i) a compressed circumference of the support frame and (ii) six times a longitudinal length of the support frame.

In some embodiments, the link mechanism 160 can comprise multiple, individual lengths of material that are coupled at one end to the support frame 102 and at another end to the valve anchor 104. For example, the link mechanism 160 can be fixedly attached (i.e., so as to not move or slide) at one end to the valve anchor 104 and slidably attached at the other end to the support frame 102 to provide the movement and capturing of the link mechanisms 160 within the engagement areas 150, as discussed above.

Whether the link mechanism 160 comprises a single, continuous strand or multiple, individual lengths of material, a longitudinal length or extent of the link mechanism(s) 160 can be between about 110% and about 170%, such as less than 170%, 160%, 150%, 140%, 130%, 120%, or 110%, of a longitudinal length of the valve anchor when the valve anchor and the support frame are in the compressed configuration. Further, a longitudinal length or extent of the link mechanism(s) 160 can be between about 40% and about 130%, such as less than 130%, 120%, 110%, 100%, 90%, 80%, 70%, 60%, 50%, or 40% of a longitudinal length of the valve anchor when the valve anchor and the support frame are in the expanded configuration.

The present disclosure also describes various aspects of a delivery device for, e.g., transfemoral delivery of a valve prosthesis. The delivery device can support a valve prosthesis, such as the prosthesis 100 discussed above. The delivery device can comprise a proximal sheath component, a distal carrier assembly, and a control unit, wherein the distal carrier assembly is distal to the proximal sheath component, and the proximal sheath component is distal to the control unit. In some embodiments, the distal carrier assembly can comprise a conical or tapered end portion. The proximal sheath component and the distal carrier assembly can at least partially enclose the support frame and the valve anchor of the valve prosthesis prior to and during delivery of the valve prosthesis. The configuration of the delivery device with respect to the proximal sheath component and the distal carrier assembly, the support frame, and the valve anchor can allow the valve anchor and the support frame to be loaded or positioned serially along the longitudinal axis in a compact condition, thus enabling the delivery device to achieve a minimal crossing profile to reduce any difficulty in advancing the delivery device to the target location within the patient. The distance from which the valve anchor may be serially displaced from the support frame is highly variable. This may allow the user to minimize the radius of the delivery device which must be advanced through, for example, arteries and veins. Further, the valve anchor can be expanded and positioned independent of the support frame prior to positioning and releasing the support frame, as described in greater detail below. Additionally, a link mechanism that interconnects the valve anchor to the support frame can advantageously facilitate reliable positioning of the support frame relative to the valve anchor.

Referring now to FIGS. 8A-10H, the prosthesis 100 is illustrated loaded onto a delivery device 200. Using the delivery device 200, the valve prosthesis 100 can be delivered and expanded component by component in order to achieve the expanded configuration illustrated in FIG. 2. During this component-by-component expansion process (illustrated in the delivery stages of FIGS. 11A-11F of U.S. Patent Application No. 62/781,537, noted above), the ability of the link mechanism 160 to move along the U-shaped members of the valve anchor 104 provides several distinct benefits. For example, one of these benefits is illustrated in FIGS. 8A-9E, which is that during delivery of the valve prosthesis 100, it is advantageous to have the valve anchor 104 positioned serially from the support frame 102 in order to achieve a minimal outer profile for the delivery device. This serial positioning allows the delivery device 200 to have a minimized outer diameter, which can allow the delivery device 200 to be more easily advanced through blood vessels.

As shown in FIGS. 8A-9E, the delivery device can carry the support frame, the valve anchor, and the link mechanism of the valve prosthesis. For example, FIG. 8A shows that the delivery device 200 can carry the support frame 102, the valve anchor 104, and the link mechanism 160 of the valve prosthesis 100. The delivery device 200 can comprise one or more elongate core members that extend along a longitudinal axis of the delivery device 200.

The delivery device 200 can also comprise a proximal sheath component 204 (shown in dashed lines in FIG. 8A to illustrate the underlying components and features of the prosthesis 100 and the delivery device 200) and a distal carrier assembly 206 (also shown in dashed lines in FIG. 8A to illustrate the underlying components and features of the prosthesis 100 and the delivery device 200). The proximal sheath component 204 can be coupled to and extend distal to a control unit (illustrated in FIGS. 13A-13H of U.S. Patent Application No. 62/781,537, noted above), through which the clinician can control movement of the various components of the delivery device 200.

The distal carrier assembly 206 can be a two-part component that is configured to house at least one of the valve anchor or the support frame. The distal carrier assembly 206 comprise a proximal enclosure 210 (shown in dashed lines) and a distal enclosure 212 (shown in dashed lines). The proximal enclosure 210 can be coupled to a first core member 220, and the distal enclosure 212 can be coupled to a second core member 222. In some embodiments, the distal enclosure 212 can be threadedly and/or adhesively coupled or bonded to the second core member 222. For example, the second core member 222 may include a hollow shaft. The first and second core members 220, 222 can allow a clinician to manipulate the relative positions of the proximal and distal enclosures 210, 212. Together, the proximal sheath component 204 and the distal carrier assembly 206 can collectively house the valve anchor 104 and the support frame 102, respectively, during delivery of the valve prosthesis 100 to a target location within the body (e.g., discussed herein as the aortic valve annulus) and be actuated by the clinician to position and release the valve prosthesis 100. Further, the distal enclosure 212 can comprise a conical or tapered anterior or distal portion to facilitate movement through the vasculature. In some embodiments, the distal carrier assembly 206 can be referred to as a two-part distal enclosure or a split nose cone assembly. Optionally, the distal enclosure 212 can comprise, be formed from, or include features that comprise a radiopaque material such as platinum.

FIGS. 8A-9E show the delivery device 200 prior to delivery of the prosthesis 100, in a loaded configuration. As shown, the first and second core members 220, 222 extend through the delivery device 200 and are coupled at their distal ends to proximal and distal enclosures 210, 212, respectively, of the distal carrier assembly 206. As illustrated in these figures, the second core member 222 can be disposed within a lumen of the first core member 220 and slidable therewithin. Accordingly, the proximal enclosure 210 of the distal carrier assembly 206, as well as the proximal sheath component 204, can be slidable relative to the second core member 222 and the distal enclosure 212.

As also shown, the proximal sheath component 204 can extend distally over the valve anchor 104 to enclose the valve anchor 104 within a lumen of the proximal sheath component 204 and maintain the valve anchor 104 in a compressed state. The lumen of the proximal sheath component 204 may also be referred to as a proximal sheath lumen. The proximal sheath component 204 can be retracted relative to the valve anchor 104 in order to permit the base portions of the U-shaped members of the valve anchor 104, thereafter to expand and later be maneuvered into position within the aortic sinuses.

As also illustrated in FIGS. 8A-9E (see also FIGS. 7A-7C), the delivery device 200 can comprise at least one grasper 224 that can engage with and control positioning of the valve anchor 104. The grasper 224 can comprise distal ends, pinchers, or hooks 226 at its distal end that can be coupled to the peak portions of the U-shaped members of the valve anchor 104. For example, the pinchers 226 of the grasper 224 can be coupled to the anchor retention component 170 at the engagement area of the valve anchor 104 to cause the grasper 224 to be engaged with the valve anchor 104. The number of graspers 224 preferably equals the number of engagement areas 150 or U-shaped members 140 of the valve anchor 104. Each of the graspers 224 can comprise a tubular enclosure 228 through which a pair of wires, which terminate in the pinchers or hooks 226, passes. The wires can be pulled proximally relative to the tubular enclosure 228 in which the wires are housed in order to tighten the pinchers 226 around the anchor retention component 170, thus engaging the valve anchor 104. In order to release the pinchers 226, the wires can be shifted distally relative to the tubular enclosure 228 thereby allowing the pinchers 226 to spring open radially and release the anchor retention component 170. The distal end of each of the graspers 224 can enclose or be coupled to a hook of the valve anchor 104.

The interconnection between the distal ends, pinchers, or hooks 226 of the graspers 224 and the valve anchor 104 can permit the valve anchor 104 of the support frame 102 to be held in a stationary and/or compressed position relative to or within the proximal sheath component 204. For example, as discussed with regard to FIGS. 7G-7I of U.S. Patent Application No. 62/781,537, noted above, this engagement can maintain the engagement areas 150 in a common plane 152, oriented generally perpendicular relative to the longitudinal axis of the delivery device 200. Additionally, when the proximal sheath component 204 is proximally retracted relative to the distal ends of the graspers 224, the valve anchor 104 can begin to expand; however, the engagement between the graspers 224 and the engagement areas 150 can allow a clinician to push, pull, or rotate the valve anchor relative to the delivery device 200 before fully releasing the valve anchor 104 from engagement with the delivery device 200. For example, this can allow the clinician to rotate or push the base portions 144 of the valve anchor 104 into the nested position within the aortic sinuses, as discussed above. Thereafter, once in the nested position, the engagement areas 150 of the valve anchor 104 can be released from the pinchers 226 of the graspers 224, and the valve anchor 104 can fully expand and be released into apposition with the native valve annulus.

Figure 8B:
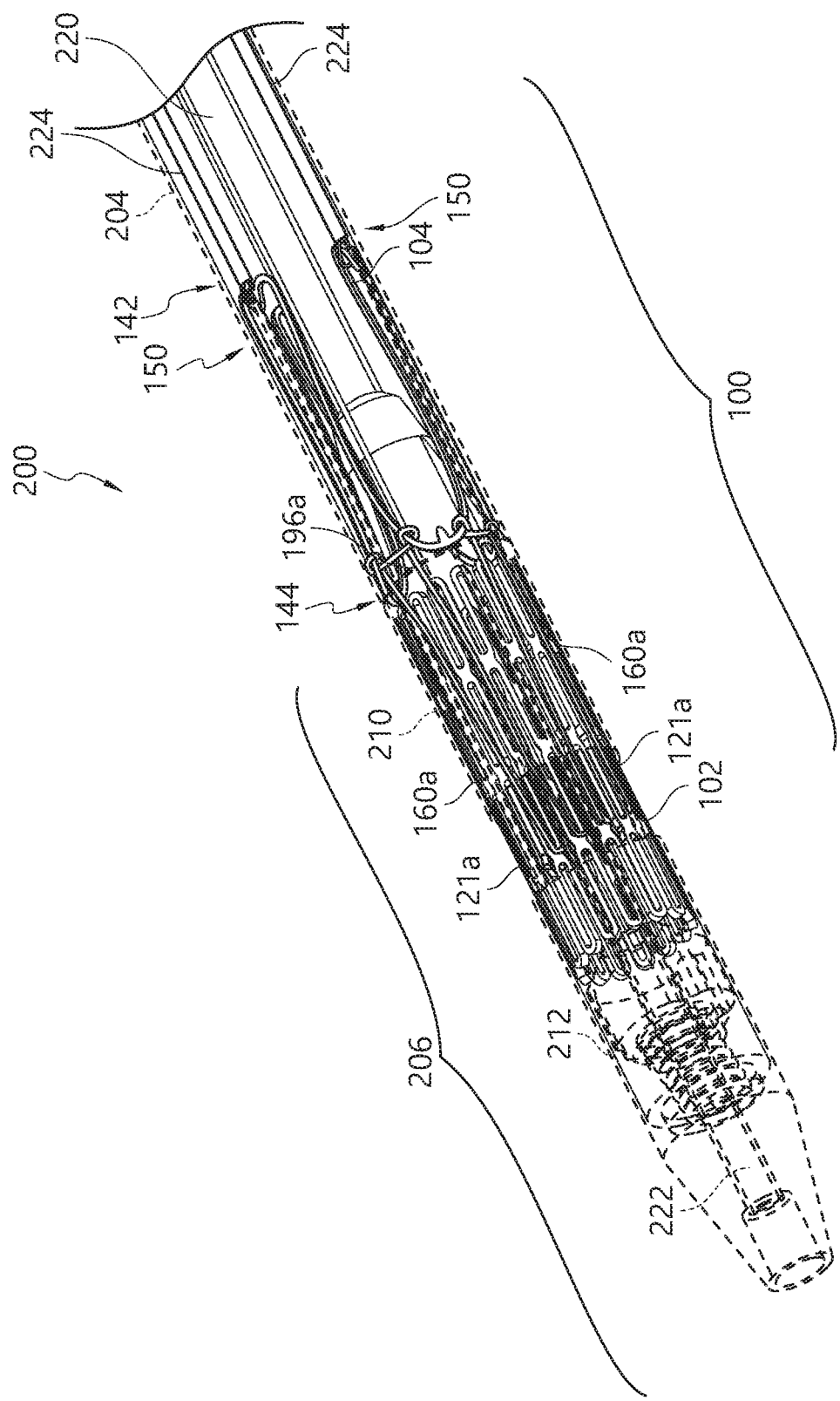
Figure 8C:
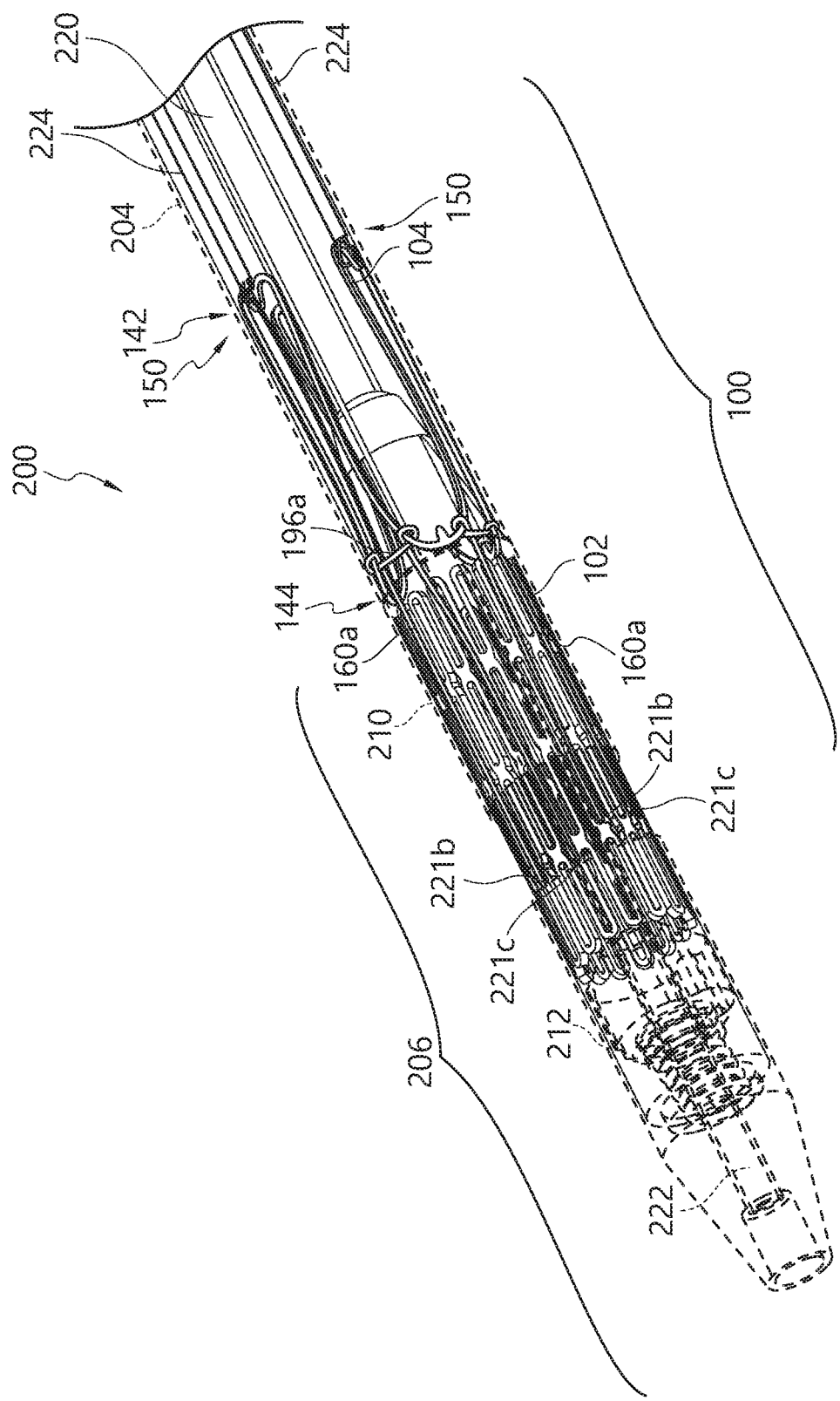

In some embodiments, as illustrated in FIGS. 8B and 8C, the delivery device 200 can include a link mechanism 160a that interconnects the support frame 102 and the valve anchor 104 without a tension member. As illustrated in FIG. 8B, a link mechanism 160a can be woven between the support frame 102 and the valve anchor 104. In the depicted example of FIG. 8B, the link mechanism 160a can be coupled to an attachment point 221a on the support frame 102, extend toward and loop around a first leg of the valve anchor 104, then toward a second leg of the valve anchor 104, and then extends back toward the attachment point 221a. The link mechanism 160a can be tied, looped, or wound around the support frame 102 at the attachment point 221a. In some embodiments, one or more of the ties, loops, or windings of the link mechanism 160a can be fixed relative to or capable of sliding along the leg(s) of the valve anchor 104.

In some embodiments, as illustrated in FIG. 8C, the link mechanism 160a can attach to the support frame 102 at two different attachment points 221b, 221c. For example, as shown in FIG. 8C, the link mechanism 160a can be coupled to the support frame 102 at a first attachment point 221b of the support frame 102, extend toward and loop around the first leg of the valve anchor 104, then extend toward and loop around the second leg of the valve anchor 104, and then extend toward a second attachment point 221c of the support frame 102. An intermediate segment 196a can interconnect the loops around the first leg and the second leg of the valve anchor 104.

Figure 8D:
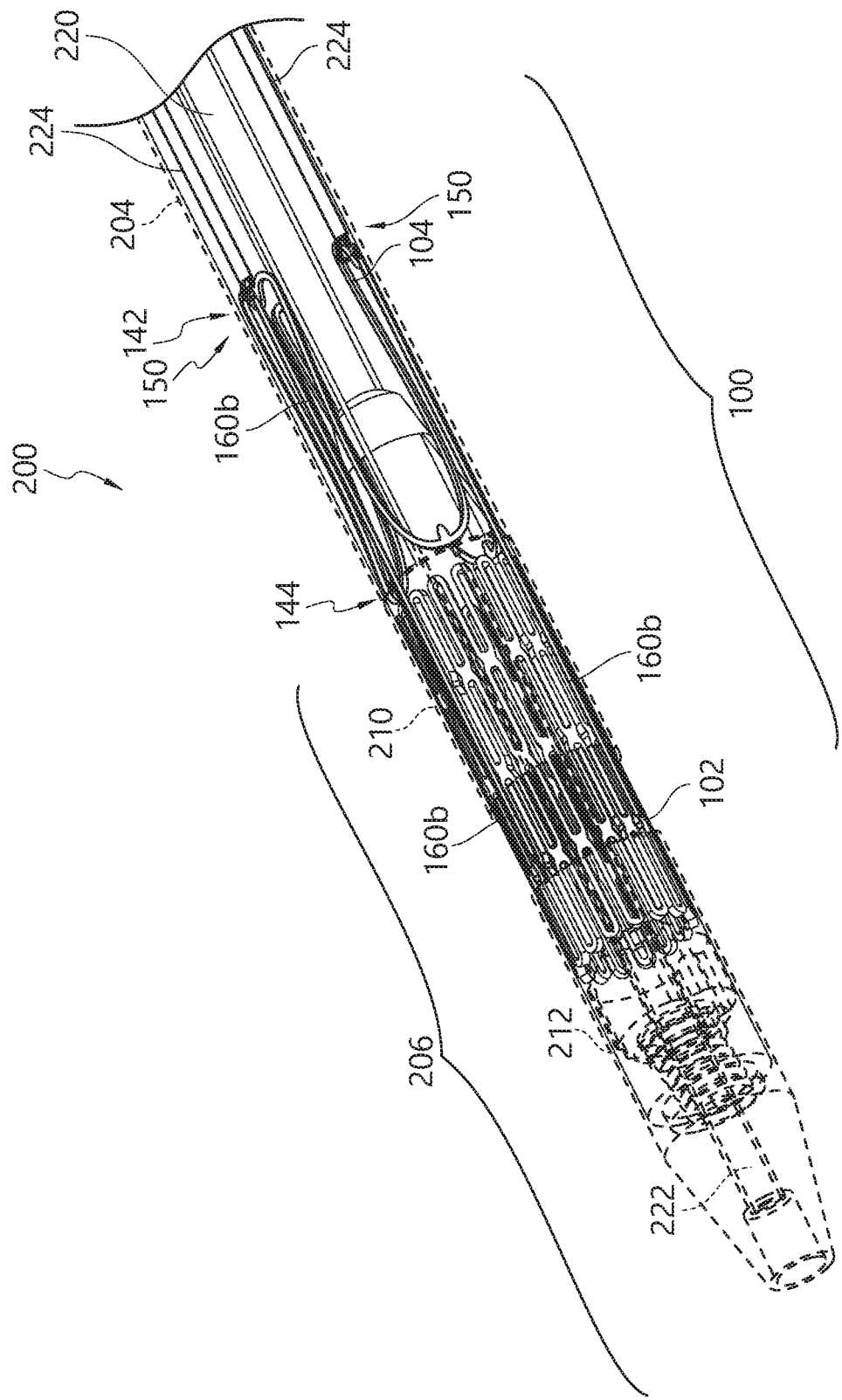
Figure 8E:
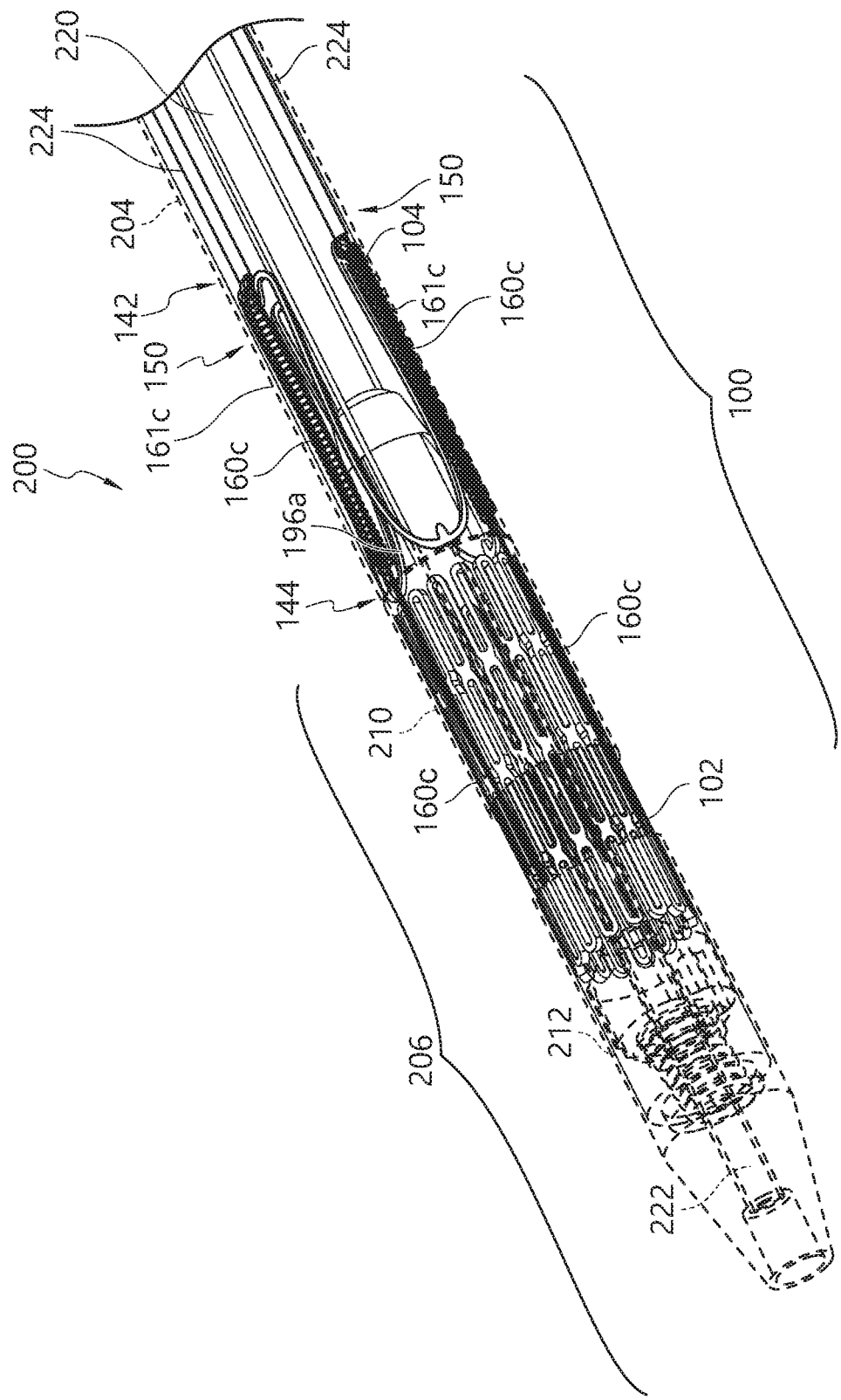

In some embodiments, as illustrated in FIGS. 8D and 8E, the delivery device 200 can include a link mechanism 160b that interconnects the support frame 102 and the valve anchor 104 while being fixed or coupled relative to the leg(s) of the valve anchor 104. As illustrated in FIG. 8D, the link mechanism 160b can be coupled to an attachment point on the support frame 102 and extend toward an engagement area 150 of the valve anchor 104. The link mechanism 160b can be tied, looped, wound or otherwise attached to the support frame 102 and the valve anchor 104 at the attachment points.

In the depicted example, the link mechanism 160b can be an elastic interconnect formed from silicone, polyurethane, or any other suitable elastic material. When the support frame 102 is moved relative to the valve anchor 104, the link mechanism 160b can stretch, flex, or otherwise elastically stretch. As the link mechanism 160b stretches, the support frame 102 can move longitudinally and/or rotationally relative to the valve anchor 104.

In some embodiments, as illustrated in FIG. 8E, the delivery device 200 can include a link mechanism 160c that interconnects the support frame 102 and the valve anchor 104. The link mechanism 160c can include a resilient or coiled portion 161c. For example, as shown in FIG. 8E, the coiled portion 161c is proximal to the engagement area 150. The coiled portion 161c can allow for the link mechanism 160c to stretch to a longer length and/or minimize length of the link mechanism 160c in an unstretched state. In some embodiments the coiled portion 161c can be a spring mechanism and may include laser cut patterns.

Figure 8F:
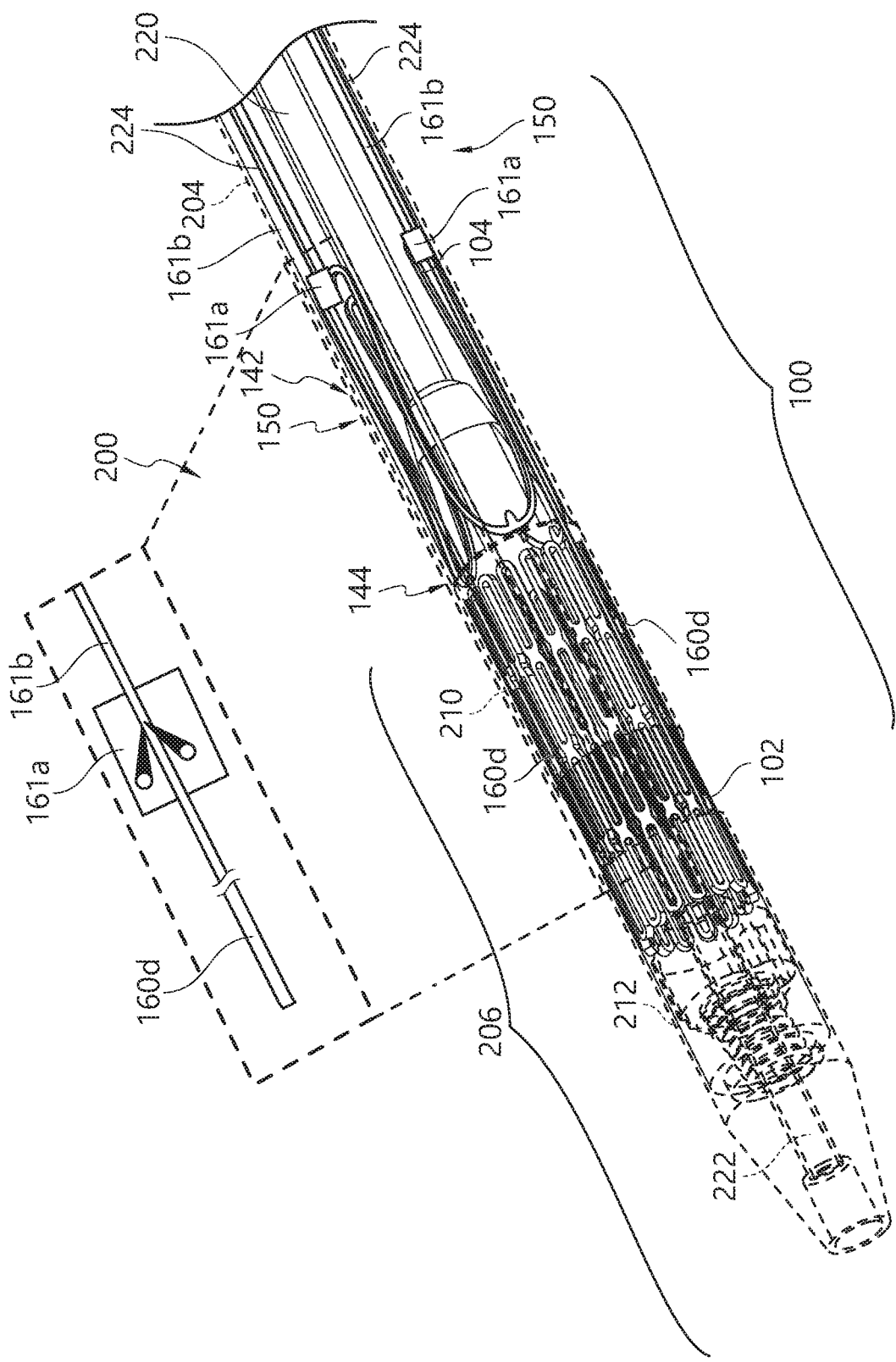
Figure 8G:
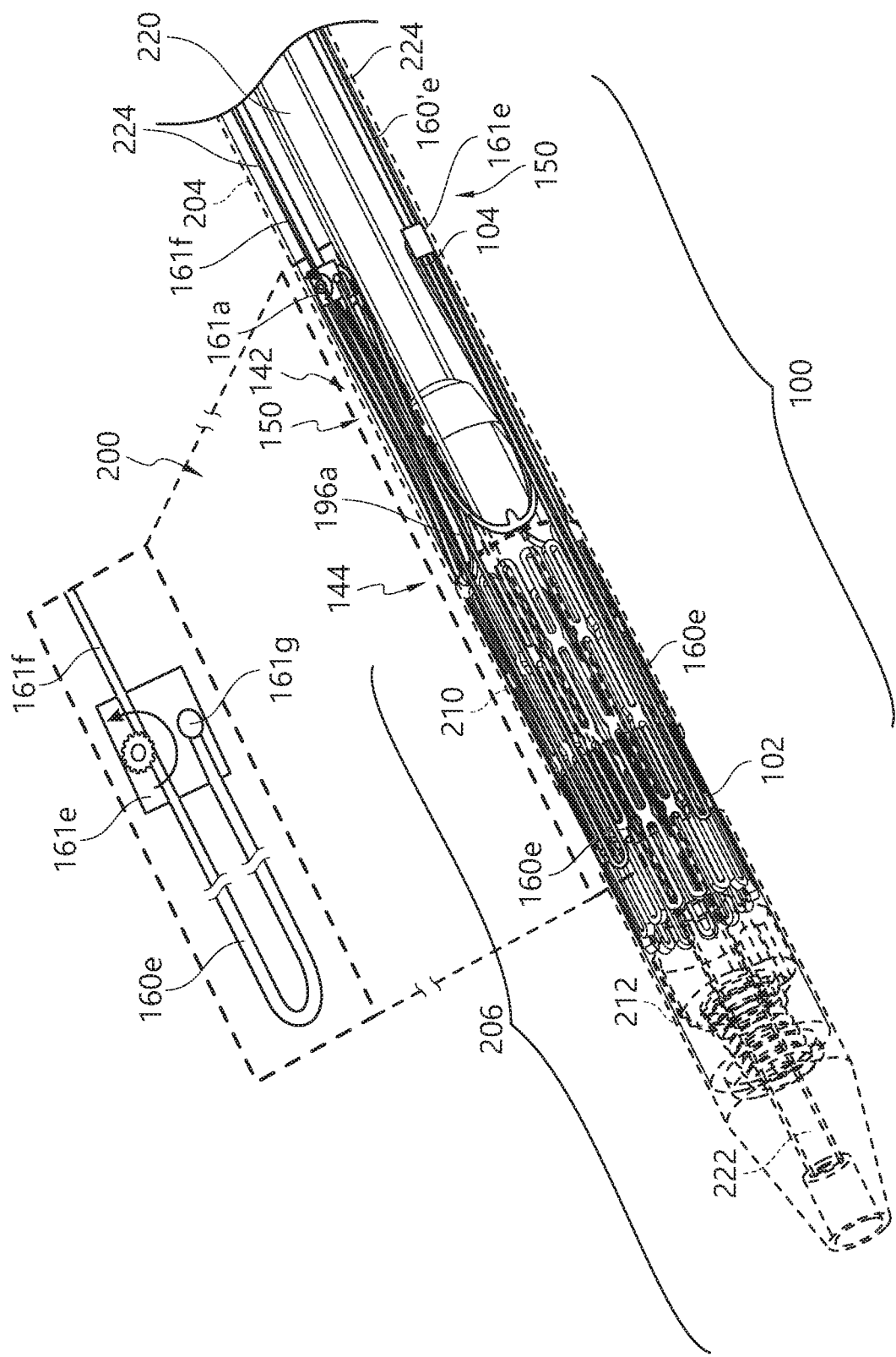

In some embodiments, as illustrated in FIGS. 8F and 8G, the delivery device 200 can include a link mechanism 160d that interconnects the support frame 102 and the valve anchor 104 and a one-way interconnect to maintain tension on the link mechanism 160a.

As illustrated in FIG. 8F, a link mechanism 160d can be coupled to the support frame 102, e.g., at an attachment point thereof, and extend toward an engagement area 150 of the valve anchor 104. The link mechanism 160d can be received by a one-way interconnect 161a to permit movement of the link mechanism 160d in a proximal direction through the interconnect 161a while restricting or preventing distal advancement or return of the link mechanism 160d through the interconnect 161a. In some embodiments, the link mechanism 160d can comprise a proximal actuation portion 161b that is coupled or extends to the link mechanism 160d. For example, the link mechanism 160d and the proximal actuation portion 161b can be sections of a continuous line, wire, or suture that passes through the one-way interconnect 161a. Further, the link mechanism 160d and the proximal actuation portion 161b can be flexible or rigid.

In accordance with some embodiments, the one-way interconnect 161a can comprise a ratcheting mechanism. For example, as illustrated in the inset figure of FIG. 8F, the interconnect 161a can comprise a body having an aperture through which the link mechanism 160d can pass, and the ratcheting mechanism can have a toothed structure extending into the aperture that permits movement of the link mechanism 160d in one direction, but engages the link mechanism 160d to restrict movement in an opposite direction.

In use, for example, the clinician can distally advance the valve anchor 104 relative to the support frame 102 (using a motion and features of the embodiments disclosed herein), which can result in some slack in the link mechanism 160d. The clinician can then grasp and pull the proximal actuation portion 161b, which will cause the link mechanism 160d to be drawn proximally through (e.g., ratcheted through) the interconnect 161a, thereby reducing the length of the link mechanism 160d between the interconnect 161a and the attachment point on the support frame 102. Accordingly, the clinician can draw the support frame 102 and the valve anchor 104 together upon exerting a proximally oriented force on the proximal actuation portion 161b while maintaining the valve anchor 104 stationary. This motion and ratcheting of the link mechanism 160d can restrict motion of the valve anchor 104 relative to the support frame 102. In this manner, as the valve anchor 104 is drawn towards the support frame 102, the relative longitudinal positions of these components can be restricted or fixed in a desirable relative position in anticipation of releasing the prosthesis at the implantation site.

In some embodiments, as illustrated in FIG. 8G, a link mechanism 160e can be coupled to the support frame 102, e.g., at an attachment point thereof, and extend toward an engagement area 150 of the valve anchor 104. The link mechanism 160e can be woven between the support frame 102 and the valve anchor 104 (e.g., the link mechanism 160e can extend from the valve anchor 104 and be looped through the support frame 102, similar to or such as by a pulley-type configuration).

In the depicted example of FIG. 8G, the link mechanism 160e can be coupled to the one-way interconnect 161e, extend toward and loop around the support frame 102 and then toward the one-way interconnect 161e disposed proximal to the engagement area 150 of the valve anchor 104 in a pulley mechanism. Similarly, the link mechanism 160e can be received by the one-way interconnect 161e to permit movement of the link mechanism 160e in a distal direction through the interconnect 161e while preventing the proximal movement of the link mechanism 160e through the interconnect 161e. In some embodiments, the link mechanism 160e can comprise a proximal actuation portion 161f that is coupled or extends to the link mechanism 160e. For example, the link mechanism 160e and the proximal actuation portion 161f can be sections of a continuous line, wire, or suture that passes through the one-way interconnect 161e. Further, the link mechanism 160e and the proximal actuation portion 161f can be flexible or rigid. In some embodiments, an end 161g of the link mechanism 160e can be coupled to the interconnect 161e to secure the link mechanism 160e thereto, thus enabling the clinician to draw the support frame 102 and the valve anchor 104 together upon exerting a proximally oriented force on the proximal actuation portion 161f while maintaining the support frame 102 or the valve anchor 104 stationary.

In accordance with some embodiments, the one-way interconnect 161e can comprise a rotating ratcheting mechanism. For example, as illustrated in the inset figure of FIG. 8G, which illustrates the pulley mechanism of the interconnect 161e, the interconnect 161e can comprise a body having an aperture through which the link mechanism 160e can pass, and the ratcheting mechanism can have a toothed wheel structure extending into the aperture that permits movement of the link mechanism 160e in one direction, but engages the link mechanism 160e to restrict movement in an opposite direction.

In use, for example, the clinician can distally advance the valve anchor 104 relative to the support frame 102 (using a motion and features of the embodiments disclosed herein), which can result in some slack in the link mechanism 160e. The clinician can then grasp and pull the proximal actuation portion 161f, which will cause the link mechanism 160e to be drawn proximally through (e.g., ratcheted through) the interconnect 161e, thereby reducing the length of the link mechanism 160e between the interconnect 161e and the attachment point on the support frame 102. Alternatively, the clinician can simply pull proximally on the proximal actuation portion 161f to draw or force distal advancement of the valve anchor 104 relative to the support frame 102, which can reduce the length of the link mechanism 160e between the interconnect 161e and the attachment point on the support frame 102. Either of these types of motion and ratcheting of the link mechanism 160e can restrict motion of the valve anchor 104 relative to the support frame 102. In this manner, as the valve anchor 104 can be drawn towards the support frame 102, the relative longitudinal positions of these components can be restricted or fixed in a desirable position in anticipation of releasing the prosthesis at the implantation site.

FIG. 9A-9E illustrate the various positions and actuation of link mechanisms during a deployment sequence of the valve prosthesis. The link mechanism attachment pattern can vary from that discussed and illustrated with respect to other embodiments disclosed herein; however, the embodiments shown in FIG. 9A-9E illustrated movement and positioning of the link mechanism and related features that can be incorporated into one or more embodiments disclosed herein.

For example, FIGS. 9A and 9B illustrate the delivery device 200 in a configuration in which the proximal sheath component 204 is proximally retracted relative to the valve anchor 104, which permits the valve anchor 104 to begin to expand from a compressed, loaded configuration. As illustrated in FIGS. 9A and 9B, the valve anchor 104 can optionally be configured such that the U-shaped member's base portion 144 comprises a link motion limiter 240a (see also 240b) that extends from a medial location of the base portion 144. The link motion limiter 240a, 240b can provide an enlarged profile of the wireframe structure of the valve anchor 104 that restricts or prevents movement of a loop (see e.g., loops 162 and 164, also shown in FIG. 7A) of the link mechanism 160 as the loop slides along the base portion 144 of the valve anchor 104.

For example, the link motion limiter 240a can tend to prevent the loops of the link mechanism 160 from both sliding onto a single leg of the U-shaped member 140. This will allow the loops (e.g., loops 162, 164) of the link mechanism 160 to move only toward the respective engagement areas of the valve anchor 104, thereby properly positioning the link mechanism 160 within the respective engagement areas and ensuring proper motion and deployment of the valve anchor 104.

In some embodiments, each of the first, second, and third U-shaped members of the valve anchor 104 can comprise a respective link motion limiter. Further, the link mechanism 160 can be coupled to each of the respective U-shaped members on opposing sides of the respective link motion limiters (see e.g., link motion limiter 240a and loops 162, 164 in FIG. 9B).

Furthermore, in some embodiments, the link motion limiter 240a, 240b can extend from the base portion 144 in a proximal direction toward the peak portions of the valve anchor 104, as shown in FIGS. 9A and 9B. However, the link motion limiter 240a, 240b can also extend from the base portion 144 in a distal direction away from the peak portions of the valve anchor 104. As can be appreciated, while the link motion limiter 240a, 240b extends from the base portion 144, the U-shape members of the valve anchor 104 generally retain and can be considered "u-shaped." Optionally, the link motion limiter can include features to enable functionality as a latch, clasper tang or other attachment point for a grasper component.

FIGS. 9A and 9B also illustrate that the link mechanism 160 can define a weave pattern that interconnects the valve anchor 104 with the support frame 102. For example, the link mechanism 160 extends (i) from a first circumferential attachment position 242 on the support frame 102, (ii) to a first leg 146b of a first U-shaped member 140a (on a first side of the link motion limiter 240a of the first U-shaped member 140a), (iii) then hooking into the flexible loop 199 of the tension member 198 and then to a second leg 148a of the first U-shaped member 140a (on a second side of the link motion limiter 240a of the first U-shaped member 140a), (iv) then to a second circumferential attachment position 244 on the support frame 102, and (v) then to a first leg 146c of a second U-shaped member 140b on a second side of the link motion limiter 240b. The link mechanism can continue in this pattern and extend to a second leg of a third U-shaped member and then to a third circumferential attachment position on the support frame 102 (not shown).

As also illustrated in FIG. 9A, the first and second circumferential attachment positions 242, 244 can be located adjacent to, within, or along a medial portion of the support frame 102. In particular, the first and second circumferential attachment positions 242, 244 can be exposed through a window or gap 248 between the proximal and distal enclosures 210, 212 when the prosthesis 100 is in the compressed or delivery configuration. However, the first and second circumferential attachment positions 242, 244 can be located adjacent to, within, or along a proximal or distal end portion of the support frame 102 such that the first and second circumferential attachment positions 242, 244 are covered by one of the proximal or distal enclosures 210, 212 during delivery to the target location.

FIG. 9C is an enlarged detail view of the valve prosthesis and delivery device of FIG. 8B. FIG. 9C illustrates a delivery device 200 with link mechanisms 160a, 160b without tension members. Each link mechanism 160a can define a weave pattern that interconnects the valve anchor 104 with the support frame 102. For example, the link mechanism 160a extends (i) from a first circumferential attachment position (e.g., 242, as in FIG. 9A) on the support frame 102, (ii) to a first leg 146b of a first U-shaped member 140a (on a first side of the link motion limiter 240b of the first U-shaped member 140a), (iii) then extending directly to a second leg 148b of a second U-shaped member 140c (on a second side of a link motion limiter 240c of the second U-shaped member 140c), (iv) then back to the first circumferential attachment position (e.g., 242, as in FIG. 9A) on the support frame 102 (or alternatively, to a different circumferential attachment point on the support frame 102).

Additional link mechanisms 160b, 160c can weave a similar pattern between the U-shaped members and circumferential attachment positions on the support frame 102.

FIG. 9D illustrates a delivery device 200 with a diamond shaped link motion limiter 240c that extends from a medial location of the base portion 144. In the depicted example, the link motion limiter 240c can provide an elongated diamond shaped profile of the wireframe structure of the valve anchor 104 that restricts or prevents movement of a loop 162, 164 of the link mechanism 160d sliding along the base portion 144 of the valve anchor 104. For example, the link motion limiter 240c can tend to prevent the loops 162, 164 of the link mechanism 160d from both sliding onto a single leg of the U-shaped member 140, while allowing the loops 162, 164 of the link mechanism 160d to freely move toward the respective engagement areas of the valve anchor 104, thereby properly positioning the link mechanism 160d within the respective engagement areas 150 and ensuring proper motion and deployment of the valve anchor 104.

FIG. 9E illustrates a delivery device 200 with a barrier suture 240d for maintaining a loop (e.g., 162, 164) of a link mechanism on a single leg of a U-shaped member. The barrier suture 240d can be a strand of material that is attached to the valve anchor 104. However, the barrier suture 240d can be formed as a single, continuous portion of the valve anchor 104, for example, as a single, continuous piece of material.

In FIG. 9E, the valve anchor 104 comprises a plurality of barrier suture 240d, which extend from medial locations 144a of the U-shaped members 140a, 140b, 140c toward respective legs thereof adjacent to the engagement area of each U-shaped member. For each U-shaped member, for example, a barrier suture 240d can extend from a first location, adjacent to a first engagement area 150b on a first leg 146b, proximal to a medial location 144a of the base portion and, whether as a single, continuous strand or as a second, separate strand, the barrier suture 240d can extend from the medial location 144a to a second location on a second leg 148a, proximal to the second engagement area 150a.

In the depicted example of FIG. 9E, the barrier suture 240d restricts or prevents movement of loops 162, 164 of the link mechanism 160d from sliding past or beyond the medial location 144a of the valve anchor 104 onto a different leg 146b, 148a of the U-shaped member 140a. For example, the barrier suture 240d can tend to prevent the loops 162, 164 from both sliding onto the same leg 146b, 148a of the U-shaped member 140a, while allowing the loops 162, 164 to freely move toward the respective engagement areas 150a, 150b of the valve anchor 104, thereby properly positioning the link mechanism 160 within the respective engagement areas and ensuring proper motion and deployment of the valve anchor 104.

FIGS. 10A-10H illustrate optional aspects of a delivery device, according to at least one embodiment. These figures do not illustrate all of the components of the delivery device that can be incorporated into an embodiment. However, the features illustrated in these figures can be incorporated into embodiments of the delivery device to facilitate engagement with the valve anchor and/or facilitate delivery and control of the valve anchor during implantation and release of the valve anchor at the target location.

For example, FIGS. 10A-10D illustrate an embodiment of a delivery device 200a that comprises a grasper mechanism. The grasper mechanism can be used to securely couple a portion of the valve anchor with the delivery device to permit the clinician to control movement, operation, and deployment of the valve anchor. The grasper mechanism can engage one or more portions or structures of the valve anchor using a variety of coupling mechanisms, which can use attachment means including mechanical engagement, dissolvable structures, chemically reactive degradable structures, electrolytically degradable structures, and the like.

In some embodiments, the grasper mechanism can be a tubular grasper mechanism. The delivery device 200a, shown in FIG. 10A, can comprise a grasper 224a that can engage with and control the longitudinal position of the valve anchor 104a, as shown in FIG. 10A. FIGS. 10B and 10C illustrate states of disengagement and features of components of the grasper 224a, which are hidden in FIG. 10A due to the grasper 224a and the valve anchor 104a being in an engaged configuration in FIG. 10A.

As shown in FIGS. 10B and 10C, the grasper 224a of the delivery device 200a can comprise an engagement wire 179 that is movable within a lumen of a tubular enclosure 228a. The valve anchor 104a can be configured to comprise a clasper tang 170a extending from an engagement area 150d of the valve anchor 104a. The engagement wire 179 can comprise a distal end portion that includes pins, ridges, or protrusions 226a that can be coupled to the engagement structure 172a of the clasper tang 170a at the engagement area of the valve anchor 104a.

When engaged together, the engagement wire 179 and the clasper tang 170a can be proximally drawn into the lumen of the tubular enclosure 228a, which secures the engagement wire 179 and the clasper tang 170a relative to each other in both radial and longitudinal directions. However, when the engagement wire 179 and the clasper tang 170a are moved outside of the lumen of the tubular enclosure 228a, as shown in FIG. 10D, the engagement wire 179 and the clasper tang 170a can be disengaged as the valve anchor 104a and the clasper tang 170a expand radially, thereby disengaging the clasper tang 170a from the engagement wire 179.

Referring to FIG. 10A, each wire 179 can be pulled or positioned proximally within or relative to the lumen of its tubular enclosure 228a in which the wires 179 are housed. In some embodiments, the engagement area of the valve anchor 104a is positioned within the tubular enclosure 228a, securing the ridges or protrusions 226a within the openings of the clasper tangs 170a by limiting the relative motion of the ridges or protrusions 226a with respect to the openings of the clasper tangs 170a, thus engaging the valve anchor 104a.

In some embodiments, the clasper tangs 170a can be coupled along a radial outer region of the engagement wires 179, as shown in FIG. 10B. Further, the cross-sectional area of the tubular enclosure 228a is small enough to prevent the protrusions 226a from disengaging from the clasper tangs 170a in a radial direction while allowing the collective cross-section of the engaged valve anchor 104a to move within or relative to the tubular enclosure 228a while maintaining the longitudinal locking or engagement between the engagement wire 179 and the clasper tang 170a.

In accordance with at least one embodiment, the graspers 224a can permit a clinician to push, pull, or rotate the valve anchor 104a relative to the delivery device 200a before fully releasing the valve anchor 104a from engagement with the delivery device 200a.

Referring again to FIG. 10B, each wire 179 can be advanced distally within or relative to the lumen of its tubular enclosure 228a such that the ridges or protrusions 226a and the openings of the clasper tangs 170a are outside of the lumen of the tubular enclosure 228a. By advancing each wire 179 relative to its tubular enclosure 228a, so that the protrusions 226a and the clasper tangs 170a are outside of the lumens of the tubular enclosures 228a, the clasper tangs 170a can begin to self-expand and radially separate from the protrusions 226a, thereby detaching from the protrusions 226a to release the valve anchor 104a, as shown in FIG. 10C. Upon release of the valve anchor 104a, the wires 179 can be retracted into the tubular enclosure 228a, as shown in FIG. 10D.

FIGS. 10E and 10F illustrate aspects of a grasper 224'. As illustrated, the grasper 224' has a profile to facilitate a connection with the valve anchor 104a when loading the prosthesis onto the delivery device. In some embodiments, the grasper 224a' has a generally smooth profile. As illustrated in FIGS. 10E and 10F, the tang of the grasper 224a' has a protrusion 226a' with an angled distal portion 225a' and a rounded proximal portion 227a' to facilitate interconnection with the valve anchor 104a.

For example, in some embodiments, the tang of the grasper 224a' can further include an angled distal portion 229a'. Advantageously, the angled and rounded features of the profile of the grasper 224a' can promote smooth engagement and disengagement with the valve anchor 104a. In some embodiments, the engagement surfaces of the grasper 224a' can be electropolished.

FIGS. 10G and 10H illustrate an embodiment of a delivery device 200b that comprises a grasper mechanism that may engage with a valve anchor 204b. In some embodiments, valve anchor 204b may comprise a clasper tang located at the base portion of the U-shaped members, as discussed above with respect to FIG. 6H. Optionally, the valve anchor 204b may be similar or identical to the valve anchor 104g described in FIG. 6H, the features of which are not discussed again here for brevity, but may be realized in such a combination.

With reference to FIG. 10G, the delivery device 200b is shown with proximal sheath extending over both the valve anchor 204b and the support frame 102. Thus, in accordance with some embodiments, in the compressed or delivery configuration shown in FIG. 10G, the link mechanism can extend between the valve anchor 204b and the support frame 102 and be at least partially enclosed within the proximal enclosure 210. In alternative embodiments of the delivery device 200b, the valve anchor 204b and the support frame 102 can both be enclosed within the proximal sheath component prior to and during delivery prior to releasing the valve anchor 204b.

For example, the delivery device 200b, shown in FIG. 10G, can comprise a grasper 224b that can extend across the valve anchor 204b to engage with and control the base portion of the valve anchor 204b. Optionally, the proximal enclosure 210 can be recessed or have a reduced diameter portion to permit the valve anchor 204b and the graspers 224b attached thereto to have a lower profile in a compressed or undeployed configuration.

With reference to FIG. 10H, the delivery device 200b is shown with the valve anchor 204b in a deployed configuration. In some embodiments, by engaging the base portion of the valve anchor 204b, the grasper 224b can precisely engage with and control the longitudinal position of the valve anchor 104b. Thus, the graspers 224b can be used to control the articulation of the valve anchor 204b as desired by the clinician.

Further, in some embodiments, by allowing the graspers 224b to engage the base portion of the valve anchor 204b, the motion of the link mechanism 160 can be limited to the desired portion of the valve anchor 204b. Thus, the link mechanism 160 will not slide along an undesired path or leg of the U-shaped member, thus tending to ensure that the link moves as intended.

Advantageously, the grasper mechanism can be used to securely couple a portion of the valve anchor with the delivery device. This can beneficially improve maneuverability and permit the clinician to control movement, operation, and deployment of the valve anchor while preventing inversion of the valve anchor 204b.

Accordingly, in at least one embodiment, a clinician can manipulate the valve anchor by engaging or coupling an engagement portion or protrusion of a grasper with a clasper tang of a valve anchor. The engagement portion and the clasper tang can be restricted from relative radial movement (to thereby remain longitudinally engaged and secured relative to each other) by enclosing the engagement portion and the clasper tang within a tubular enclosure. In order to disengage the engagement portion and the clasper tang, the clinician can relatively advance the engagement portion distally beyond an end of the tubular enclosure. Once in this position, the clasper tang can tend to be pulled radially outwardly as the valve anchor expands radially, thereby disengaging the clasper tang from the engagement portion. Thereafter, the engagement portion can be retracted or withdrawn into the tubular enclosure. In some embodiments, the engagement portion engages a window or protrusion of the clasper tang. In some embodiments, the engagement portion is a pin or slot. In some embodiments, each grasper can include a plurality of engagement portions or protrusions.

Illustration of Subject Technology as Clauses

Various examples of aspects of the disclosure are described as clause sets having numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A valve prosthesis comprising: a valve anchor having at least one U-shaped member extending about a longitudinal axis of the valve anchor, the U-shaped member having a peak portion and a base portion, the peak portion having an engagement area, the valve anchor being expandable from a compressed configuration for engaging a native valve structure; an expandable valve frame having a compressed configuration, an expanded configuration, and first and second end portions, the valve frame being configured to expand within the valve anchor at the native valve structure; and a link mechanism interconnecting the valve anchor with the valve frame, the link mechanism being coupled to the valve frame and being slidably coupled to the U-shaped member, the link mechanism being slidable along the U-shaped member from the base portion to be captured within the peak portion engagement area, wherein the link mechanism limits axial movement of the valve frame relative to the valve anchor when captured within the peak portion engagement area.

Clause 2. The valve prosthesis of Clause 1, wherein (i) in a delivery position, the valve anchor and the valve frame are in the compressed configuration, the valve frame is positioned distal to the valve anchor, and the link mechanism extends from the valve anchor base portion across the valve frame first end portion toward the valve frame second end portion, (ii) in an intermediate expanded position, the valve anchor is in an expanded configuration, the valve frame is in the compressed configuration, the valve frame is positioned proximal to the valve anchor, and the link mechanism extends from the valve anchor peak portion toward the valve frame first end portion, and (iii) in an overlapping position, the valve anchor and the valve frame longitudinally overlap each other, the valve frame is positioned within the valve anchor, and the link mechanism extends from the valve anchor peak portion across the valve frame toward the valve frame second end portion.

Clause 3. The valve prosthesis of any preceding Clause, wherein when the link mechanism is engaged in the engagement area, the valve anchor is permitted to expand toward the expanded configuration.

Clause 4. The valve prosthesis of any preceding Clause, wherein when the valve anchor and the valve frame are in the compressed configuration, the link mechanism has a longitudinal extent of between about 110% and about 170% of a longitudinal length of the valve anchor.

Clause 5. The valve prosthesis of any preceding Clause, wherein when the valve anchor and the valve frame are in the expanded configuration, the link mechanism has a longitudinal extent of between about 70% and about 130% of a longitudinal length of the valve anchor.

Clause 6. The valve prosthesis of any preceding Clause, wherein the link mechanism comprises a suture.

Clause 7. The valve prosthesis of Clause 6, the valve anchor comprises a plurality of U-shaped members, the suture having a weave pattern in which the suture extends from (i) a first circumferential position at the valve frame, (ii) then to a first leg of a first U-shaped member, (iii) then to a second leg of a second U-shaped member, the first U-shaped member being interconnected to the second U-shaped member, (iv) and then to the first circumferential position.

Clause 8. The valve prosthesis of Clause 7, wherein the second U-shaped member comprises a link motion limiter extending from a medial location of the base portion thereof.

Clause 9. The valve prosthesis of Clause 8, wherein the link mechanism comprises a plurality of sutures.

Clause 10. The valve prosthesis of Clause 9, wherein the weave pattern of a second suture of the plurality of sutures extends (i) from a first leg of the second U-shaped member to (ii) a second leg of a third U-shaped member and, (iii) then to a second circumferential position at the valve frame.

Clause 11. The valve prosthesis of Clause 6, the valve anchor comprises a plurality of U-shaped members, the suture having a weave pattern in which the suture extends from (i) a first circumferential position at the valve frame, (ii) then to a first leg of a first U-shaped member, (iii) then to a second leg of a second U-shaped member, the first U-shaped member being interconnected to the second U-shaped member, (iv) and then to a second circumferential position at the valve frame, different from the first circumferential position.

Clause 12. The valve prosthesis of Clause 11, wherein the suture comprises a continuous suture loop interwoven with the valve frame and the valve anchor.

Clause 13. The valve prosthesis of Clause 12, wherein the weave pattern of the continuous suture loop further extends (i) from the first leg of the first U-shaped member to the second leg of the second U-shaped member on a first side of a link motion limiter of the second U-shaped member, wherein the link motion limiter extends from a medial location of the base portion thereof, (ii) then to the second circumferential position at the valve frame, (iii) then to a first leg of the second U-shaped member on a second side of the link motion limiter, (iv) then to a second leg of a third U-shaped member, and (v) then to a third circumferential position at the valve frame.

Clause 14. The valve prosthesis of Clause 13, wherein the first, second, and third U-shaped members each comprises a respective link motion limiter, and wherein in the weave pattern of the continuous suture loop, the link mechanism is coupled to a given U-shaped member on both sides of the link motion limiter.

Clause 15. The valve prosthesis of Clause 12, the valve anchor comprises a plurality of U-shaped members, the link mechanism being interwoven with three U-shaped members of the valve anchor, and wherein a loop length of the continuous suture loop is between about 80% to about 120% of a sum of (i) a compressed circumference of the valve frame and (ii) six times a longitudinal length of the valve frame.

Clause 16. The valve prosthesis of Clause 6, wherein the valve anchor comprises first, second, and third U-shaped members, each of the first, second, and third U-shaped members having a link motion limiter extending from a medial location of the base portion thereof, and wherein the link mechanism comprises a continuous suture loop extending (i) from a given U-shaped member on a first side of the link motion limiter, (ii) then to a given circumferential position at the valve frame, and (iii) then to the given U-shaped member on a second side of the link motion limiter.

Clause 17. The valve prosthesis of any preceding Clause, wherein the peak portions of adjacent U-shaped members are coupled together to form a respective engagement area.

Clause 18. The valve prosthesis of any preceding Clause, wherein the engagement area of the peak portion comprises double peaks having a cove shape disposed therebetween for receiving and retaining the link mechanism therein.

Clause 19. A method for delivering a prosthetic heart valve prosthesis to a native valve structure of a patient, the method comprising: introducing the valve prosthesis into the patient at the implantation site, the valve prosthesis including a valve anchor having a U-shaped member with a peak portion and a base portion, an expandable valve frame, and a link mechanism interconnecting the valve anchor and the valve frame, the valve anchor being restrained in a compressed configuration within a proximal sheath, the valve frame being restrained in a compressed configuration within a distal carrier assembly; permitting expansion of the base portion of the valve anchor; distally urging the base portion of the valve anchor into engagement with a native valve structure; proximally retracting the valve frame relative to the valve anchor to slide the link mechanism proximally toward an engagement area of the peak portion to urge the link mechanism into the engagement area, thereby capturing the link mechanism therein and restricting a range of movement of the valve frame relative to the valve anchor; releasing the peak portion of the valve anchor to permit the valve anchor to expand against the native valve structure; and permitting expansion of the valve frame within a lumen of the valve anchor.

Clause 20. The method of Clause 19, wherein prior to the permitting expansion of the valve frame, the method further comprises distally advancing the valve frame into the valve anchor.

Clause 21. The method of Clause 20, wherein the distally advancing the valve frame into the valve anchor comprises distally advancing the valve frame until further distal movement of the valve frame relative to the valve anchor is restricted by the link mechanism.

Clause 22. The method of Clause 19-21, wherein after the proximally retracting the valve frame, the method further comprises distally advancing the valve frame, with the link mechanism being engaged at the engagement area of the peak portion of the valve anchor, until the link mechanism is taut and further distally advancing the valve frame to pull the valve anchor distally relative to the native valve structure.

Clause 23. The method of Clause 19-22, wherein after the proximally retracting the valve frame, the method further comprises rotating the valve frame, with the link mechanism being engaged at the engagement area of the peak portion of the valve anchor, to rotationally adjust a position of the valve anchor relative to the native valve structure.

Clause 24. A valve prosthesis comprising: a valve anchor having at least one U-shaped member extending about a longitudinal axis of the valve anchor, the U-shaped member having a peak portion and a base portion, the valve anchor being expandable from a compressed configuration for engaging a native valve structure; an expandable valve frame having a compressed configuration, and an expanded configuration, the valve frame being configured to expand within the valve anchor at the native valve structure; and a link mechanism interconnecting the valve anchor with the valve frame, the link mechanism being coupled to the valve frame and being coupled to the U-shaped member, wherein the link mechanism limits axial movement of the valve frame relative to the valve anchor.

Clause 25. A valve prosthesis comprising: a valve anchor having at least one U-shaped member extending about a longitudinal axis of the valve anchor, the U-shaped member having a peak portion and a base portion, the peak portion having an engagement area, the base portion having a clasper tang extending from a medial location thereof, the valve anchor being expandable from a compressed configuration for engaging a native valve structure.

Clause 26. The valve prosthesis of Clause 25, wherein the clasper tang is configured to be coupled to a grasper mechanism of a delivery device.

Clause 27. The valve prosthesis of Clause 25 or 26, further comprising: an expandable valve frame having a compressed configuration, an expanded configuration, and first and second end portions, the valve frame being configured to expand within the valve anchor at the native valve structure.

Clause 28. The valve prosthesis of Clause 27, further comprising: a link mechanism interconnecting the valve anchor with the valve frame, the link mechanism being coupled to the valve frame and being slidably coupled to the U-shaped member, the link mechanism being slidable along the U-shaped member from the base portion to be captured within the peak portion engagement area, wherein the link mechanism limits axial movement of the valve frame relative to the valve anchor when captured within the peak portion engagement area.

Clause 29. The valve prosthesis of Clause 28, wherein the link mechanism comprises a suture.

Clause 30. The valve prosthesis of Clause 29, the valve anchor comprises a plurality of U-shaped members, the suture having a weave pattern in which the suture extends from (i) a first circumferential position at the valve frame, (ii) then to a first leg of a first U-shaped member, (iii) then to a second leg of a second U-shaped member, the first U-shaped member being interconnected to the second U-shaped member, (iv) and then to the first circumferential position.

Clause 31. The valve prosthesis of Clause 30, wherein the clasper tang is configured to limit motion of the suture.

Clause 32. The valve prosthesis of Clause 30, wherein the plurality of U-shaped members each comprises a respective clasper tang, and wherein in the weave pattern of the suture, the link mechanism is coupled to a given U-shaped member on both sides of the clasper tang.

Clause 33. A valve prosthesis comprising: a valve anchor having at least one U-shaped member extending about a longitudinal axis of the valve anchor, the valve anchor being expandable from a compressed configuration for engaging a native valve structure; an expandable valve frame having a compressed configuration, an expanded configuration, and first and second end portions, the valve frame being configured to expand within the valve anchor at the native valve structure; and a link mechanism interconnecting the valve anchor with the valve frame, the link mechanism being fixedly coupled to the valve frame and to the U-shaped member, wherein the link mechanism limits axial movement of the valve frame relative to the valve anchor.

Clause 34. The valve prosthesis of Clause 33, wherein when the valve anchor and the valve frame are in the compressed configuration, the link mechanism has a longitudinal extent of between about 110% and about 170% of a longitudinal length of the valve anchor.

Clause 35. The valve prosthesis of Clause 34, wherein the link mechanism elongates to the longitudinal extent.

Clause 36. The valve prosthesis of Clause 34, wherein the link mechanism stretches to the longitudinal extent.

Clause 37. The valve prosthesis of Clause 34, wherein the link mechanism deforms to the longitudinal extent.

Clause 38. The valve prosthesis of Clause 33-37, wherein the link mechanism comprises silicone or polyurethane.

Clause 39. The valve prosthesis of Clause 33-38, wherein when the valve anchor and the valve frame are in the expanded configuration, the link mechanism has a longitudinal extent of between about 70% and about 130% of a longitudinal length of the valve anchor.

Clause 40. The valve prosthesis of Clause 33-39, wherein the link mechanism comprises a suture.

Clause 41. The valve prosthesis of Clause 40, the valve anchor comprises a plurality of U-shaped members, the suture having a weave pattern in which the suture extends from (i) a first circumferential position at the valve frame, (ii) then to a first leg of a first U-shaped member, (iii) then to a second leg of a second U-shaped member, the first U-shaped member being interconnected to the second U-shaped member, (iv) and then to the first circumferential position.

Clause 42. The valve prosthesis of Clause 33-41, wherein the link mechanism is fixedly coupled to a leg of the valve anchor.

Clause 43. The valve prosthesis of Clause 33-42, wherein the link mechanism comprises a coiled portion.

Clause 44. The valve prosthesis of Clause 33-43, wherein the link mechanism comprises a laser-cut portion.

Clause 45. The valve prosthesis of Clause 33-44, further comprising a one-way interconnect mechanism, the one-way interconnect mechanism allowing proximal movement of the link mechanism.

Clause 46. The valve prosthesis of Clause 45, wherein the one-way interconnect mechanism prevents distal advancement of the link mechanism relative to the one-way interconnect mechanism.

Clause 47. The valve prosthesis of Clause 45, wherein the one-way interconnect mechanism comprises a mechanism body with an aperture, the aperture permitting the link mechanism to pass therethrough.

Clause 48. The valve prosthesis of Clause 47, wherein the link mechanism ratchets through the one-way interconnect mechanism.

Clause 49. A method for delivering a prosthetic heart valve prosthesis to a native valve structure of a patient, the method comprising: introducing the valve prosthesis into the patient at the implantation site, the valve prosthesis including a valve anchor having a U-shaped member, an expandable valve frame, and a link mechanism fixedly coupled to the valve anchor and the valve frame, the valve anchor being restrained in a compressed configuration within a proximal sheath, the valve frame being restrained in a compressed configuration within a distal carrier assembly; permitting expansion of the valve anchor; distally urging a base portion of the valve anchor into engagement with a native valve structure; restricting a range of movement of the valve frame relative to the valve anchor via the link mechanism; releasing a peak portion of the valve anchor to permit the valve anchor to expand against the native valve structure; and permitting expansion of the valve frame within a lumen of the valve anchor.

Clause 50. The method of Clause 49, wherein prior to the permitting expansion of the valve frame, the method further comprises distally advancing the valve frame into the valve anchor.

Clause 51. The method of Clause 50, wherein the distally advancing the valve frame into the valve anchor comprises distally advancing the valve frame until further distal movement of the valve frame relative to the valve anchor is restricted by the link mechanism.

Clause 52. The method of Clause 49-51, wherein after the proximally retracting the valve frame, the method further comprises distally advancing the valve frame, applying tension to the link mechanism until the link mechanism is taut and further distally advancing the valve frame to pull the valve anchor distally relative to the native valve structure.

Clause 53. The method of Clause 49-52, wherein after the proximally retracting the valve frame, the method further comprises rotating the valve frame and applying tension to the link mechanism to rotationally adjust a position of the valve anchor relative to the native valve structure.

Clause 54. The method of Clause 49-53, further comprising reducing a longitudinal extent of the link mechanism.

Clause 55. The method of Clause 54, further comprising coiling the link mechanism to reduce the longitudinal extent of the link mechanism.

Clause 56. The method of Clause 54, further comprising proximally moving the link mechanism through a one-way interconnect to reduce the longitudinal extent of the link mechanism.

Clause 57. The method of Clause 56, further comprising preventing distal advancement of the link mechanism through the one-way interconnect.

Further Considerations

In some embodiments, any of the clauses herein may depend from any one of the independent clauses or any one of the dependent clauses. In some embodiments, any of the clauses (e.g., dependent or independent clauses) may be combined with any other one or more clauses (e.g., dependent or independent clauses). In some embodiments, a claim may include some or all of the words (e.g., steps, operations, means or components) recited in a clause, a sentence, a phrase or a paragraph. In some embodiments, a claim may include some or all of the words recited in one or more clauses, sentences, phrases or paragraphs. In some embodiments, some of the words in each of the clauses, sentences, phrases or paragraphs may be removed. In some embodiments, additional words or elements may be added to a clause, a sentence, a phrase or a paragraph. In some embodiments, the subject technology may be implemented without utilizing some of the components, elements, functions or operations described herein. In some embodiments, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the term "distal" can denote a location or direction that is away from a point of interest, such as a control unit or region of the delivery system that will be used to deliver a valve prosthesis to a native valve annulus. Additionally, the term "proximal" can denote a location or direction that is closer to a point of interest, such as a control unit or region of the delivery system that will be used to deliver a valve prosthesis.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A valve prosthesis comprising:
   a valve anchor having at least one U-shaped member extending about a longitudinal axis of the valve anchor, the U-shaped member having a peak portion and a base portion, the peak portion having an engagement area, the valve anchor being expandable from a compressed configuration for engaging a native valve structure, wherein the peak portions of adjacent U-shaped members are coupled together to form a respective engagement area;
   an expandable valve frame having a compressed configuration, an expanded configuration, and first and second end portions, the valve frame being configured to expand within the valve anchor at the native valve structure; and
   a link mechanism interconnecting the valve anchor with the valve frame, the link mechanism being coupled to the valve frame and being slidably coupled to the U-shaped member, the link mechanism being slidable along the U-shaped member from the base portion to be captured within the peak portion engagement area, wherein the link mechanism limits axial movement of the valve frame relative to the valve anchor when captured within the peak portion engagement area.

2. The valve prosthesis of claim 1, wherein (i) in a delivery position, the valve anchor and the valve frame are in the compressed configuration, the valve frame is positioned distal to the valve anchor, and the link mechanism extends from the valve anchor base portion across the valve frame first end portion toward the valve frame second end portion, (ii) in an intermediate expanded position, the valve anchor is in an expanded configuration, the valve frame is in the compressed configuration, the valve frame is positioned proximal to the valve anchor, and the link mechanism extends from the valve anchor peak portion toward the valve frame first end portion, and (iii) in an overlapping position, the valve anchor and the valve frame longitudinally overlap each other, the valve frame is positioned within the valve anchor, and the link mechanism extends from the valve anchor peak portion across the valve frame toward the valve frame second end portion.

3. The valve prosthesis of claim 1, wherein when the link mechanism is engaged in the engagement area, the valve anchor is permitted to expand toward the expanded configuration.

4. The valve prosthesis of claim 1, wherein the link mechanism comprises a suture.

5. The valve prosthesis of claim 4, the valve anchor comprises a plurality of U-shaped members, the suture having a weave pattern in which the suture extends from (i) a first circumferential position at the valve frame, (ii) then to a first leg of a first U-shaped member, (iii) then to a second leg of a second U-shaped member, the first U-shaped member being interconnected to the second U-shaped member, (iv) and then to the first circumferential position.

6. The valve prosthesis of claim 5, wherein the second U-shaped member comprises a link motion limiter extending from a medial location of the base portion thereof.

7. The valve prosthesis of claim 4, the valve anchor comprises a plurality of U-shaped members, the suture having a weave pattern in which the suture extends from (i) a first circumferential position at the valve frame, (ii) then to a first leg of a first U-shaped member, (iii) then to a second leg of a second U-shaped member, the first U-shaped member being interconnected to the second U-shaped member, (iv) and then to a second circumferential position at the valve frame, different from the first circumferential position.

8. The valve prosthesis of claim 7, wherein the suture comprises a continuous suture loop interwoven with the valve frame and the valve anchor.

9. The valve prosthesis of claim 4, wherein the valve anchor comprises first, second, and third U-shaped members, each of the first, second, and third U-shaped members having a link motion limiter extending from a medial location of the base portion thereof, and wherein the link mechanism comprises a continuous suture loop extending (i) from a given U-shaped member on a first side of the link motion limiter, (ii) then to a given circumferential position at the valve frame, and (iii) then to the given U-shaped member on a second side of the link motion limiter.

10. The valve prosthesis of claim 1, wherein the engagement area of the peak portion comprises double peaks having a cove shape disposed therebetween for receiving and retaining the link mechanism therein.

11. A method for delivering a prosthetic heart valve prosthesis to a native valve structure of a patient, the method comprising:
  introducing the valve prosthesis into the patient at the implantation site, the valve prosthesis including a valve anchor having a U-shaped member with a peak portion and a base portion, an expandable valve frame, and a link mechanism interconnecting the valve anchor and the valve frame, the valve anchor being restrained in a compressed configuration within a proximal sheath, the valve frame being restrained in a compressed configuration within a distal carrier assembly;
  permitting expansion of the base portion of the valve anchor;
  distally urging the base portion of the valve anchor into engagement with a native valve structure;
  proximally retracting the valve frame relative to the valve anchor to slide the link mechanism proximally toward an engagement area of the peak portion to urge the link mechanism into the engagement area, thereby capturing the link mechanism therein and restricting a range of movement of the valve frame relative to the valve anchor, wherein the peak portions of adjacent U-shaped members are coupled together to form a respective engagement area;
  releasing the peak portion of the valve anchor to permit the valve anchor to expand against the native valve structure; and
  permitting expansion of the valve frame within a lumen of the valve anchor.

12. The method of claim 11, wherein prior to the permitting expansion of the valve frame, the method further comprises distally advancing the valve frame into the valve anchor.

13. The method of claim 12, wherein the distally advancing the valve frame into the valve anchor comprises distally advancing the valve frame until further distal movement of the valve frame relative to the valve anchor is restricted by the link mechanism.

14. The method of claim 11, wherein after the proximally retracting the valve frame, the method further comprises distally advancing the valve frame, with the link mechanism being engaged at the engagement area of the peak portion of the valve anchor, until the link mechanism is taut and further distally advancing the valve frame to pull the valve anchor distally relative to the native valve structure.

15. The method of claim 11, wherein after the proximally retracting the valve frame, the method further comprises rotating the valve frame, with the link mechanism being engaged at the engagement area of the peak portion of the valve anchor, to rotationally adjust a position of the valve anchor relative to the native valve structure.

16. A valve prosthesis comprising a valve anchor having at least one U-shaped member extending about a longitudinal axis of the valve anchor, the U-shaped member having a peak portion and a base portion therebetween, the peak portion having an engagement area wherealong a link mechanism can be captured for limiting axial movement of link mechanism coupled thereby to the valve anchor and limiting movement of the link mechanism along the U-shaped member, the valve anchor being expandable from a compressed configuration for engaging a native valve structure.

17. The valve prosthesis of claim 16, wherein the base portion comprises a clasper tang extending from a medial portion thereof, and the clasper tang is configured to be coupled to a grasper mechanism of a delivery device.

18. The valve prosthesis of claim 16, further comprising an expandable valve frame having a compressed configuration, an expanded configuration, and first and second end portions, the valve frame being configured to expand within the valve anchor at the native valve structure.

19. The valve prosthesis of claim 18, further comprising the link mechanism interconnecting the valve anchor with the valve frame, the link mechanism being coupled to the valve frame and being slidably coupled to the U-shaped member, the link mechanism being slidable along the U-shaped member from the base portion to be captured within the peak portion engagement area, wherein the link mechanism limits axial movement of the valve frame relative to the valve anchor when captured within the peak portion engagement area.

20. A valve prosthesis comprising:
- a valve anchor having at least first and second U-shaped members that extend about a longitudinal axis of the valve anchor and that are interconnected to each other, each U-shaped member having a peak portion, a base portion, and first and second legs, the peak portion having an engagement area, the valve anchor being expandable from a compressed configuration for engaging a native valve structure;
- an expandable valve frame having a compressed configuration, an expanded configuration, and first and second end portions, the valve frame being configured to expand within the valve anchor at the native valve structure; and
- a suture interconnecting the valve anchor with the valve frame, the suture being coupled to the valve frame and being slidably coupled to the valve anchor, the suture having a weave pattern in which the suture extends from (i) a first circumferential position at the valve frame, (ii) then to the first leg of the first U-shaped member, (iii) then to the second leg of the second U-shaped member, (iv) and then to the first circumferential position or a second circumferential position at the valve frame, different from the first circumferential position, the suture being slidable along each U-shaped member from the base portion to be captured within the peak portion engagement area for limiting axial movement of the valve frame relative to the valve anchor.

21. The valve prosthesis of claim 20, wherein the second U-shaped member comprises a link motion limiter extending from a medial location of the base portion thereof.

22. The valve prosthesis of claim 20, wherein the suture comprises a continuous suture loop interwoven with the valve frame and the valve anchor.

* * * * *